(12) United States Patent
Guo et al.

(10) Patent No.: US 12,178,880 B2
(45) Date of Patent: *Dec. 31, 2024

(54) ANTIBODY-DRUG CONJUGATE, AND INTERMEDIATE THEREOF, PREPARATION METHOD THEREFOR, AND APPLICATION THEREOF

(71) Applicant: SHANGHAI FUDAN-ZHANGJIANG BIO-PHARMACEUTICAL CO., LTD., Shanghai (CN)

(72) Inventors: Qingsong Guo, Shanghai (CN); Yijun Shen, Shanghai (CN); Tong Yang, Shanghai (CN); Bin Bao, Shanghai (CN); Bei Gao, Shanghai (CN); Fang Wu, Shanghai (CN); Jun Xu, Shanghai (CN)

(73) Assignee: SHANGHAI FUDAN-ZHANGJIANG BIO-PHARMACEUTICAL CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/254,882

(22) PCT Filed: Dec. 4, 2020

(86) PCT No.: PCT/CN2020/133872
§ 371 (c)(1),
(2) Date: May 30, 2023

(87) PCT Pub. No.: WO2022/116141
PCT Pub. Date: Jun. 9, 2022

(65) Prior Publication Data
US 2024/0016949 A1    Jan. 18, 2024

(51) Int. Cl.
*A61K 47/68* (2017.01)
*C07K 16/32* (2006.01)

(52) U.S. Cl.
CPC .... *A61K 47/68037* (2023.08); *A61K 47/6845* (2017.08); *C07K 16/32* (2013.01)

(58) Field of Classification Search
CPC .......... A61K 47/6803; A61K 47/68037; A61K 47/6889; A61K 47/6851
See application file for complete search history.

(56) References Cited

U.S. PATENT DOCUMENTS

| 7,960,516 | B2 * | 6/2011 | Matheus | ............ | C07K 16/2863 |
| | | | | | 530/387.3 |
| 2007/0071675 | A1 | 3/2007 | Wu et al. | | |
| 2022/0233708 | A1 * | 7/2022 | Bao | .................... | A61K 47/6889 |

FOREIGN PATENT DOCUMENTS

| CA | 2937561 | A1 | | 8/2015 | | |
| CA | 3053749 | A1 | | 9/2018 | | |
| CN | 103764681 | A | | 4/2014 | | |
| CN | 106163559 | A | | 11/2016 | | |
| CN | 110724194 | A | | 1/2020 | | |
| CN | 111001012 | | * | 4/2020 | ............. | A61K 47/68 |
| EP | 3666788 | A1 | | 6/2020 | | |
| JP | 2014526895 | A | | 10/2014 | | |
| JP | 2017503784 | A | | 2/2017 | | |
| JP | 2017510548 | A | | 4/2017 | | |
| JP | 2017537893 | A | | 12/2017 | | |
| JP | 2018515137 | A | | 6/2018 | | |
| WO | 0177342 | A1 | | 10/2001 | | |
| WO | WO-2004029207 | A2 | * | 4/2004 | ............. | A61K 39/00 |
| WO | 2012019024 | A2 | | 2/2012 | | |
| WO | 2013173337 | A2 | | 11/2013 | | |
| WO | WO-2015095755 | A1 | * | 6/2015 | ............. | A61K 47/60 |
| WO | 2015113476 | A1 | | 8/2015 | | |
| WO | 2015146132 | A1 | | 10/2015 | | |
| WO | 2015155998 | A1 | | 10/2015 | | |
| WO | 2016070089 | A2 | | 5/2016 | | |
| WO | 2016177664 | A1 | | 11/2016 | | |
| WO | 2018159582 | A1 | | 9/2018 | | |
| WO | WO-2019011852 | A1 | * | 1/2019 | ............. | A61K 39/00 |
| WO | 2019034176 | A1 | | 2/2019 | | |
| WO | WO-2020259258 | A1 | * | 12/2020 | ......... | A61K 31/4745 |

OTHER PUBLICATIONS

STNext property data for exatecan, downloaded from the web on Dec. 28, 2023 (Year: 2023).*
Ke et al, International Journal of Pharmaceutics, 2015, vol. 548, pp. 682-688 (Year: 2015).*
Morissette et al (Advanced Drug Delivery Reviews, 2004, vol. 56, pp. 275-300) (Year: 2004).*
Cazzamalli et al (Journal of Controlled Release, 2017, vol. 246, pp. 39-45) (Year: 2017).*
Agatsuma (Yakugaku Zasshi, 2017, vol. 137, pp. 545-550) (Year: 2017).*
Translation of CN-111001012, downloaded from the web Dec. 27, 2023 (Year: 2023).*
Sep. 8, 2021 International Search Report issued in International Patent Application No. PCT/CN2020/133872.
Sep. 8, 2021 Written Opinion of the International Searching Authority issued in International Patent Application No. PCT/CN2020/133872.

(Continued)

*Primary Examiner* — Karen A. Canella
(74) *Attorney, Agent, or Firm* — Houston Beshining Law Office PLLC; Liangang Ye

(57) ABSTRACT

An antibody-drug conjugate, and an intermediate thereof, a preparation method therefor, and an application thereof. Provided is an antibody-drug conjugate as represented by formula I. The compound has good targetability, has a good inhibitory effect on HER3-positive tumor cells, and has good druggability and high safety. The antibody-drug conjugate has an inhibitory effect on HER3, has an inhibitory effect on SK-BR-3 and SW620 cells, and also has a good inhibitory effect on at least one of 22Rv1, LNCaP, NCI-H820, OVCAR-8, and HCC827 cells.

6 Claims, 1 Drawing Sheet

Specification includes a Sequence Listing.

(56) References Cited

OTHER PUBLICATIONS

Berge et al., "Pharmaceutical Salts", Journal of Pharmaceutical Science 66: 1-19 (1977).
Handbook of Pharmaceutical Salts: Properties, Selection, and Use (P. Heinrich Stahl and Camille G. Wermuth, ed., Wiley-VCH, 2002.
Aug. 25, 2023 First Office Action issued in Canada Patent Application No. 3,200,812.
Nov. 14, 2023 First Office Action issued in Japan Patent Application No. 2023-534207.
Jan. 22, 2024 Second Office Action issued in Canada Patent Application No. 3,200,812.
Dec. 7, 2023 First Office Action issued in Russia Patent Application No. 2023117643.
Feb. 16, 2024 extended European Search Report issued in European Patent Application No. 20963987.1.
Yonesaka Kimio et al: "An HER3-targeting antibody-drug conjugate incorporating a DNA topoisomerase I inhibitor U3-1402 conquers EGFR tyrosine kinase inhibitor-resistant NSCLC", Oct. 2018, 1398-1409.
Poudel Yam B. et al: "Chemical Modification of Linkers Provides Stable Linker-Payloads for the Generation of Antibody-Drug Conjugates", Nov. 2020, 2190-2194.
Jun. 3, 2024 Second Office Action issued in Russia Patent Application No. 2023117643.
Abou-Alfa G.K. et al.: "Randomized Phase III Study of Exatecan and Gemcitabine Compared with Gemcitabine Alone in Untreated Advanced Pancreatic Cancer", Journal of Clinical Oncology, 2006, v. 24 (27): 4441-7.
Hosseini S. Kh et al.: "Camptothecin and its analog SN-38, the active metabolite of irinotecan, inhibit binding of the transcriptional regulator and oncoprotein FUBP1 to its DNA target sequence FUSE", Biochem. Pharmacol., 2017, v. 146:53-62.
Hashimoto Yu et al.: "A Novel HER3-Targeting Antibody-Drug Conjugate, U3-1402, Exhibits Potent Therapeutic Efficacy through the Delivery of Cytotoxic Payload by Efficient Internalization", Clin. Cancer Res., 2019, v. 25 (23): 7151-7161.
Sievers, E. L. et al, Antibody-Drug Conjugates in Cancer Therapy. Annual Review of Medicine, 2013, 64(1), p. 15-29.
Third Office Action issued on Sep. 17, 2024 for a corresponding Canadian Patent Application No. 3,200,812.
Third Office Action issued on Oct. 1, 2024 for a corresponding Russian Patent Application No. 2023117643.
Zheng K. et al: "Characterization of Ring-Opening Reaction of Succinimide Linkers in ADCs", Journal of Pharmaceutical Sciences, 2019, v. 108, p. 133-141.

* cited by examiner

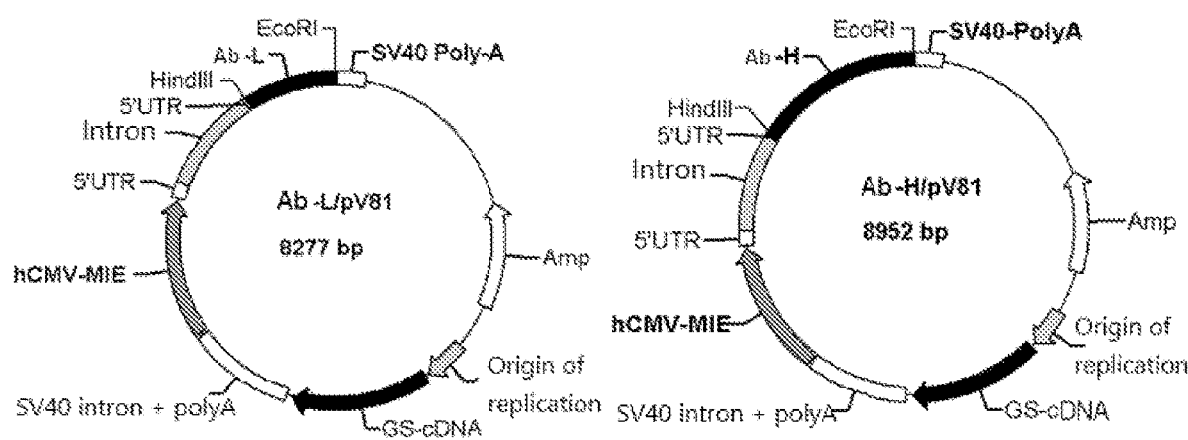

ANTIBODY-DRUG CONJUGATE, AND INTERMEDIATE THEREOF, PREPARATION METHOD THEREFOR, AND APPLICATION THEREOF

REFERENCE TO SEQUENCE LISTING

The Sequence Listing is submitted concurrently with the specification as an ASCII formatted text file via EFS-Web, with a file name of "P23412116US-2-SEQ", a creation date of May 10, 2023, and a size of 13,930 bytes. The Sequence Listing filed via EFS-Web is part of the specification and is incorporated in its entirety by reference herein.

The present application is a National Stage of International Application No. PCT/CN2020/133872, filed on Dec. 4, 2020.

TECHNICAL FIELD

The present disclosure relates to the field of biomedicine, and in particularly relates to an antibody-drug conjugate, an intermediate thereof, a preparation method therefor, and a use thereof.

BACKGROUND

The HER family consists of four structurally similar and functionally related RTKs, namely HER1 (EGFR), HER2, HER3, and HER4, and dimerization between receptors is a basic condition for the HER family to exert its function and signal transduction activity. After receptor dimerization, it induces cross-phosphorylation of highly conserved kinase residues in the cell, which recruits and activates downstream proteins, triggering a signaling cascade that regulate processes such as cell proliferation, survival, migration, occurrence, and metastasis. Although HER3 can bind to Neuregulin (NRG), due to its lack of intrinsic tyrosine kinase activity, HER3 can only exert its function by forming heterodimers with other receptors. On the contrary, although HER2 has tyrosine kinase activity, there is no corresponding ligand to bind to it. The extracellular domain structure of HER2 is a natural open conformation, which allows HER2 to dimerize with other receptors without ligand activation. Therefore, HER2 is the preferred dimerization partner for HER3.

The formation of HER2-HER3 heterodimers can directly activate the PI3K/AKT pathway. The PI3K/AKT pathway is the most important signaling pathway that promotes tumor cell proliferation and is involved in regulating gene expression, cell metabolism, cell cytoskeleton rearrangement and other processes. Therefore, the HER2-HER3 heterodimer is considered to be the most potent dimer in the HER family in terms of signal transduction. Studies have shown that drugs that directly or indirectly inhibit the PI3K/AKT pathway can lead to increased transcription of HER3. Through negative feedback regulation of PI3K/AKT, HER3 expression is upregulated and activated, reactivating downstream pathways and resulting in drug resistance, which is related to drug resistance to anti-HER2 and anti-EGFR targeted therapies. In addition, NRG1, the main ligand of HER3, can participate in HER3 signal transduction and the like through paracrine and autocrine pathways, thereby inducing HER3 pathway activation and may also be involved in drug resistance to HER family targeted therapy. In addition, HER3 can also form dimers with other members of the HER family such as EGFR, as well as non-HER family members such as MET and IGF-1R, and participate in the occurrence and development of tumors. Given that HER3 can form heterodimers with other targets to deliver the strongest PI3K/AKT, and due to the lack of tyrosine kinase activity, the therapeutic drugs targeting HER3 mainly focus on the extracellular domain of HER3 to develop antibody drugs. Although there are currently multiple monoclonal antibody drugs or bispecific antibody drugs in the clinical research phase, existing data show that their clinical efficacy data are not significant enough and there is limited potential for further development.

Antibody-drug conjugate (ADC) is a new generation of targeted therapeutic drugs, mainly used for the treatment of cancer tumors. ADC drugs consist of three parts: a small molecule cytotoxic drug (Drug), an antibody (Antibody), and a linker (Linker) that links the antibody with the cytotoxic drug. The small molecule cytotoxic drug is bound to the antibody protein by chemical coupling. ADC drugs utilize antibodies to specifically recognize and guide small molecule drugs to cancer cell targets expressing cancer-specific antigens, and enter the cancer cells through endocytosis. The linker part is broken under the action of intracellular low pH value environment or lysosomal protease, releasing small molecular cytotoxic drugs, so as to achieve the effect of specifically killing cancer cells without damaging normal tissue cells. Therefore, ADC drugs have the characteristics of the targeted specificity of antibodies and the high toxicity of small molecule toxins to cancer cells at the same time, greatly expanding the effective therapeutic window of the drug. Clinical studies have proven that ADC drugs have high efficacy and are relatively stable in the blood, and can effectively reduce the toxicity of small molecule cytotoxic drugs (chemotherapy drugs) to the circulatory system and healthy tissues, and are currently a hot spot in the development of anti-cancer drugs internationally.

The Fc-terminal of antibody drugs contains different receptors, mainly including Fcγ receptor (FcγR), neonatal Fc receptor (FcRn), and C-type lectin receptor. There are various subtypes of FcγR receptors, and different FcγRs mediate different effector functions including ADCC, ADCP, and CDC, which are crucial factors connecting cellular immunity and humoral immunity. The effector function mediated by FcγR plays an important role in the effectiveness of some therapeutic antibodies in monoclonal antibody drugs. However, in ADC drugs, FcγR can mediate the internalization, transport, and release of active molecules of ADC drugs in relevant cells by binding to the Fc of ADC drugs, leading to serious toxic events. For example, FcγRIIa (i.e., CD32a) can mediate DM1-type ADC drugs and resulting in the occurrence of toxic events such as thrombocytopenia. Therefore, reducing the binding of ADC drugs to FcγRIIa can reduce the killing of FcγRIIa cells by ADC drugs, thereby reducing the occurrence of toxic events mediated by FcγRIIa.

Due to the insufficient clinical efficacy of HER3 monoclonal antibody drugs, it is of great clinical value to develop antibody-drug conjugates based on this target with better efficacy or to develop antibody-drug conjugates that can reduce the binding to FcγRIIa.

Content of the Present Invention

The technical problem to be solved by the present disclosure is to overcome the current deficiency of limited types of antibody-drug conjugates, and the present disclosure provides an antibody-drug conjugate, an intermediate thereof, a preparation method therefor, and a use thereof.

The present disclosure has developed a class of antibody-drug conjugates with good targeting ability, strong inhibition effect on tumor cells that are positive for HER3 expression, and good druggability and high safety. The antibody-drug conjugate has an inhibitory effect on HER3, and also has an inhibitory effect on SK-BR-3 and SW620 cells, and also has a good inhibitory effect on at least one of 22Rv1, LNCaP, NCI-H820, OVCAR-8, and HCC827 cells.

The present disclosure solves the above technical problem through the following technical solutions.

The present disclosure provides an antibody-drug conjugate, a pharmaceutically acceptable salt thereof, a solvate thereof, or a solvate of the pharmaceutically acceptable salt thereof; the antibody-drug conjugate has a structure shown in formula I;

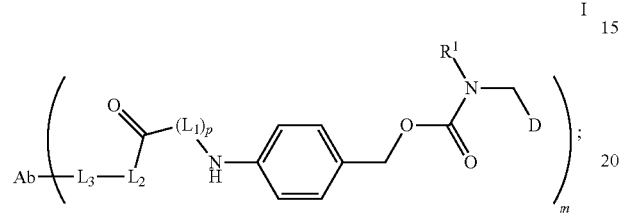

wherein Ab is a HER3 antibody or a variant of the HER3 antibody;
m is 2 to 8;
D is a cytotoxic drug topoisomerase inhibitor;
$R^1$ is $C_1$-$C_6$ alkyl substituted by one or more than one —$NR^{1-1}R^{1-2}$, $C_1$-$C_6$ alkyl substituted by one or more than one $R^{1-3}$ $S(O)_2$—, $C_1$-$C_6$ alkyl, $C_3$-$C_{10}$ cycloalkyl, $C_6$-$C_{14}$ aryl, or 5- to 14-membered heteroaryl; the heteroatom in the 5- to 14-membered heteroaryl is selected from one or more than one of N, O, and S, and the number of heteroatoms is 1, 2, 3, or 4; the $R^{1-1}$, $R^{1-2}$, and $R^{1-3}$ are each independently $C_1$-$C_6$ alkyl;
$L_1$ is independently one or more than one of phenylalanine residue, alanine residue, glycine residue, glutamic acid residue, aspartic acid residue, cysteine residue, glutamic acid residue, histidine residue, isoleucine residue, leucine residue, lysine residue, methionine residue, proline residue, serine residue, threonine residue, tryptophan residue, tyrosine residue, and valine residue; p is 2 to 4;
$L_2$ is

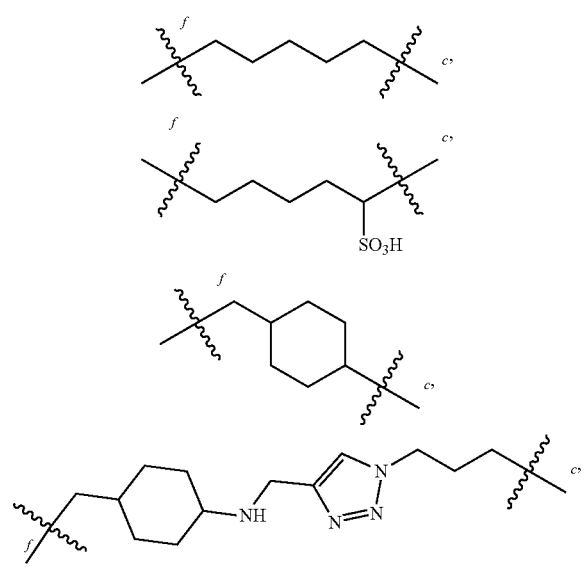

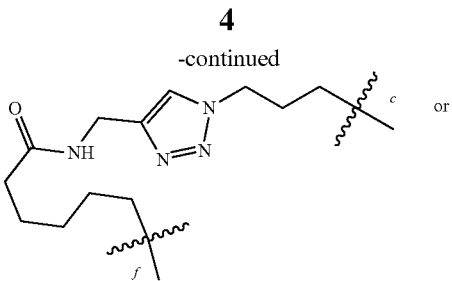

wherein n is independently 1 to 12, the c-terminal is connected to $L_1$ through a carbonyl group, and the f-terminal is connected to the d-terminal of $L_3$;
$L_3$ is

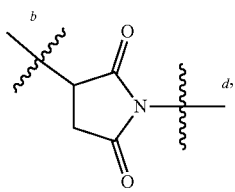 [SMILES: *C1CC(=O)N(*)C1=O]

wherein the b-terminal is connected to the Ab, and the d-terminal is connected to the f-terminal of $L_2$.

In a preferred embodiment of the present disclosure, certain groups of the antibody-drug conjugate are defined as follows, and the definition of any unmentioned groups is as described in any of the above embodiments (this paragraph is hereinafter referred to as "in a preferred embodiment of the present disclosure"):

The HER3 antibody is HER3 antibody A, wherein the amino acid sequence of the light chain in HER3 antibody A is shown in SEQ ID NO: 1, and the amino acid sequence of the heavy chain is shown in SEQ ID NO: 2.

In a preferred embodiment of the present disclosure, the variant of the HER3 antibody is a variant of HER3 antibody A.

In a preferred embodiment of the present disclosure, the variant of the HER3 antibody is at least 70%, 75%, 80%, 85%, 90%, 95%, 98%, or 99% identical to the HER3 antibody.

In a preferred embodiment of the present disclosure, for the variant of HER3 antibody A, the amino acid sequence of the light chain in the variant of HER3 antibody A is preferably shown in SEQ ID NO: 1.

In a preferred embodiment of the present disclosure, the amino acid sequence of the heavy chain in the variant of HER3 antibody A is the amino acid sequence shown in SEQ ID NO: 2 having one or more than one site mutation of E233P, L234V, L234F, L235A, L235E, or P331S. For example, having site mutations of E233P, L234V, and L235A (i.e., SEQ ID NO: 3), or having site mutations of L234F, L235E, and P331S (i.e., SEQ ID NO: 4), and the "more than one" is preferably two or three.

In a preferred embodiment of the present disclosure, the b-terminal of $L_3$ is preferably connected to the sulfhydryl group on the antibody in the form of a thioether. Taking

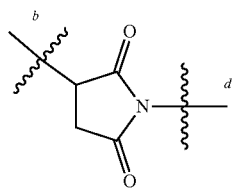

as an example, the connecting form of

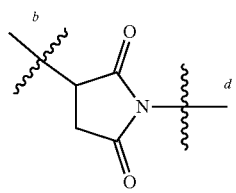 [SMILES: *C1CC(=O)N(*)C1=O]

with the cysteine residue in the antibody is

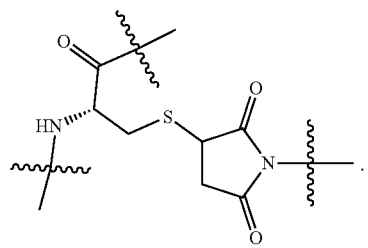 [SMILES: *N[C@@H](CSC1CC(=O)N(*)C1=O)C(*)=O]

In a preferred embodiment of the present disclosure, when D is the cytotoxic drug topoisomerase inhibitor, the cytotoxic drug topoisomerase inhibitor is

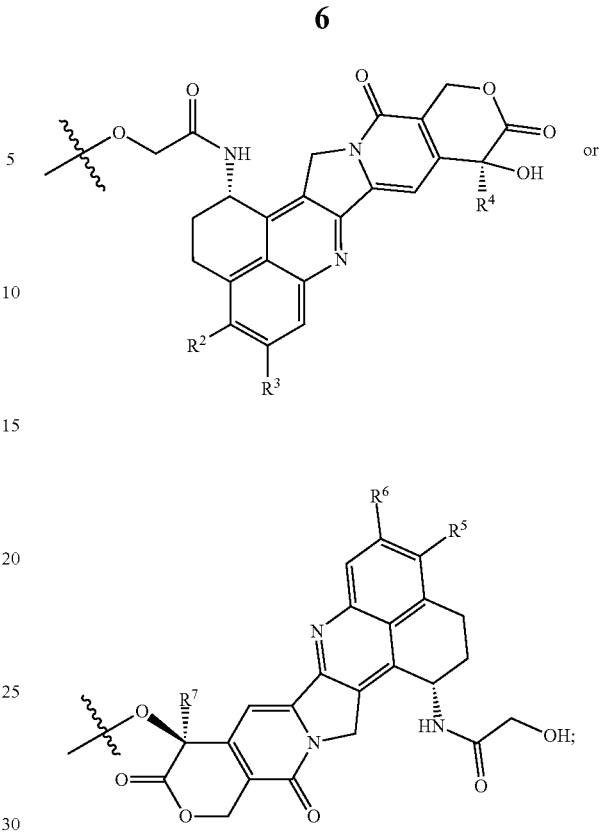

$R^2$ and $R^5$ are each independently H, $C_1$-$C_6$ alkyl or halogen;
$R^3$ and $R^6$ are each independently H, $C_1$-$C_6$ alkyl or halogen;
$R^4$ and $R^7$ are each independently $C_1$-$C_6$ alkyl.

In a preferred embodiment of the present disclosure, when $R^2$ and $R^5$ are each independently $C_1$-$C_6$ alkyl, the $C_1$-$C_6$ alkyl is preferably $C_1$-$C_4$ alkyl, further preferably methyl, ethyl, n-propyl, isopropyl, n-butyl, isobutyl, or tert-butyl, most preferably methyl.

In a preferred embodiment of the present disclosure, when $R^2$ and $R^5$ are each independently halogen, the halogen is preferably fluorine, chlorine, bromine, or iodine, further preferably fluorine.

In a preferred embodiment of the present disclosure, when $R^3$ and $R^6$ are each independently $C_1$-$C_6$ alkyl, the $C_1$-$C_6$ alkyl is preferably $C_1$-$C_4$ alkyl, further preferably methyl, ethyl, n-propyl, isopropyl, n-butyl, isobutyl, or tert-butyl, most preferably methyl.

In a preferred embodiment of the present disclosure, when $R^3$ and $R^6$ are each independently halogen, the halogen is preferably fluorine, chlorine, bromine, or iodine, further preferably fluorine.

In a preferred embodiment of the present disclosure, when $R^4$ and $R^7$ are each independently $C_1$-$C_6$ alkyl, the $C_1$-$C_6$ alkyl is preferably $C_1$-$C_4$ alkyl, further preferably methyl, ethyl, n-propyl, isopropyl, n-butyl, isobutyl, or tert-butyl, most preferably ethyl.

In a preferred embodiment of the present disclosure, $R^2$ and $R^5$ are each independently $C_1$-$C_6$ alkyl.

In a preferred embodiment of the present disclosure, $R^3$ and $R^6$ are each independently halogen.

In a preferred embodiment of the present disclosure, $R^4$ and $R^7$ are ethyl.

In a preferred embodiment of the present disclosure, D is
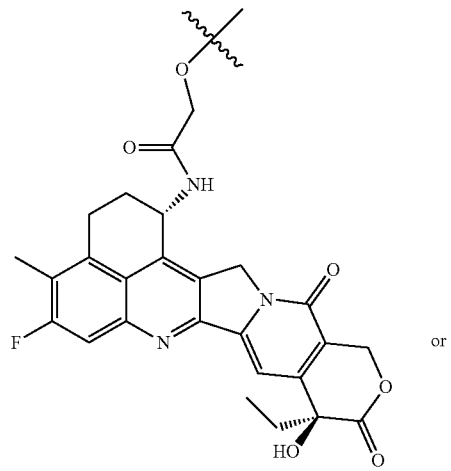
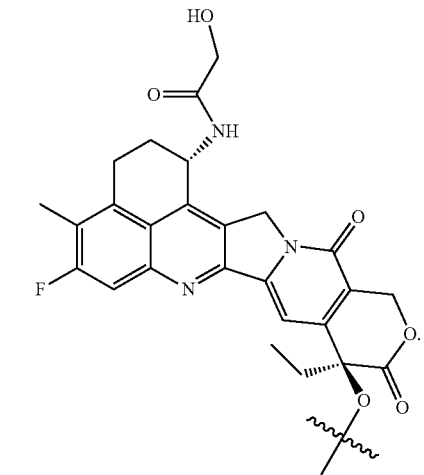
or
In a preferred embodiment of the present disclosure, when D is
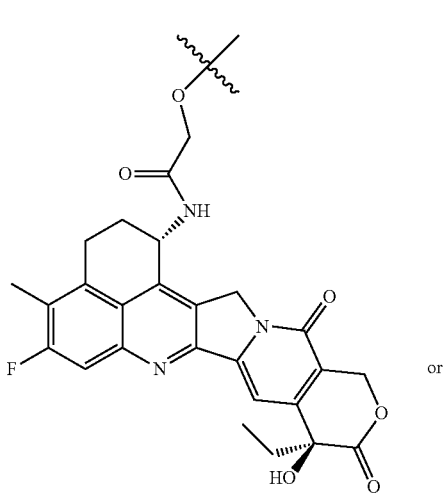
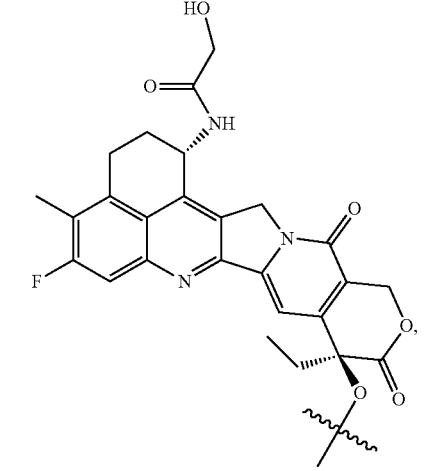
or
the antibody-drug conjugate can be
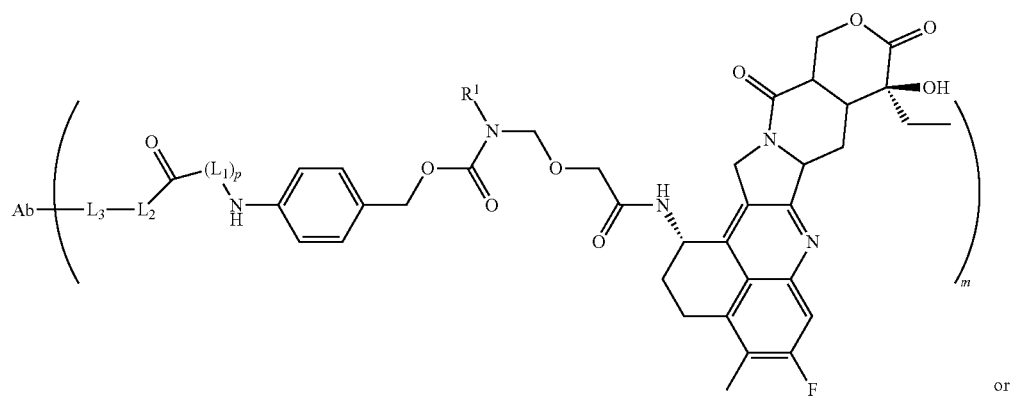
or -continued

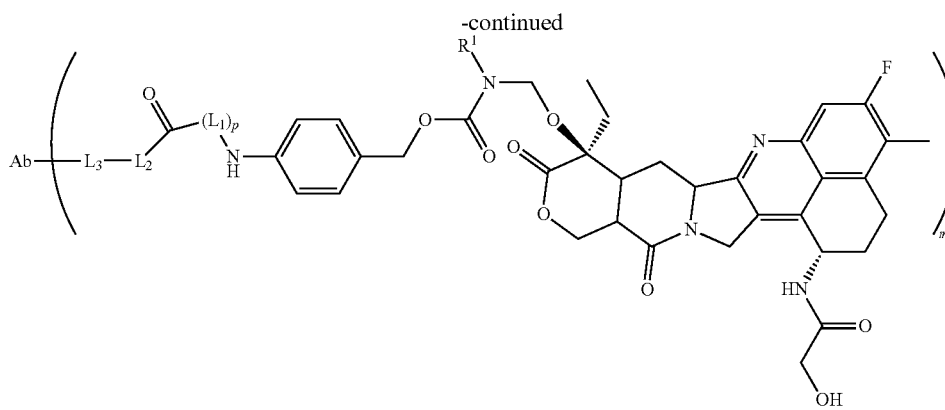

In a preferred embodiment of the present disclosure, when $R^1$ is $C_1$-$C_6$ alkyl substituted by one or more than one —$NR^{1-1}R^{1-2}$, the $C_1$-$C_6$ alkyl is further preferably methyl, ethyl, n-propyl, isopropyl, n-butyl, isobutyl, or tert-butyl, most preferably ethyl.

In a preferred embodiment of the present disclosure, when $R^1$ is $C_1$-$C_6$ alkyl substituted by more than one —$NR^{1-1}R^{1-2}$, the "more than one" is preferably two or three.

In a preferred embodiment of the present disclosure, when $R^{1-1}$ and $R^{1-2}$ are each independently $C_1$-$C_6$ alkyl, the $C_1$-$C_6$ alkyl is preferably methyl, ethyl, n-propyl, isopropyl, n-butyl, isobutyl, or tert-butyl, most preferably methyl.

In a preferred embodiment of the present disclosure, when $R^1$ is $C_1$-$C_6$ alkyl substituted by one or more than one —$NR^{1-1}R^{1-2}$, the —$NR^{1-1}R^{1-2}$ is preferably —$N(CH_3)_2$.

In a preferred embodiment of the present disclosure, when $R^1$ is $C_1$-$C_6$ alkyl substituted by one —$NR^{1-1}R^{1-2}$, the $C_1$-$C_6$ alkyl substituted by one —$NR^{1-1}R^{1-2}$ is

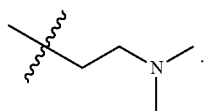 [SMILES: *CCN(C)C]

In a preferred embodiment of the present disclosure, when $R^1$ is $C_1$-$C_6$ alkyl substituted by one or more than one $R^{1-3}$ $S(O)_2$—, the $C_1$-$C_6$ alkyl is preferably $C_1$-$C_4$ alkyl, further preferably methyl, ethyl, n-propyl, isopropyl, n-butyl, isobutyl, or tert-butyl, most preferably ethyl.

In a preferred embodiment of the present disclosure, when $R^1$ is $C_1$-$C_6$ alkyl substituted by more than one $R^{1-3}$ $S(O)_2$—, the "more than one" is preferably two or three.

In a preferred embodiment of the present disclosure, when $R^{1-3}$ is $C_1$-$C_6$ alkyl, the $C_1$-$C_6$ alkyl is preferably methyl, ethyl, n-propyl, isopropyl, n-butyl, isobutyl, or tert-butyl, most preferably methyl.

In a preferred embodiment of the present disclosure, when $R^1$ is $C_1$-$C_6$ alkyl substituted by one $R^{1-3}S(O)_2$—, the $C_1$-$C_6$ alkyl substituted by one $R^{1-3}S(O)_2$— is

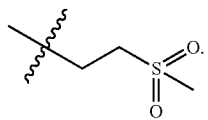 [SMILES: *CCS(C)(=O)=O]

In a preferred embodiment of the present disclosure, when $R^1$ is $C_1$-$C_6$ alkyl, the $C_1$-$C_6$ alkyl is preferably methyl, ethyl, n-propyl, isopropyl, n-butyl, isobutyl, or tert-butyl, most preferably methyl.

In a preferred embodiment of the present disclosure, m is an integer (such as 2, 3, 4, 5, 6, 7, or 8) or non-integer, preferably 4 to 8, more preferably 6 to 8, further preferably 7 to 8, still more preferably 7.4 to 7.85, such as 7.49, 7.56, 7.59, 7.60, 7.63, 7.65, 7.67, 7.72, 7.78, 7.81, 7.82, or 7.83.

In a preferred embodiment of the present disclosure, $L_1$ is preferably one or more than one of the phenylalanine residue, alanine residue, glycine residue, isoleucine residue, leucine residue, proline residue, and valine residue; more preferably one or more than one of the phenylalanine residue, alanine residue, glycine residue, and valine residue; further preferably the valine residue and/or the alanine residue; the "more than one" is preferably two or three; p is preferably 2.

In one preferred embodiment of the present disclosure, $(L_1)_p$ is further preferably

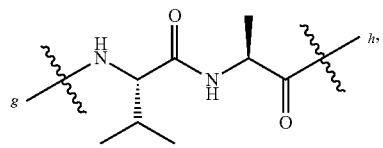 [SMILES: *N[C@H](C(=O)N[C@@H](C)C(*)=O)C(C)C]

wherein the g-terminal is connected to the c-terminal of $L_2$ through a carbonyl group.

In a preferred embodiment of the present disclosure, n is preferably 8 to 12, such as 8, 9, 10, 11, and 12, further such as 8 or 12.

In a preferred embodiment of the present disclosure, when $R^{1-1}$, $R^{1-2}$, and $R^{1-3}$ are each independently $C_1$-$C_6$ alkyl, the $C_1$-$C_6$ alkyl is preferably $C_1$-$C_4$ alkyl, further preferably methyl, ethyl, n-propyl, isopropyl, n-butyl, isobutyl, or tert-butyl, most preferably methyl.

In a preferred embodiment of the present disclosure, $R^1$ is preferably $C_1$-$C_6$ alkyl substituted by one or more than one —$NR^{1-1}R^{1-2}$, $C_1$-$C_6$ alkyl substituted by one or more than one $R^{1-3}$ $S(O)_2$—, $C_1$-$C_6$ alkyl, or $C_3$-$C_{10}$ cycloalkyl; $R^1$ is more preferably $C_1$-$C_6$ alkyl substituted by one or more than one —$NR^{1-1}R^{1-2}$, $C_1$-$C_6$ alkyl substituted by one or more than one $R^{1-3}S(O)_2$—, or $C_1$-$C_6$ alkyl; further preferably $C_1$-$C_6$ alkyl substituted by one or more than one —$NR^{1-1}R^{1-2}$, or $C_1$-$C_6$ alkyl substituted by one or more than one $R^{1-3}S(O)_2$—; most preferably $C_1$-$C_6$ alkyl substituted by one or more than one $R^{1-3}S(O)_2$—.

In a preferred embodiment of the present disclosure, the compound of formula I is any one of the following schemes:

scheme I:

Ab is HER3 antibody A or the variant of HER3 antibody A, and the amino acid sequence of the light chain in the variant of HER3 antibody A is preferably shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S, for example, having site mutations of E233P, L234V, and L235A (i.e., sequence SEQ ID NO: 3), or having site mutations of L234F, L235E, and P331S (i.e., sequence SEQ ID NO: 4);

D is

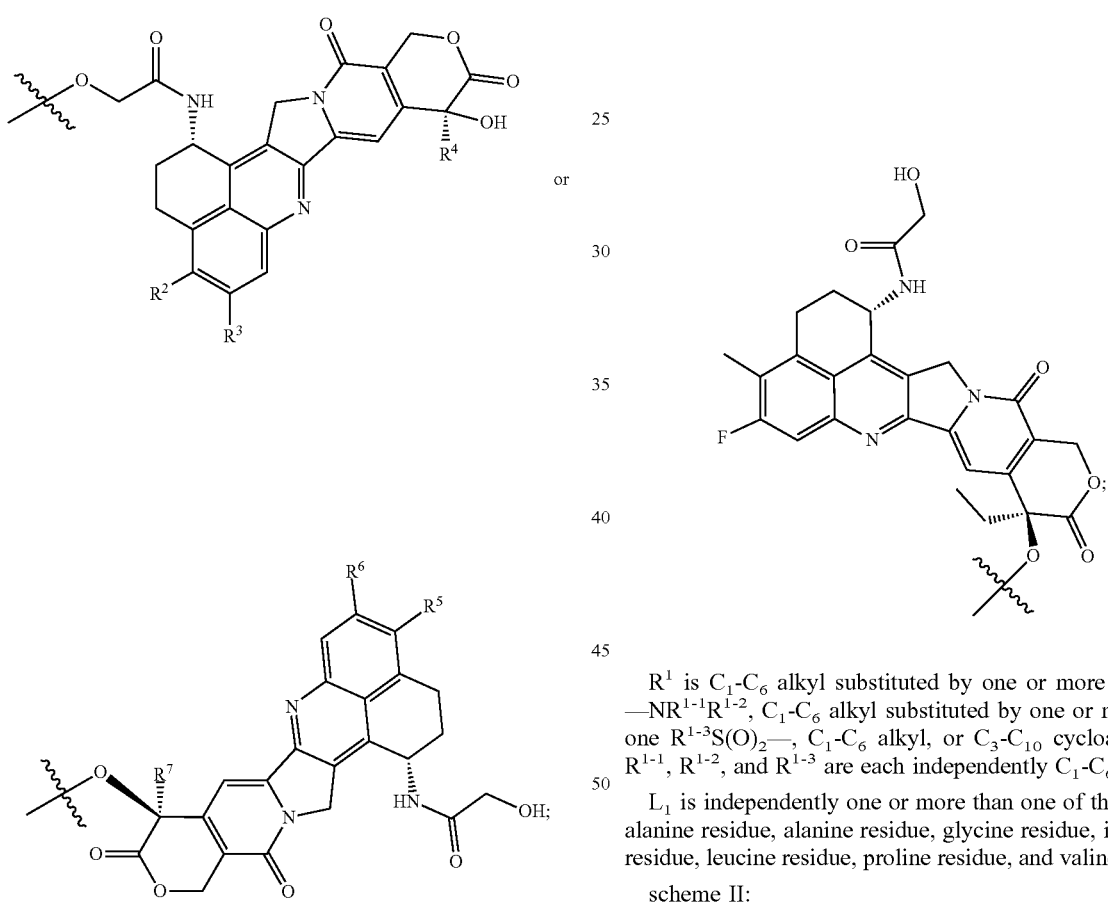

$R^2$ and $R^5$ are each independently H, $C_1$-$C_6$ alkyl or halogen; $R^3$ and $R^6$ are each independently H, $C_1$-$C_6$ alkyl or halogen; $R^4$ and $R^7$ are each independently $C_1$-$C_6$ alkyl; D is preferably

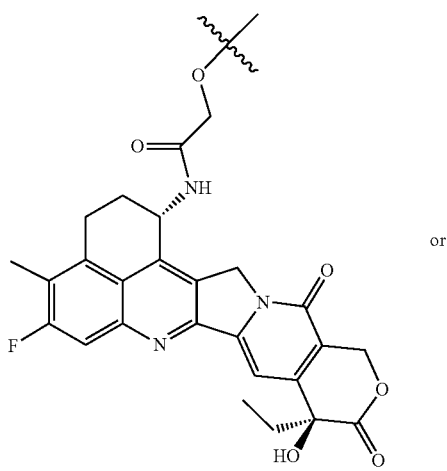

$R^1$ is $C_1$-$C_6$ alkyl substituted by one or more than one —$NR^{1-1}R^{1-2}$, $C_1$-$C_6$ alkyl substituted by one or more than one $R^{1-3}S(O)_2$—, $C_1$-$C_6$ alkyl, or $C_3$-$C_{10}$ cycloalkyl; the $R^{1-1}$, $R^{1-2}$, and $R^{1-3}$ are each independently $C_1$-$C_6$ alkyl;

$L_1$ is independently one or more than one of the phenylalanine residue, alanine residue, glycine residue, isoleucine residue, leucine residue, proline residue, and valine residue;

scheme II:

Ab is HER3 antibody A or the variant of HER3 antibody A, and the amino acid sequence of the light chain in the variant of HER3 antibody A is preferably shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S, for example, having site mutations of E233P, L234V, and L235A (i.e., sequence SEQ ID NO: 3), or having site mutations of L234F, L235E, and P331S (i.e., sequence SEQ ID NO: 4);

D is

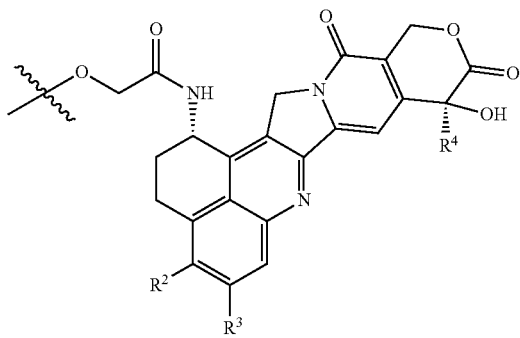

or

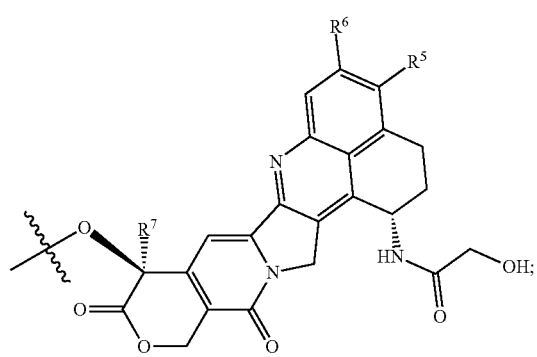

$R^2$ and $R^5$ are each independently $C_1$-$C_6$ alkyl; $R^3$ and $R^6$ are each independently halogen; D is preferably

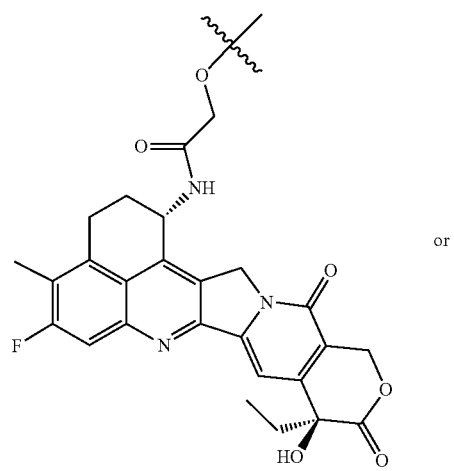

or

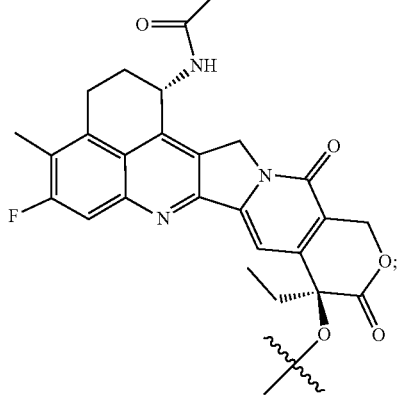

$R^1$ is $C_1$-$C_6$ alkyl substituted by one or more than one —$NR^{1-1}R^{1-2}$, $C_1$-$C_6$ alkyl substituted by one or more than one $R^{1-3}$ $S(O)_2$—, or $C_1$-$C_6$ alkyl;

scheme III:

Ab is HER3 antibody A or the variant of HER3 antibody A, and the amino acid sequence of the light chain in the variant of HER3 antibody A is preferably shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S, for example, having site mutations of E233P, L234V, and L235A (i.e., sequence SEQ ID NO: 3), or having site mutations of L234F, L235E, and P331S (i.e., sequence SEQ ID NO: 4);

D is

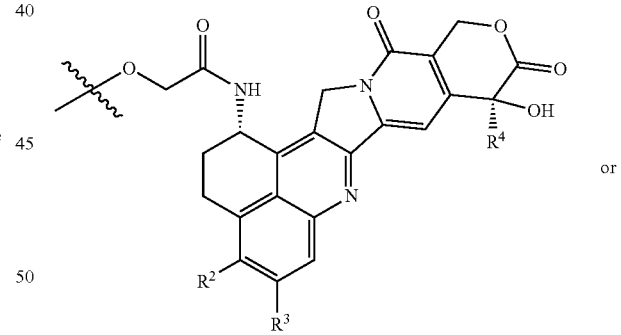

or $R^2$ and $R^5$ are each independently $C_1$-$C_6$ alkyl; $R^3$ and $R^6$ are each independently halogen; D is preferably

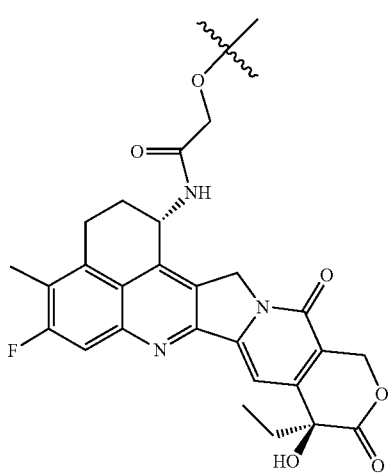

or

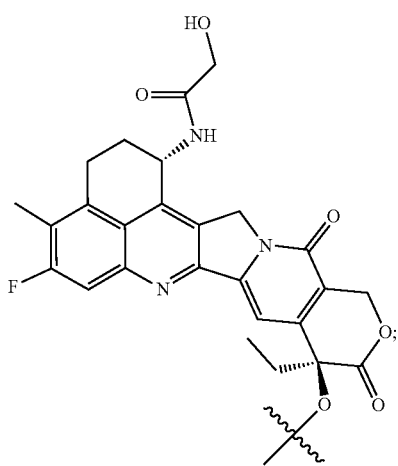

m is 7 to 8;

$R^1$ is $C_1$-$C_6$ alkyl substituted by one or more than one —$NR^{1-1}R^{1-2}$, $C_1$-$C_6$ alkyl substituted by one or more than one $R^{1-3}$ S(O)$_2$—, or $C_1$-$C_6$ alkyl;

$L_1$ is independently the valine residue and/or the alanine residue;

scheme IV:

Ab is HER3 antibody A or the variant of HER3 antibody A, and the amino acid sequence of the light chain in the variant of HER3 antibody A is preferably shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S, for example, having site mutations of E233P, L234V, and L235A (i.e., sequence SEQ ID NO: 3), or having site mutations of L234F, L235E, and P331S (i.e., sequence SEQ ID NO: 4);

D is

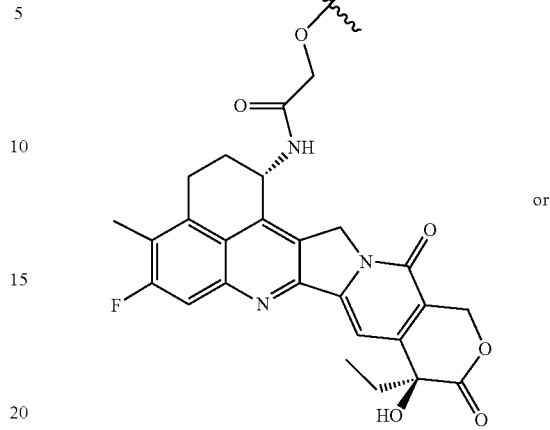

or

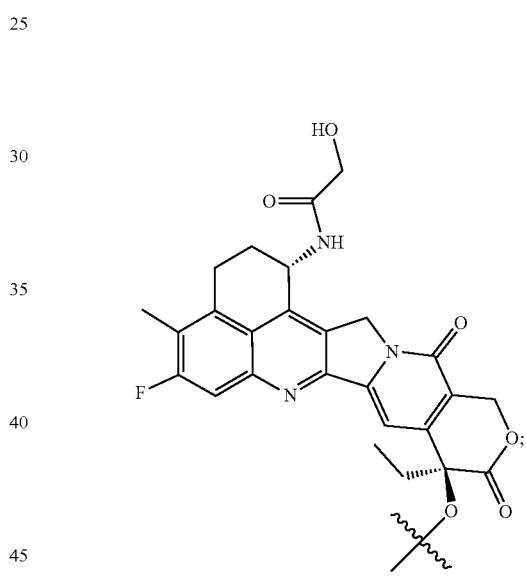

$R^1$ is $C_1$-$C_6$ alkyl substituted by one or more than one —$NR^{1-1}R^{1-2}$, $C_1$-$C_6$ alkyl substituted by one or more than one $R^{1-3}$ S(O)$_2$—, or $C_1$-$C_6$ alkyl;

scheme V:

Ab is HER3 antibody A or the variant of HER3 antibody A, and the amino acid sequence of the light chain in the variant of HER3 antibody A is preferably shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S, for example, having site mutations of E233P, L234V, and L235A (i.e., sequence SEQ ID NO: 3), or having site mutations of L234F, L235E, and P331S (i.e., sequence SEQ ID NO: 4);

D is
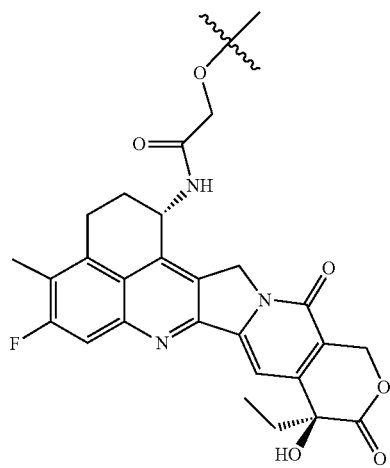
or
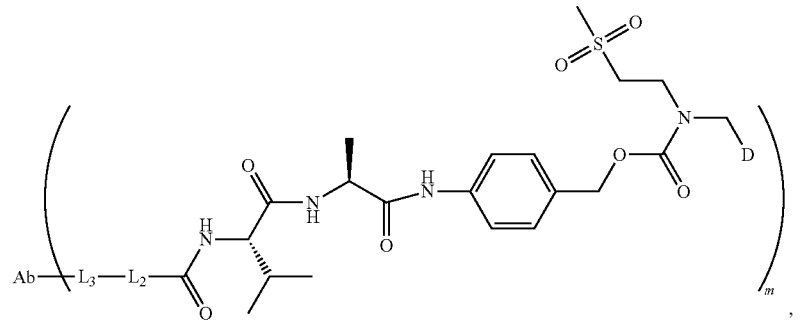
-continued
m is 7 to 8;
$R^1$ is $C_1$-$C_6$ alkyl substituted by one or more than one —$NR^{1-1}R^{1-2}$, $C_1$-$C_6$ alkyl substituted by one or more than one R'S(O)$_2$—, or $C_1$-$C_6$ alkyl;
$L_1$ is independently valine residue and/or alanine residue.
In a preferred embodiment of the present disclosure, the antibody-drug conjugate is preferably
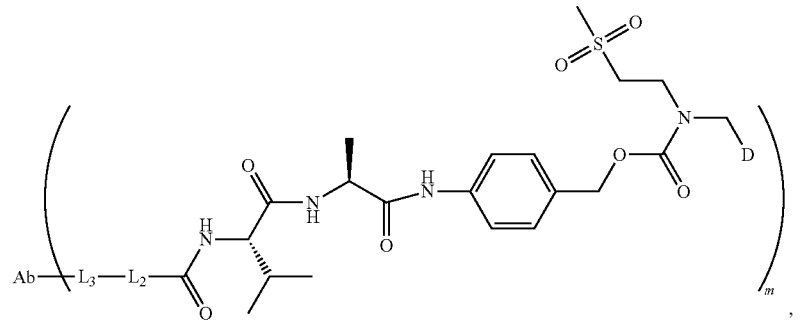
,
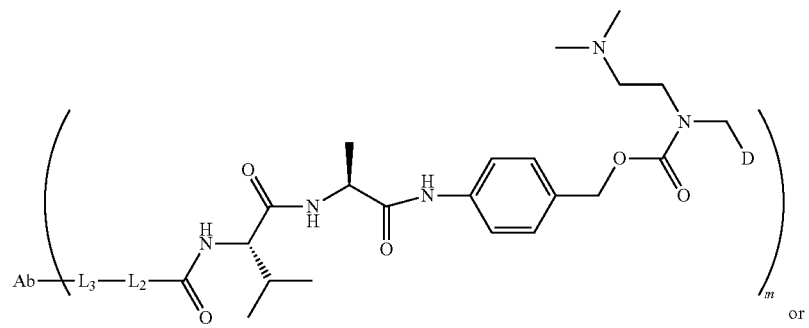
or
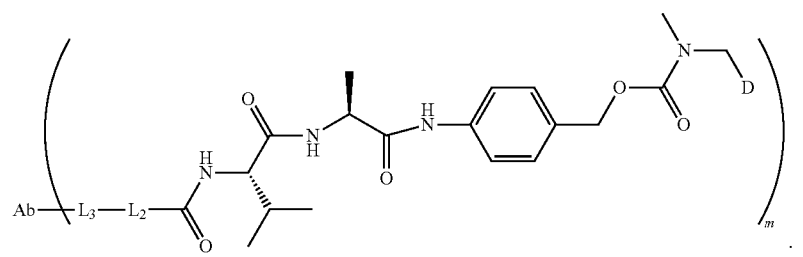
.

In a preferred embodiment of the present disclosure, $L_2$ is preferably

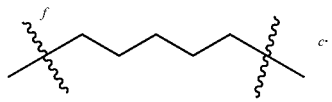 [SMILES: *CCCCC*]

In a preferred embodiment of the present disclosure, the antibody in the antibody-drug conjugate is preferably HER3 antibody A or the variant of HER3 antibody A; the amino acid sequence of the light chain in the variant of HER3 antibody A is shown in SEQ ID NO: 1, the amino acid sequence of the heavy chain is selected from SEQ ID NO: 3 or SEQ ID NO: 4; D is

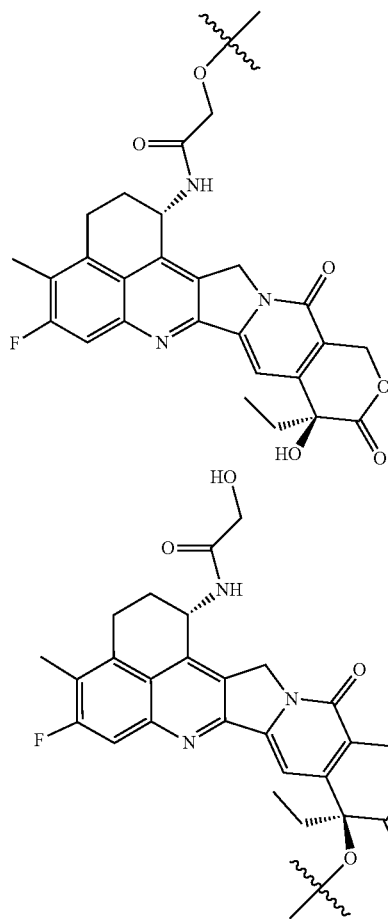

$L_1$ is valine residue and/or alanine residue; p is 2; $(L_1)p$ is preferably

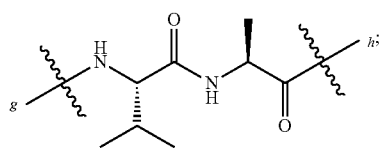 [SMILES: *N[C@H](C(=O)N[C@@H](C)C(*)=O)C(C)C]

$R^1$ is $C_1$-$C_6$ alkyl substituted with one or more than one —$NR^{1-1}R^{1-2}$, $C_1$-$C_6$ alkyl substituted with one or more than one $R^{1-3}S(O)_2$—, or $C_1$-$C_6$ alkyl, preferably $C_1$-$C_6$ alkyl substituted with one or more than one —$NR^{1-1}R^{1-2}$ or $C_1$-$C_6$ alkyl substituted with one or more than one $R^{1-3}S(O)_2$—, further preferably $C_1$-$C_6$ alkyl substituted with one or more than one $R^{1-3}S(O)_2$—; $R^{1-1}$, $R^{1-2}$, and $R^{1-3}$ are independently $C_1$-$C_4$ alkyl, preferably methyl; the $C_1$-$C_6$ alkyl substituted with one or more than one —$NR^{1-1}R^{1-2}$ is preferably

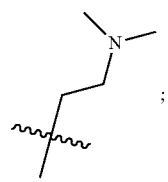 [SMILES: *CCN(C)C]

the $C_1$-$C_6$ alkyl substituted with one or more than one $R^{1-3}S(O)_2$— is preferably

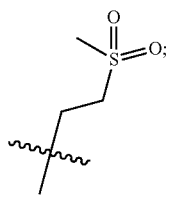 [SMILES: *CCS(C)(=O)=O]

$L_2$ is

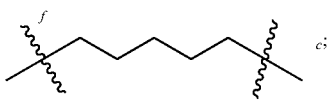 [SMILES: *CCCCC*]

$L_3$ is

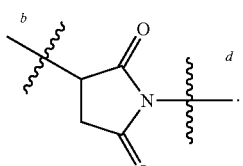

In a preferred embodiment of the present disclosure, the antibody-drug conjugate is preferably any one of the following compounds:

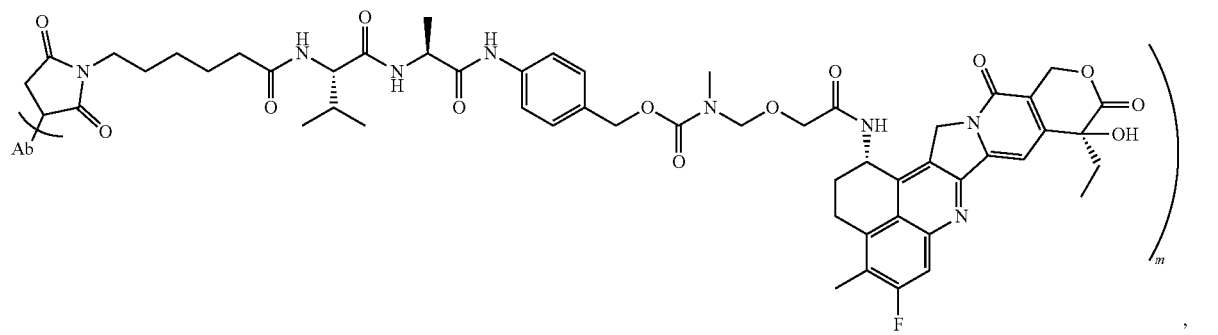
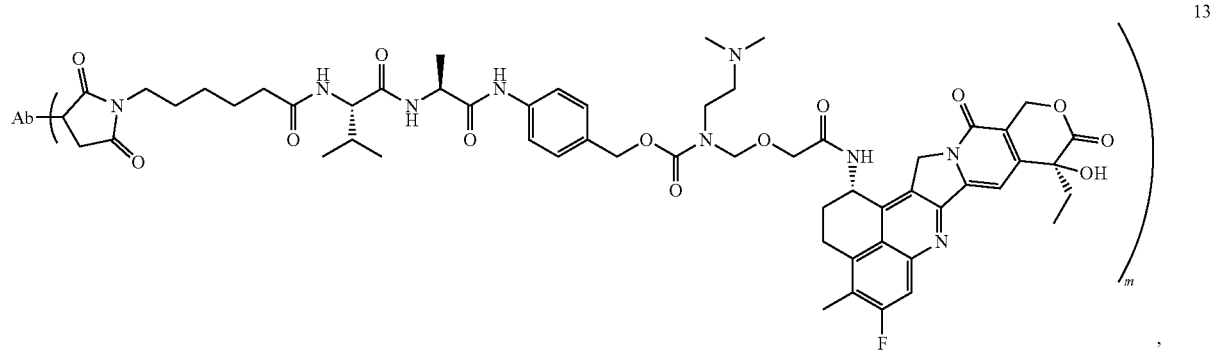
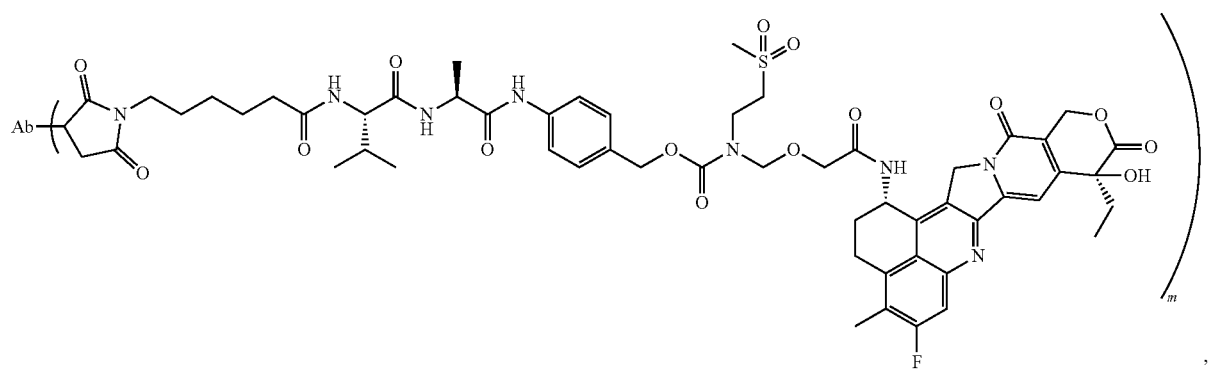
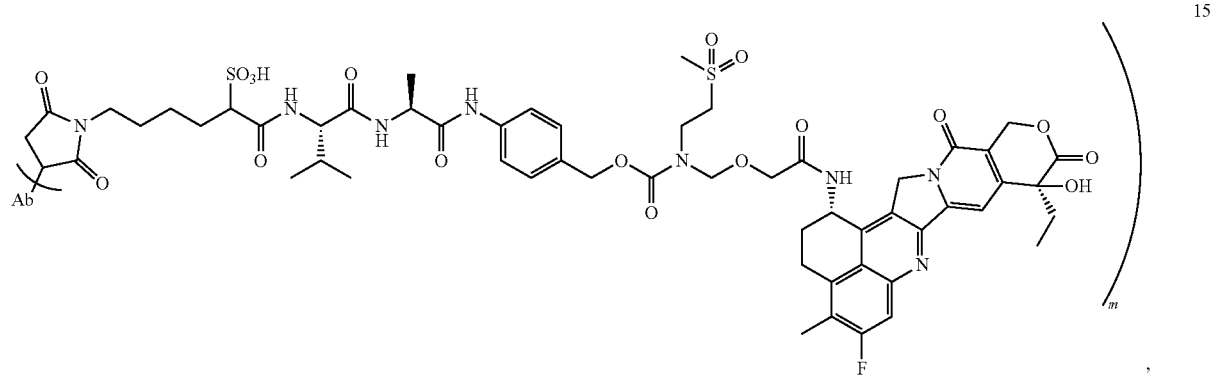

-continued
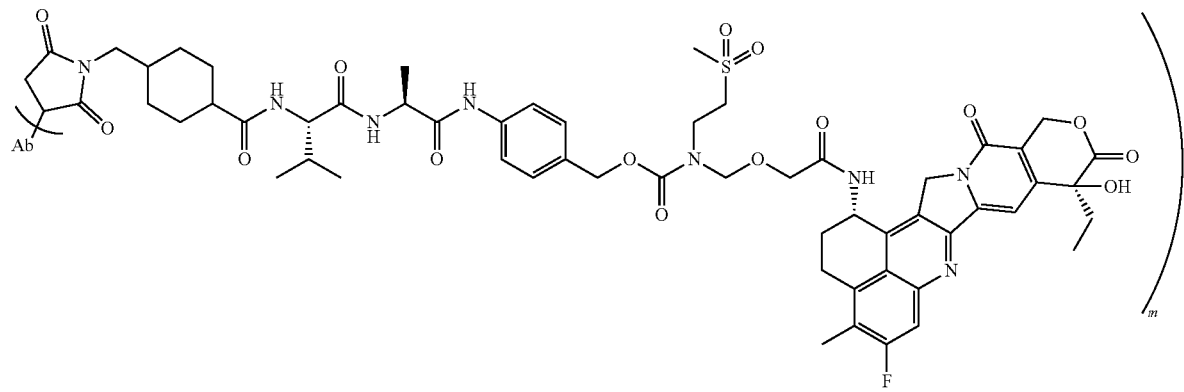
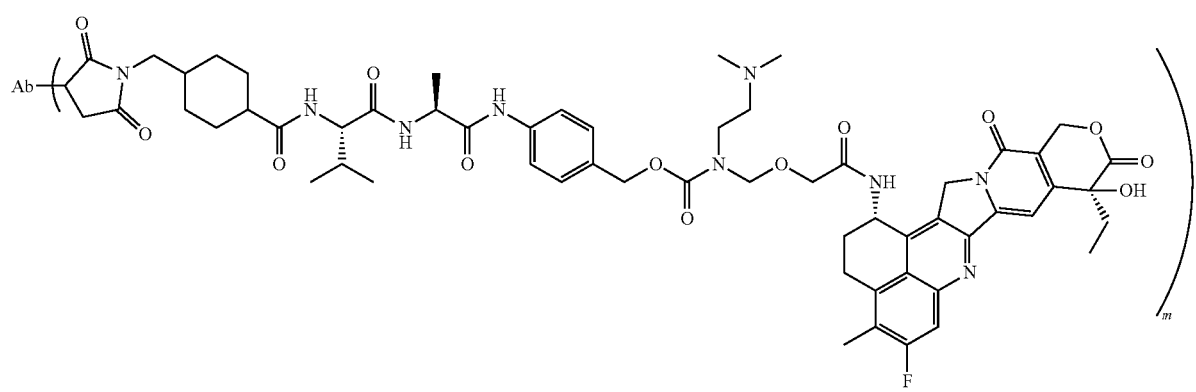
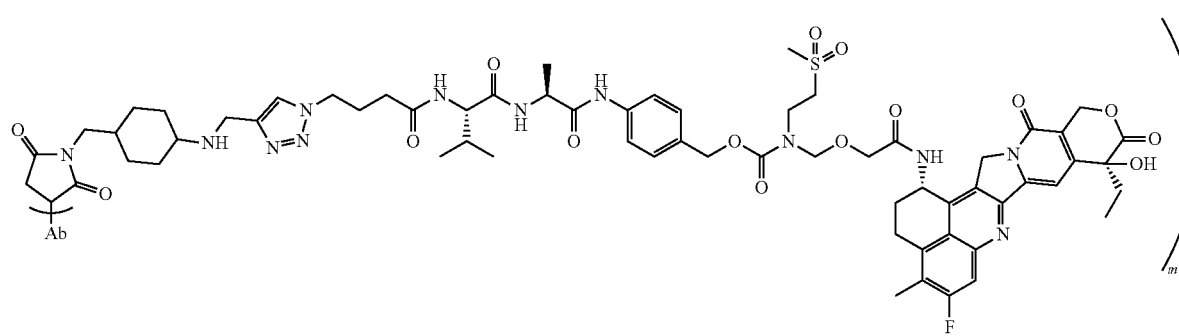
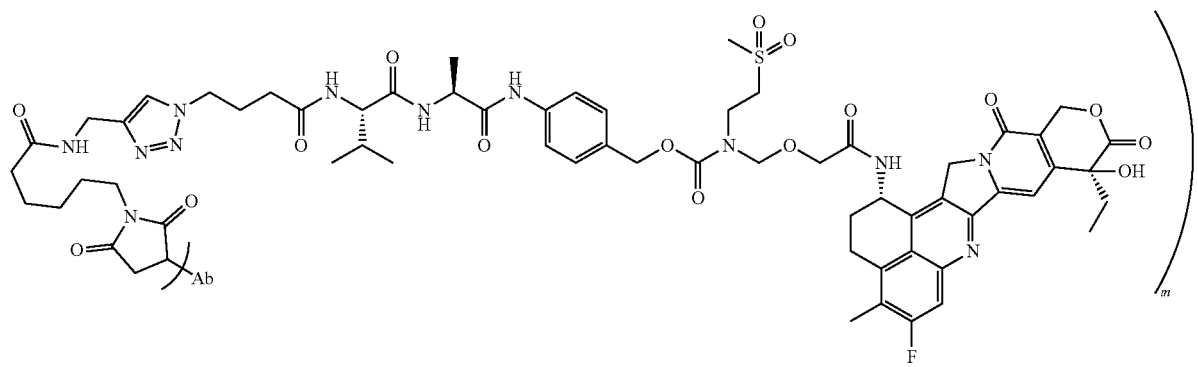

-continued
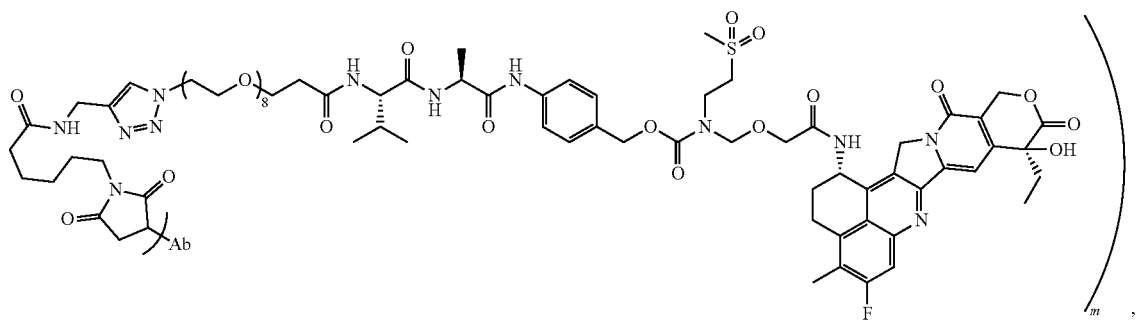
20
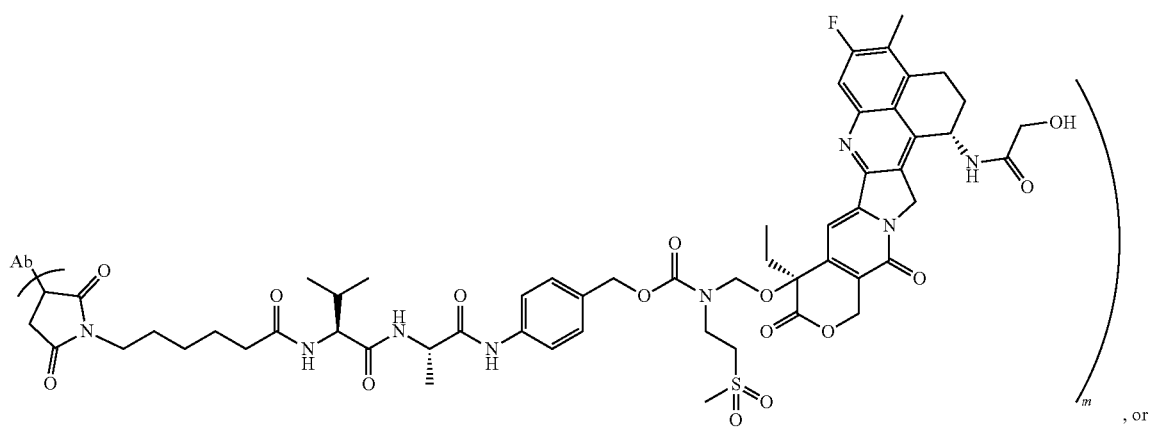
21
, or
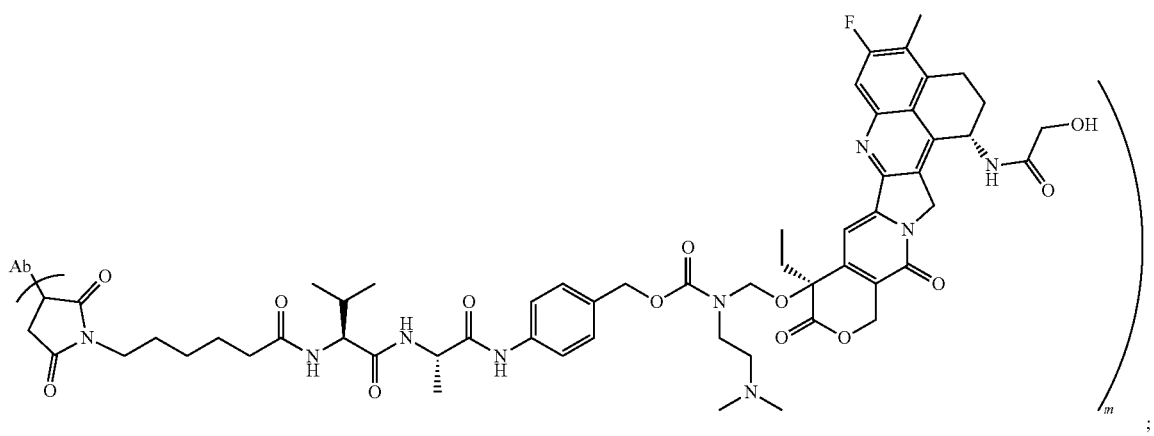
22
;
wherein Ab is HER3 antibody A or the variant of HER3 antibody A, and m is 7.49, 7.56, 7.59, 7.60, 7.63, 7.65, 7.67, 7.72, 7.78, 7.81, or 7.83; the amino acid sequence of the light chain in the variant of HER3 antibody A is preferably shown in SEQ ID NO: 1, the amino acid sequence of the heavy chain is preferably selected from SEQ ID NO: 3 or SEQ ID NO: 4.

In a preferred embodiment of the present disclosure, the antibody-drug conjugate is preferably any one of the following compounds:
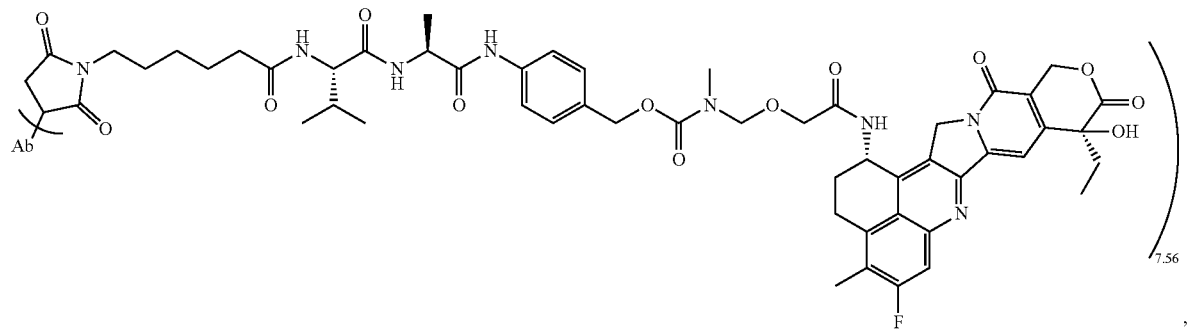
12
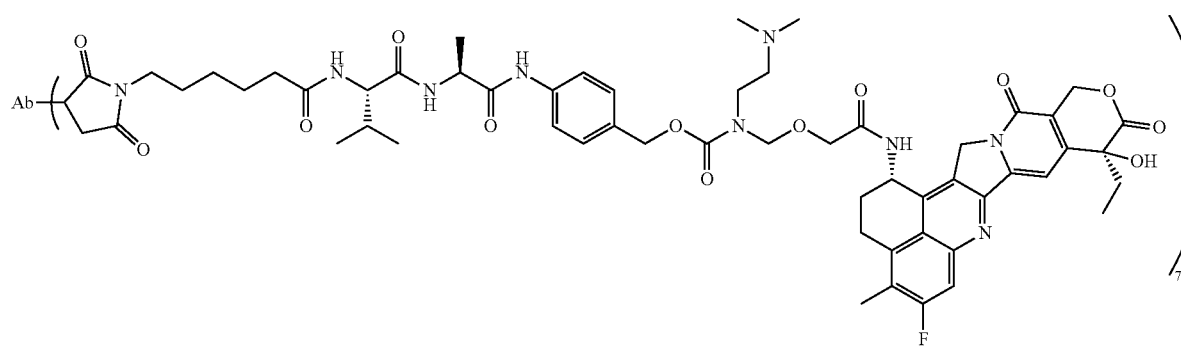
13
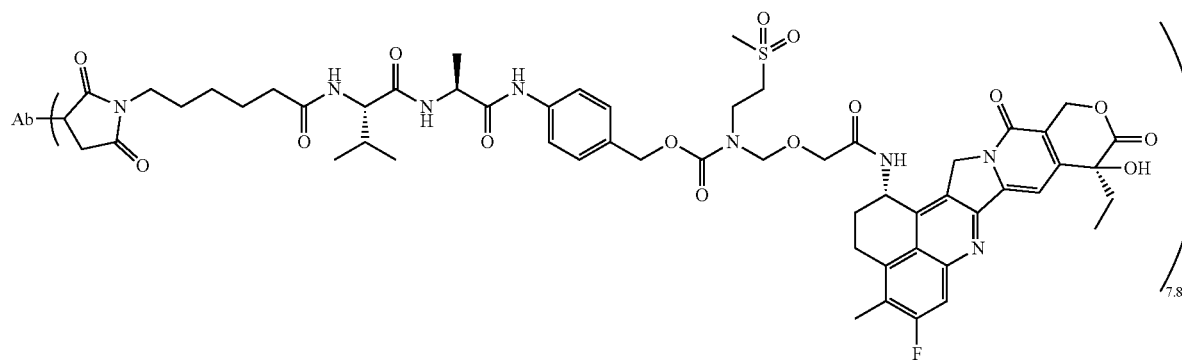
14
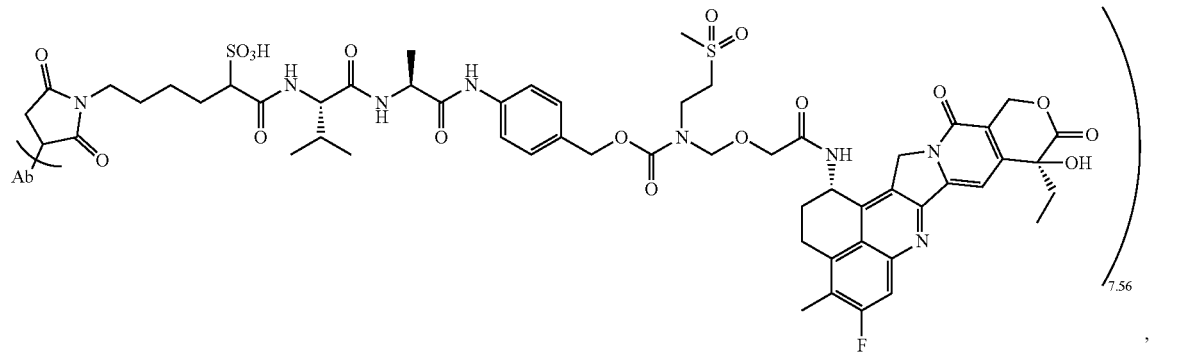
15

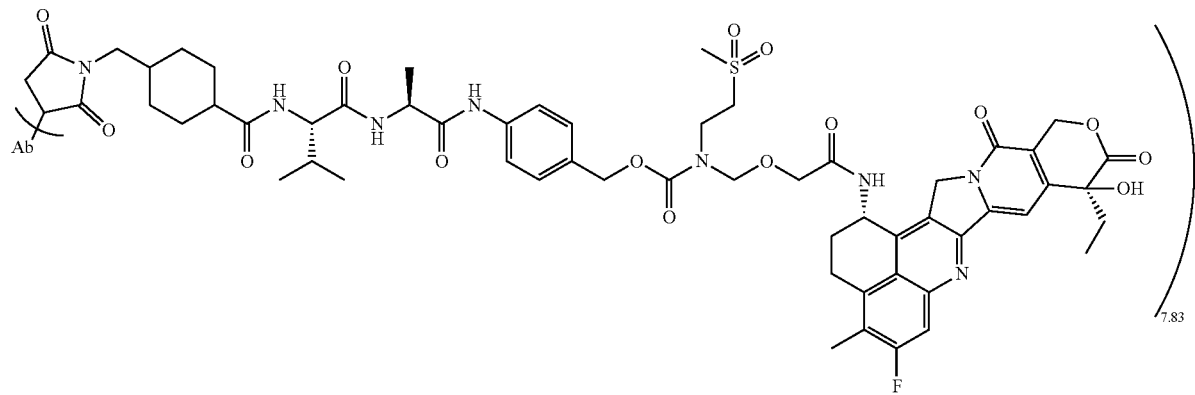
16
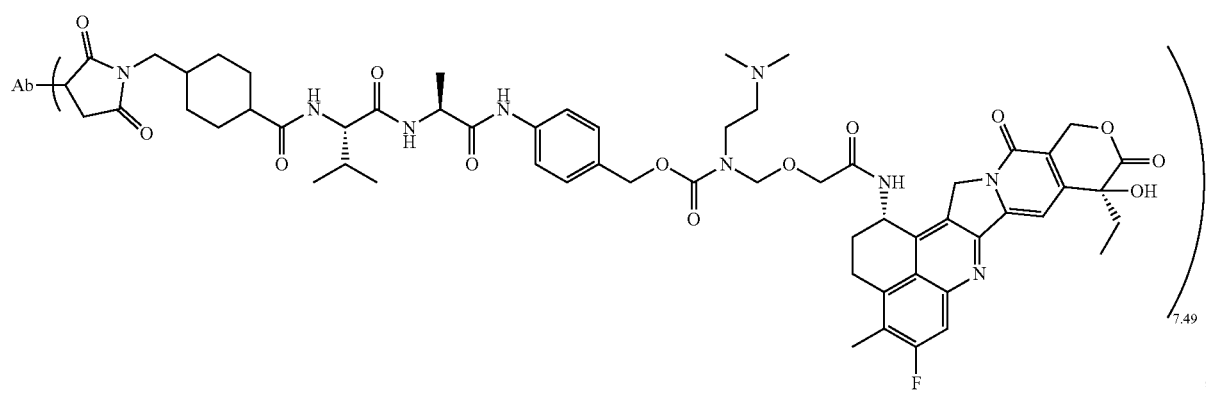
17
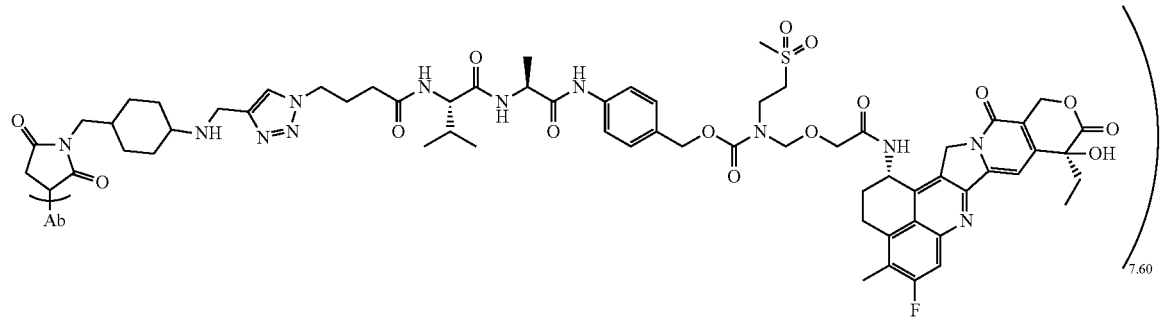
18
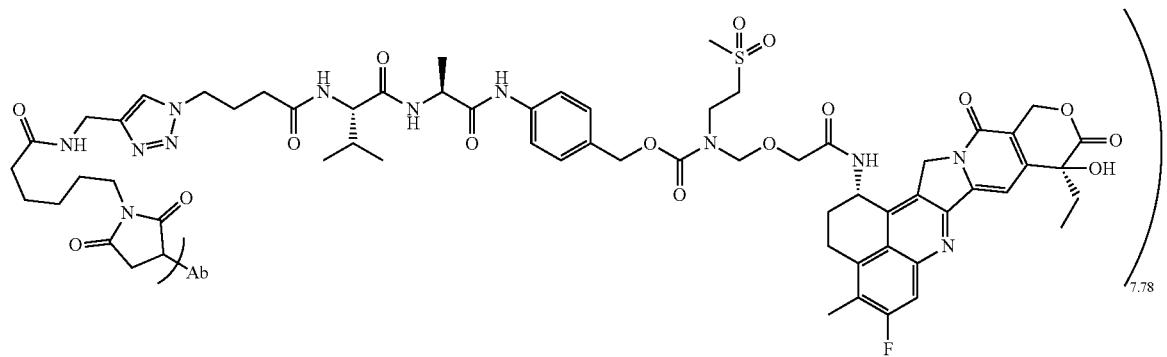
19

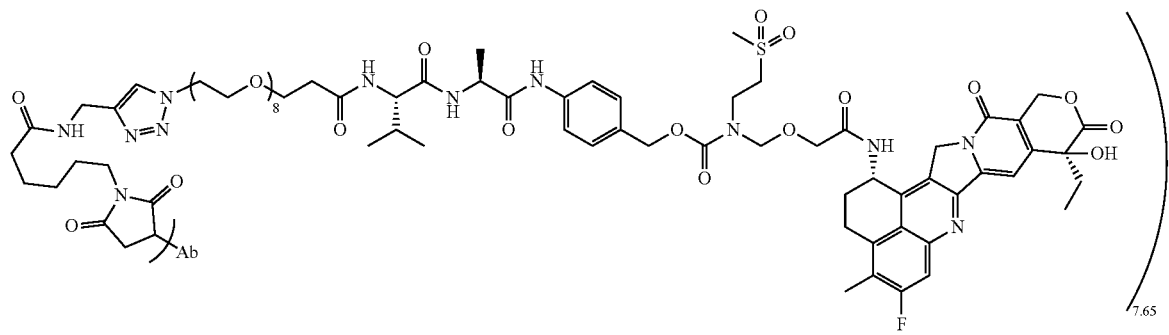
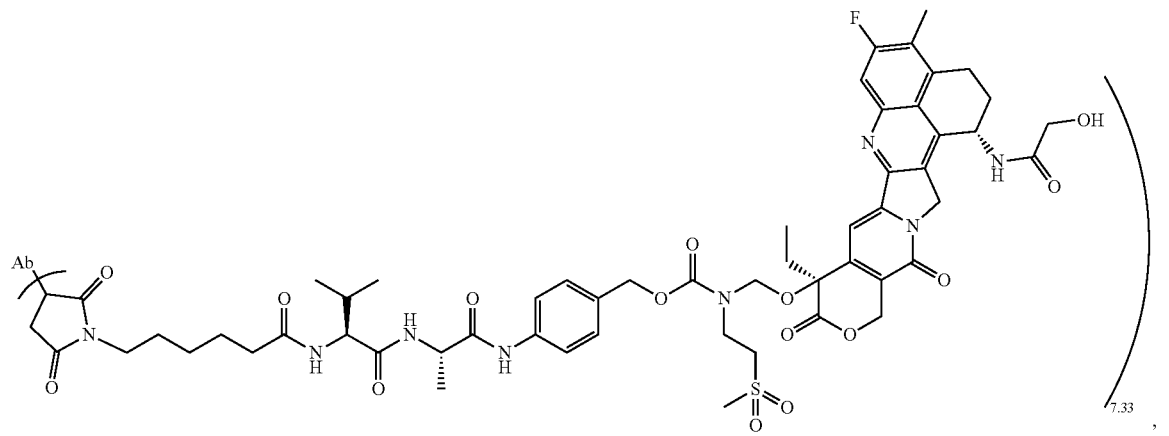
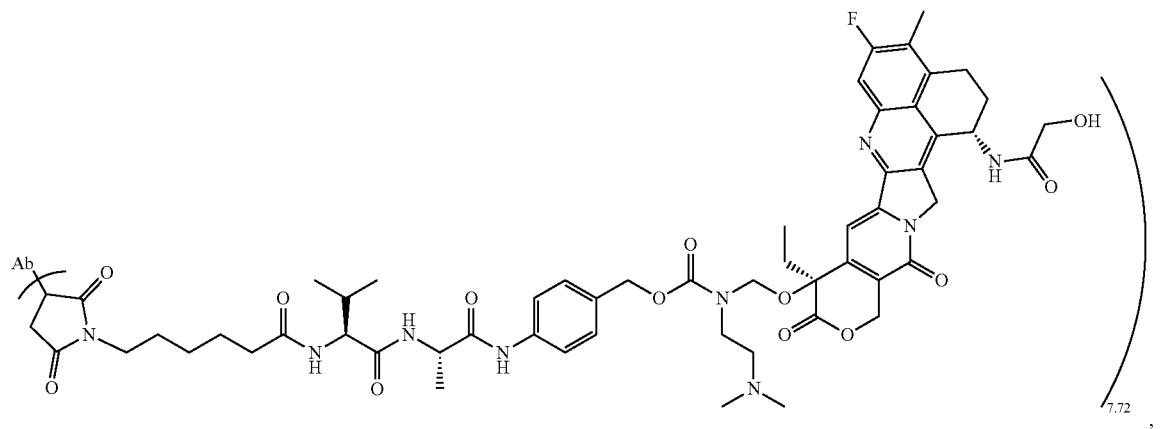
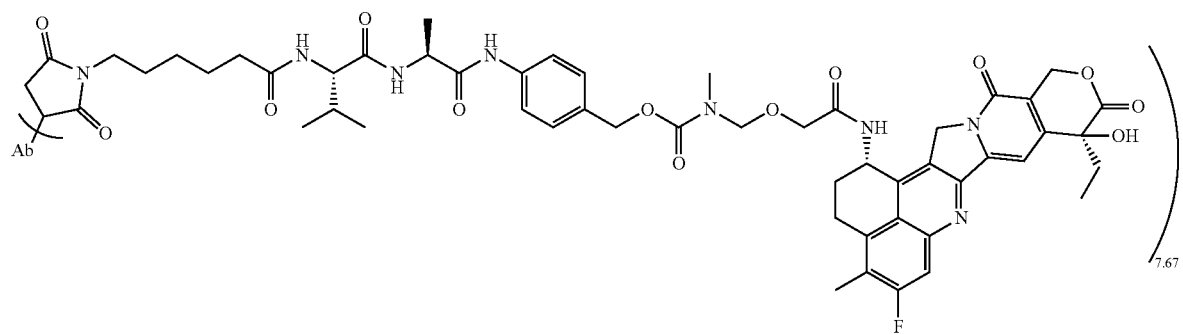

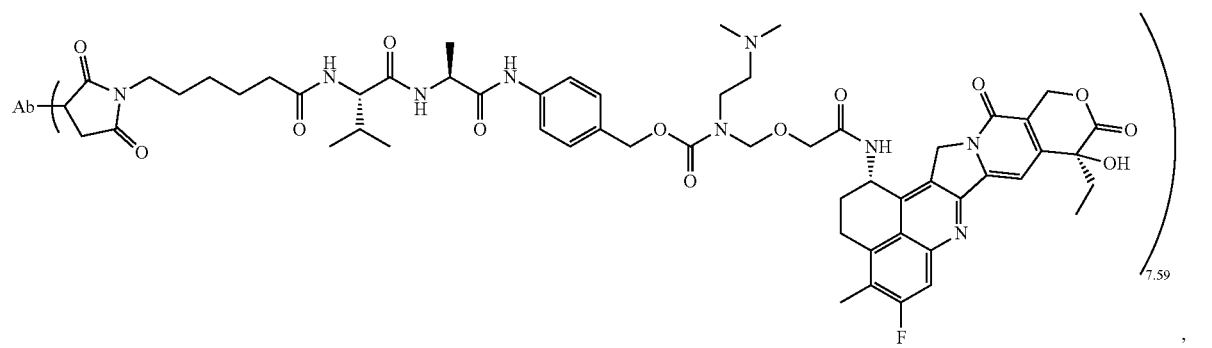
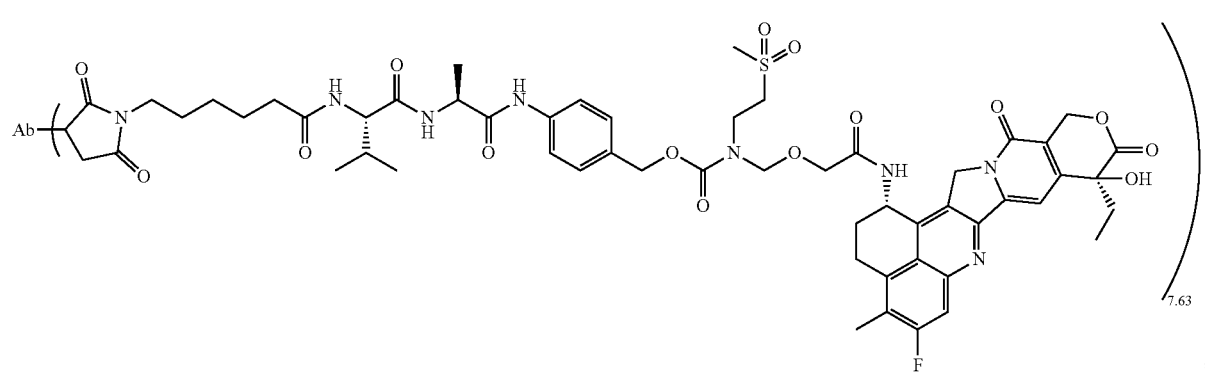
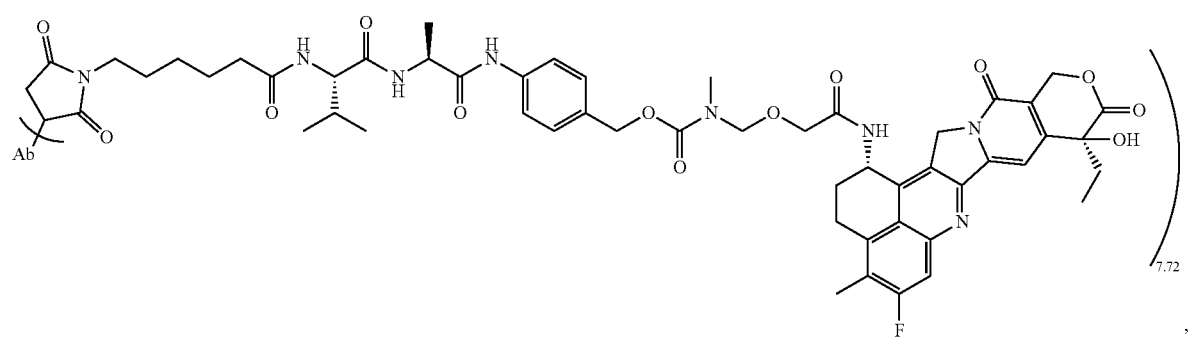
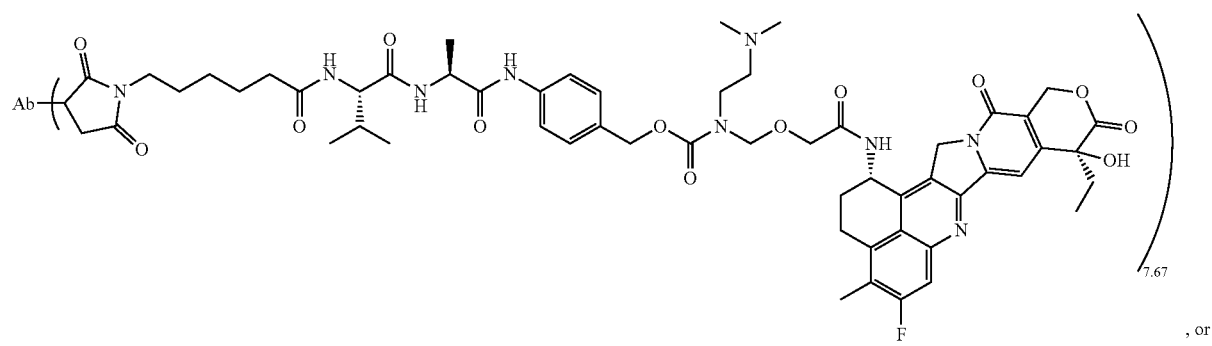
, or

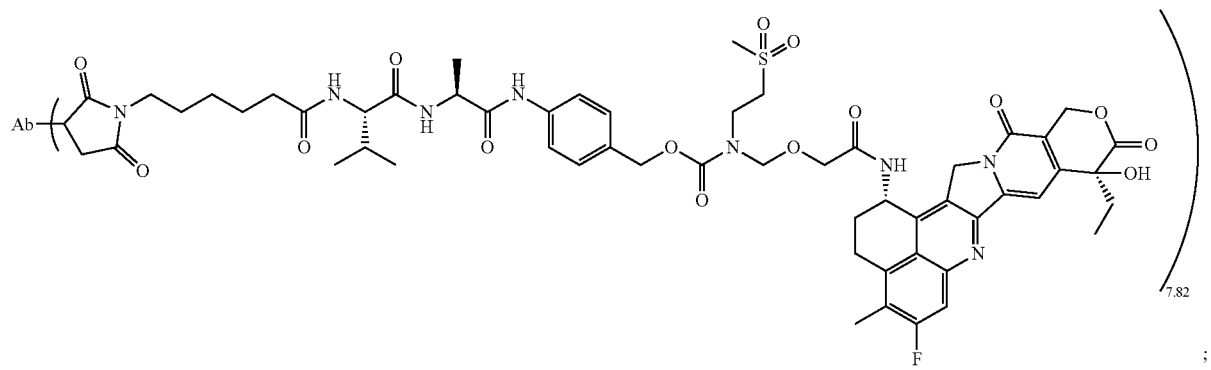

wherein Ab is HER3 antibody A or the variant of HER3 antibody A; the amino acid sequence of the light chain in the variant of HER3 antibody A is preferably shown in SEQ ID NO: 1, the amino acid sequence of the heavy chain is preferably selected from SEQ ID NO: 3 or SEQ ID NO: 4.

In a preferred embodiment of the present disclosure, the antibody-drug conjugate is preferably any one of the following compounds:

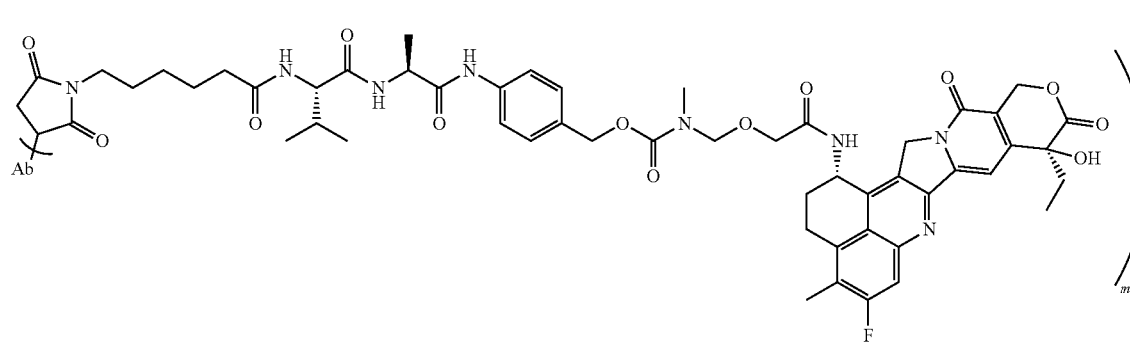

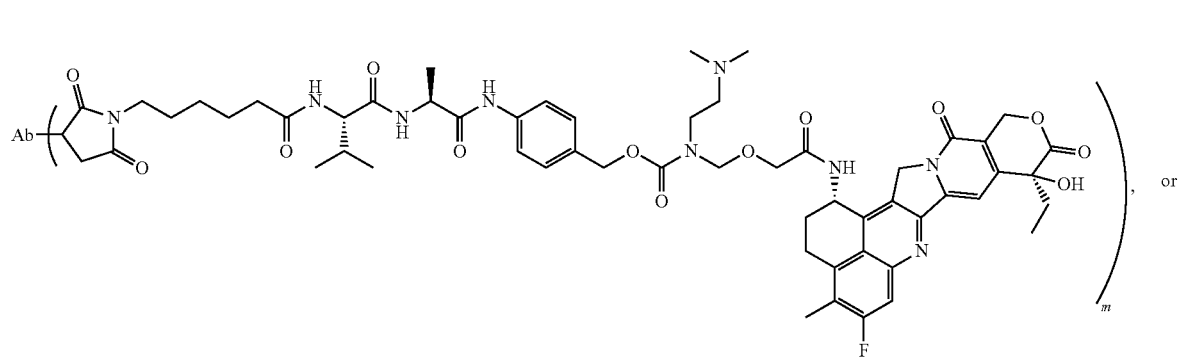

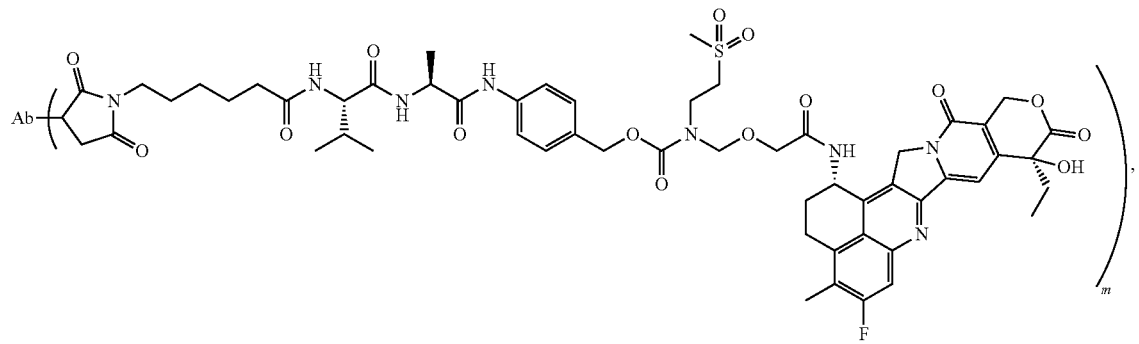

14 wherein Ab is HER3 antibody A or the variant of HER3 antibody A, and m is 7.56, 7.59, 7.63, 7.67, 7.72, 7.81, or 7.83; the amino acid sequence of the light chain in the variant of HER3 antibody A is preferably shown in SEQ ID NO: 1, the amino acid sequence of the heavy chain is preferably selected from SEQ ID NO: 3 or SEQ ID NO: 4.

In a preferred embodiment of the present disclosure, the antibody-drug conjugate is preferably any one of the following compounds:

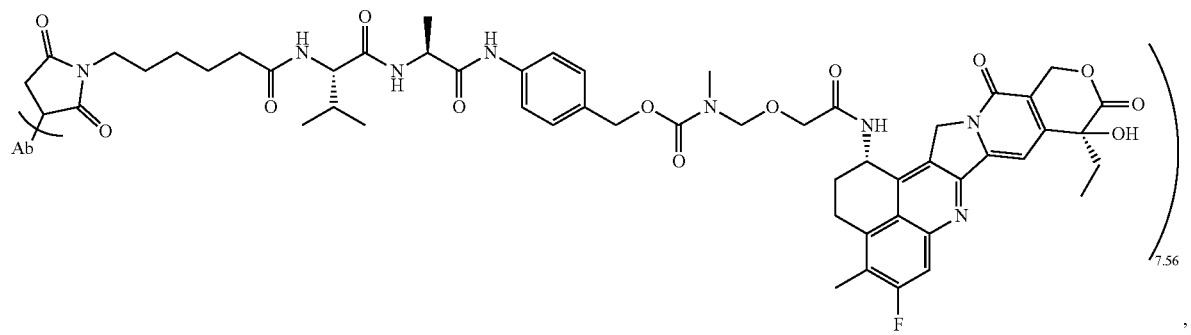

12

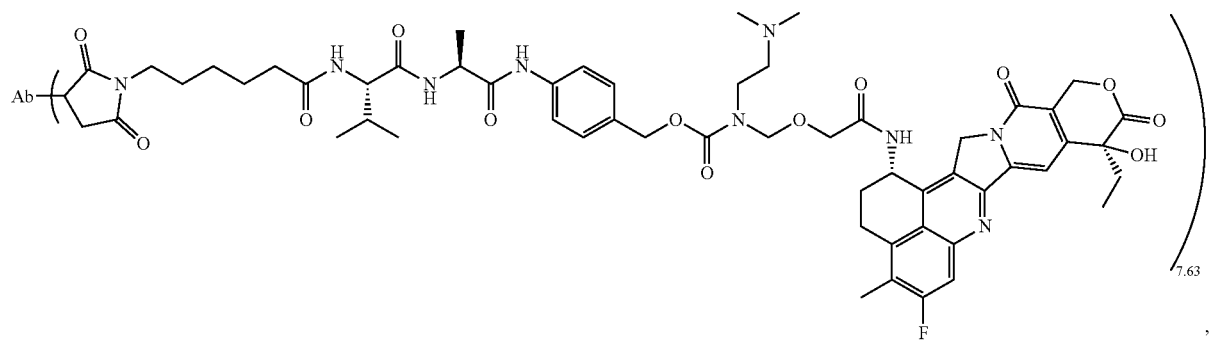

13

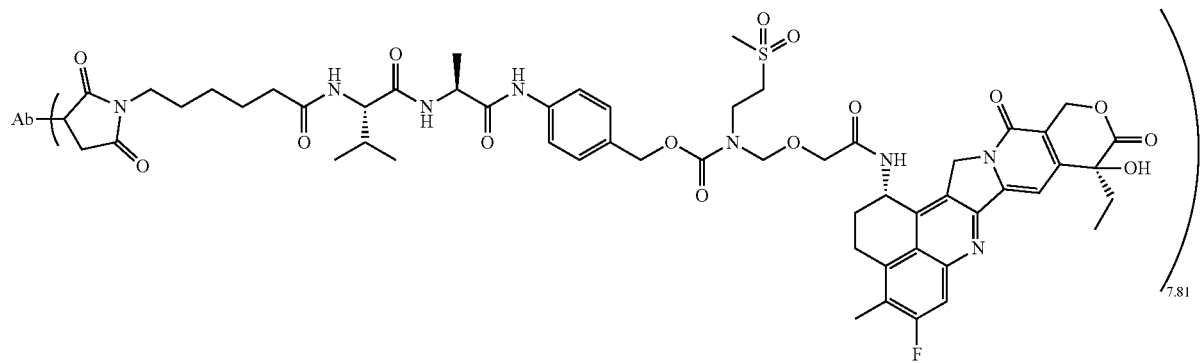
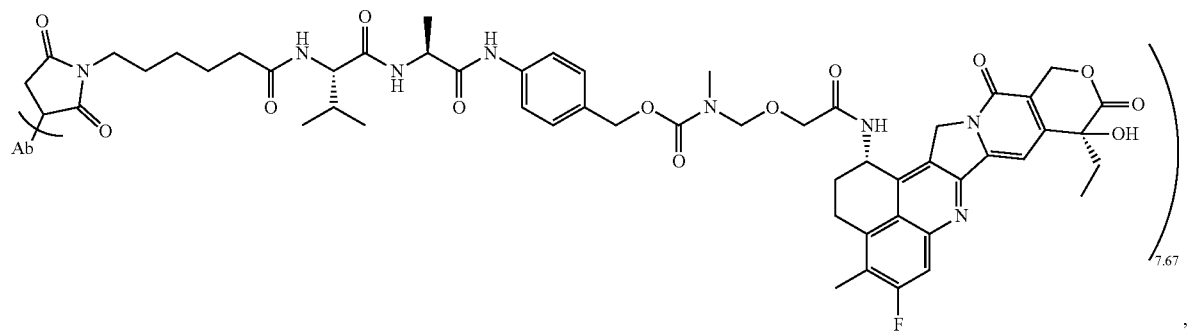
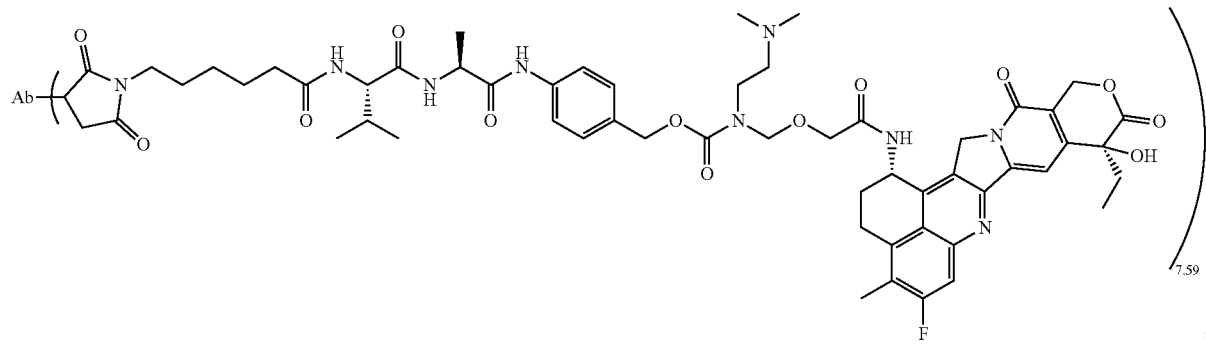
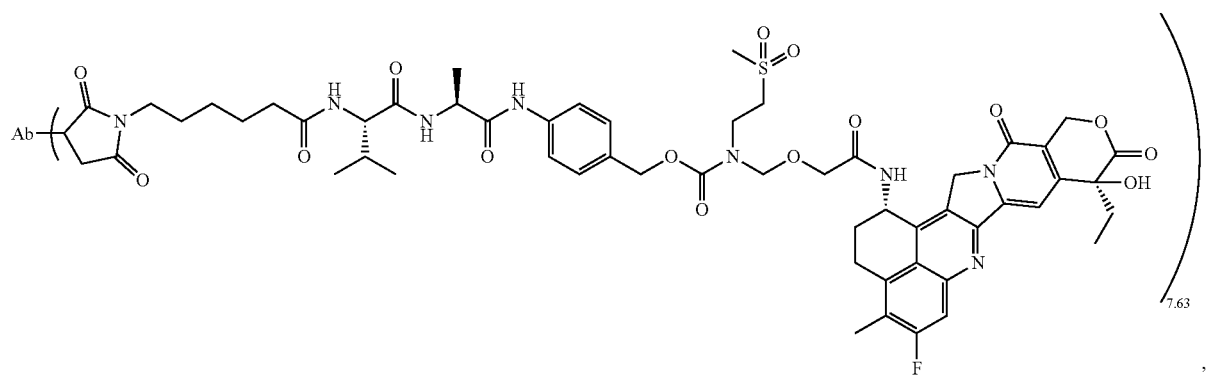

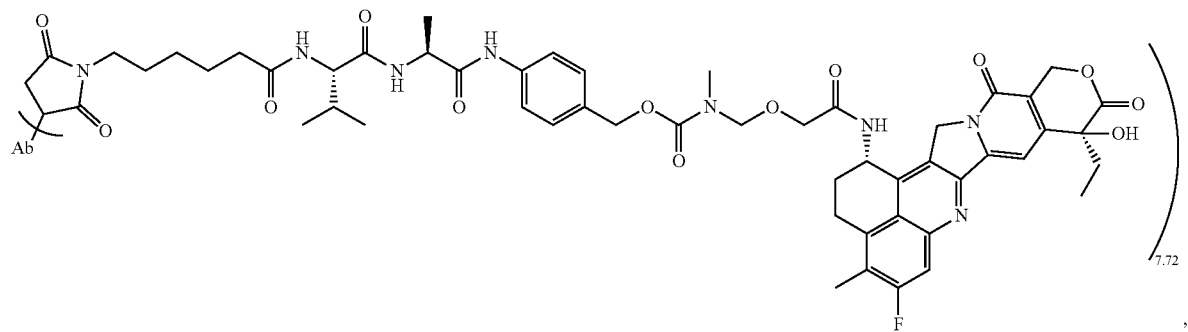
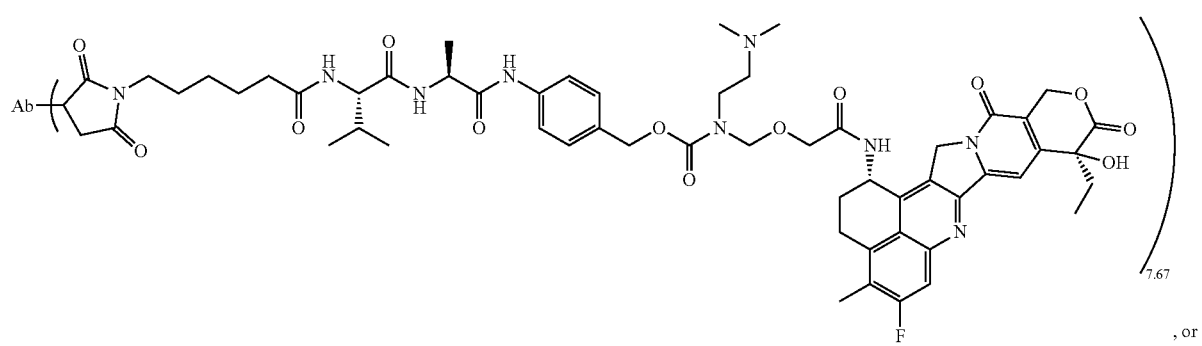
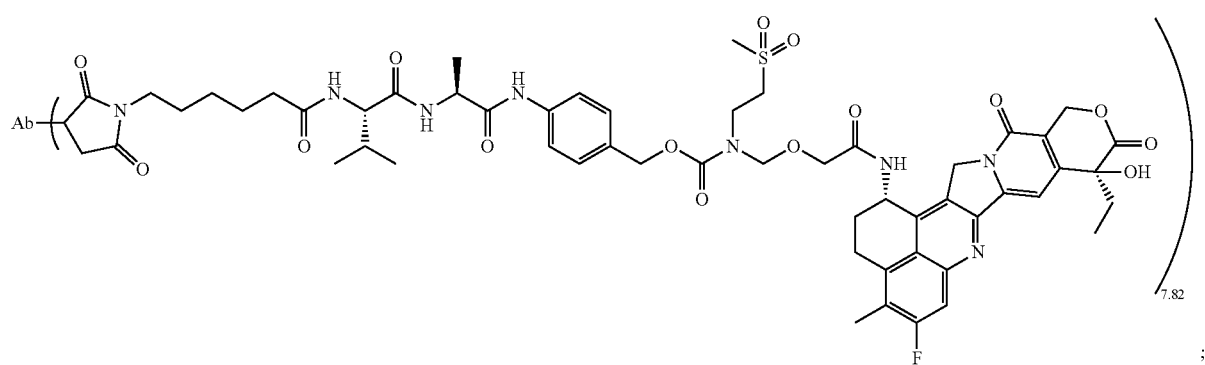

wherein Ab is HER3 antibody A or the variant of HER3 antibody A; the amino acid sequence of the light chain in the variant of HER3 antibody A is preferably shown in SEQ ID NO: 1, the amino acid sequence of the heavy chain is preferably selected from SEQ ID NO: 3 or SEQ ID NO: 4.

In a preferred embodiment of the present disclosure, the antibody-drug conjugate is preferably any one of the following compounds:

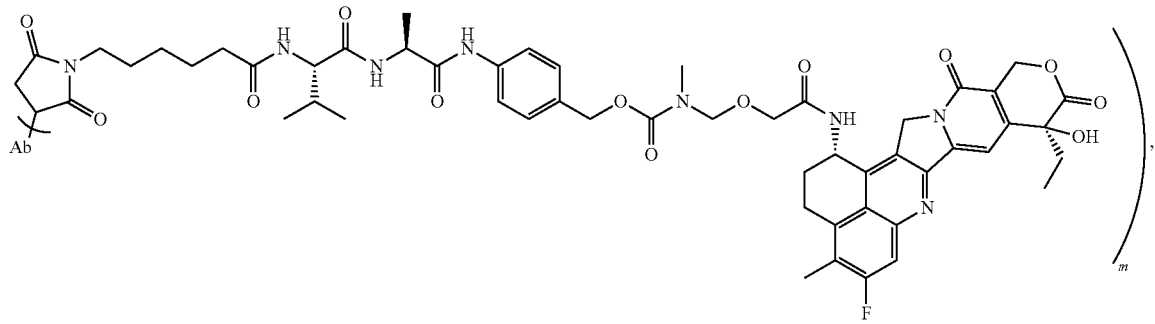

Ab is HER3 antibody A, and m is preferably 7.56;

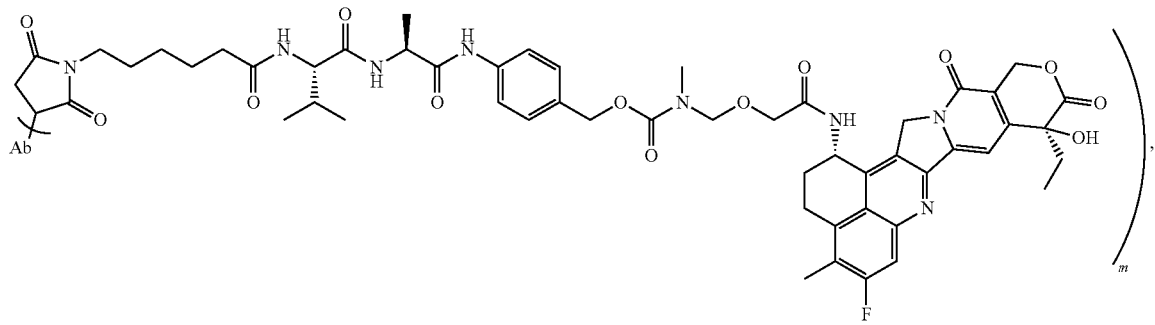

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 3, and m is preferably 7.67;

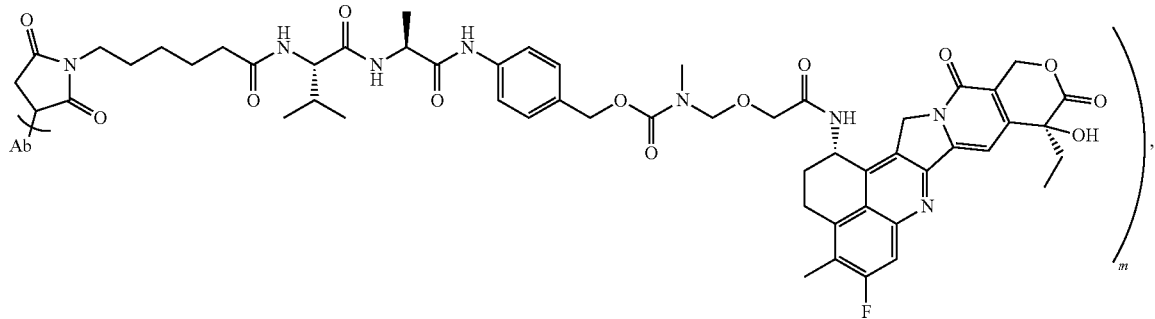

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 4, and m is preferably 7.72;

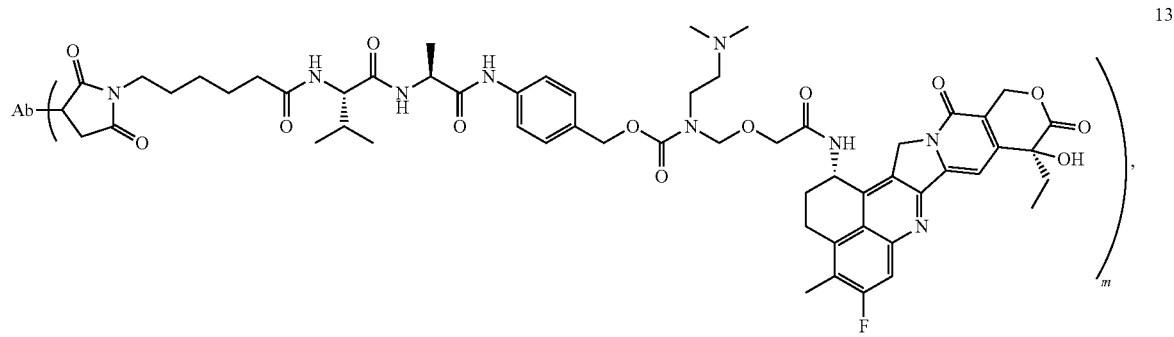

Ab is HER3 antibody A, and m is preferably 7.63;

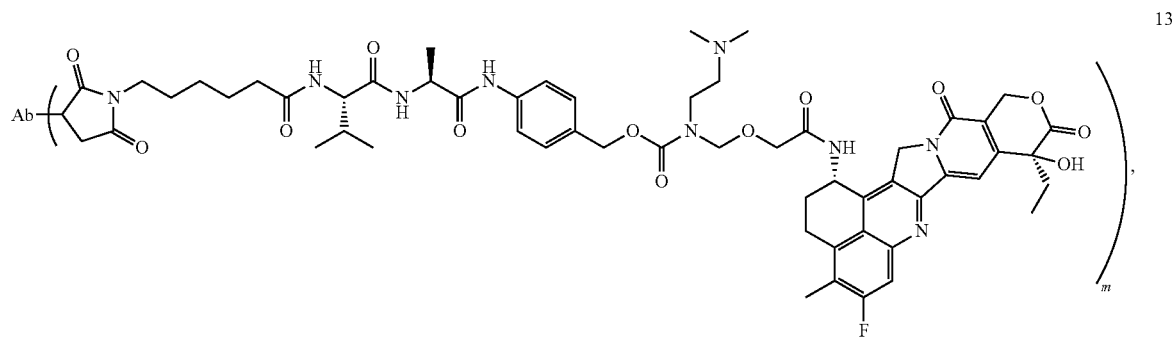

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 3, and m is preferably 7.59;

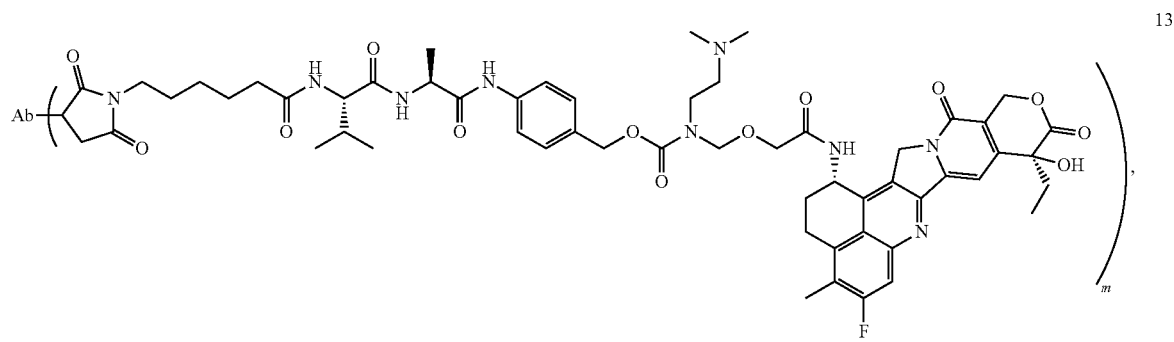

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 4, and m is preferably 7.67;

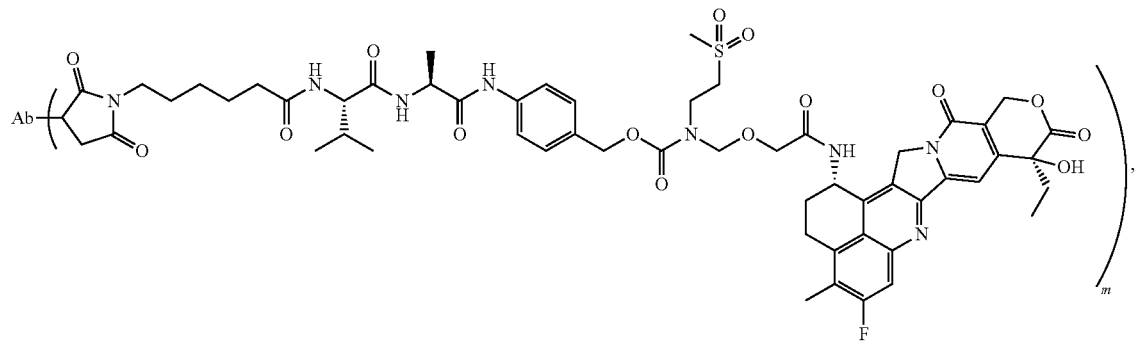

Ab is HER3 antibody A, and m is preferably 7.81;

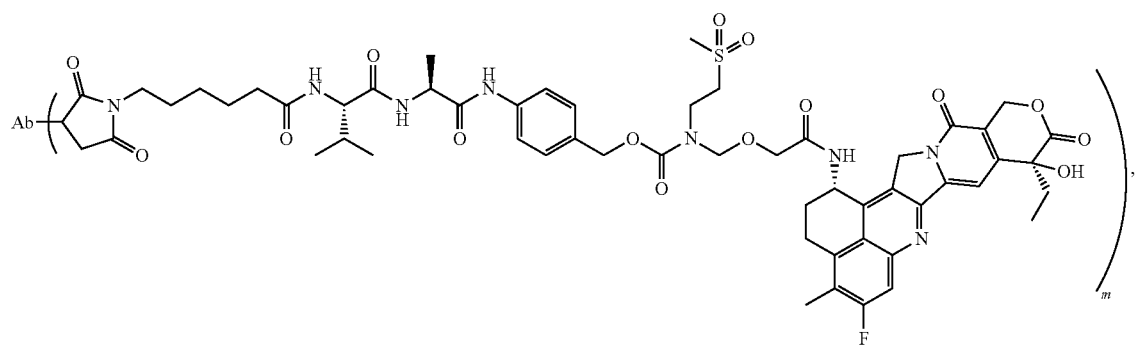

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 3, and m is preferably 7.63

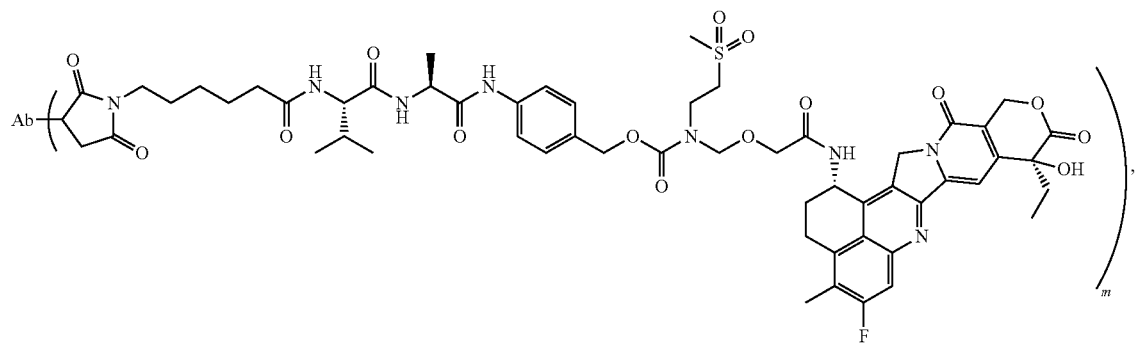

Ab is the variant of HER3 antibody A; the amino acid sequence of the light chain in the variant of HER3 antibody A is preferably shown in SEQ ID NO: 1, and the heavy chain is preferably the amino acid sequence shown in SEQ ID NO: 4, and m is preferably 7.82

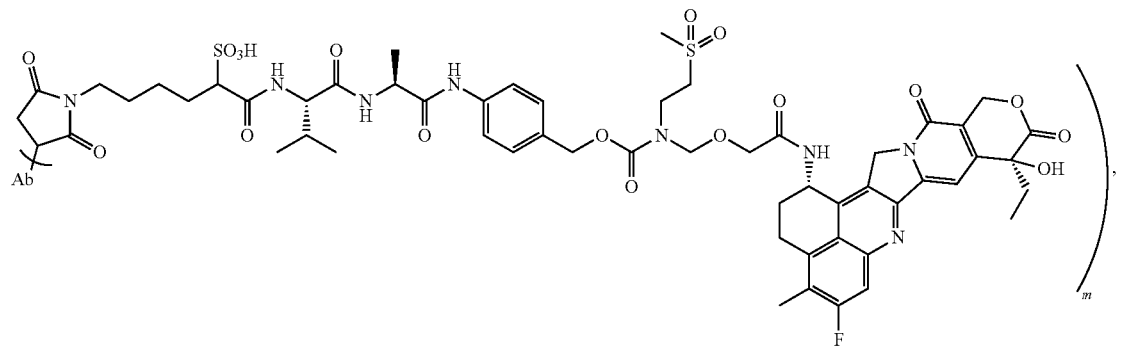
Ab is HER3 antibody A, and m is preferably 7.56;
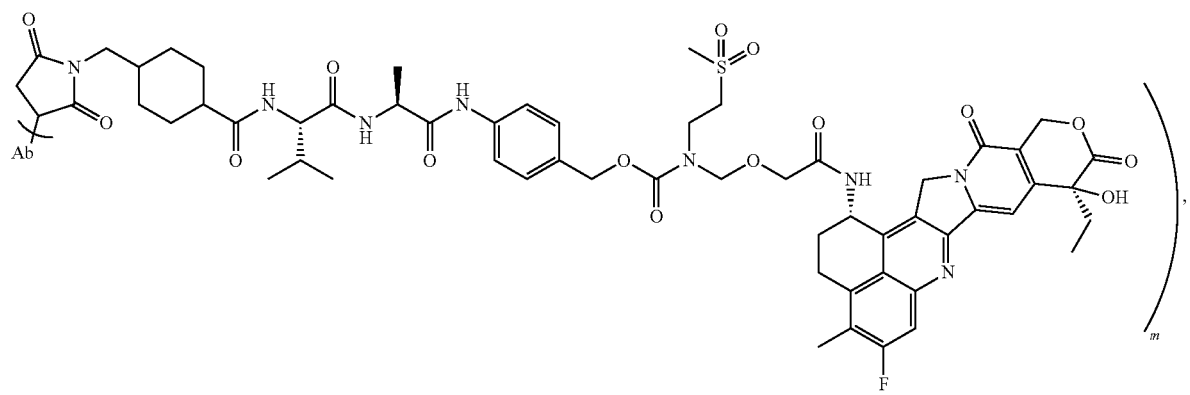
Ab is HER3 antibody A, and m is preferably 7.83;
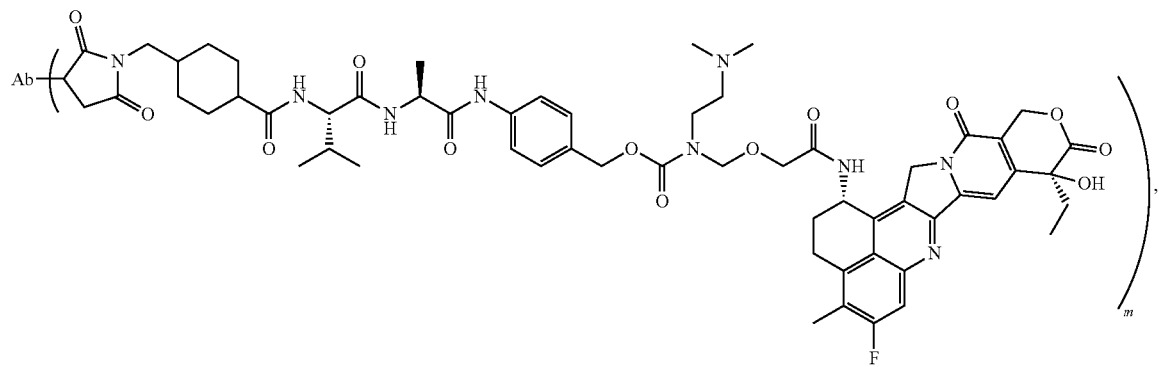

Ab is HER3 antibody A, and m is preferably 7.49;
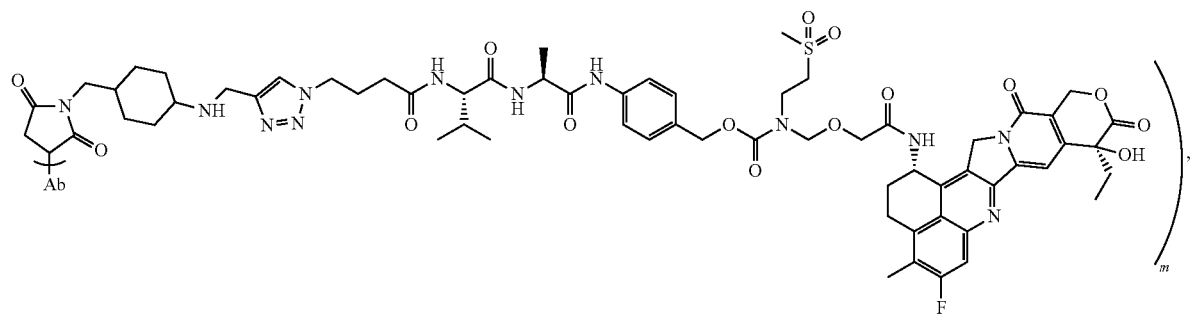
Ab is HER3 antibody A, and m is preferably 7.60;
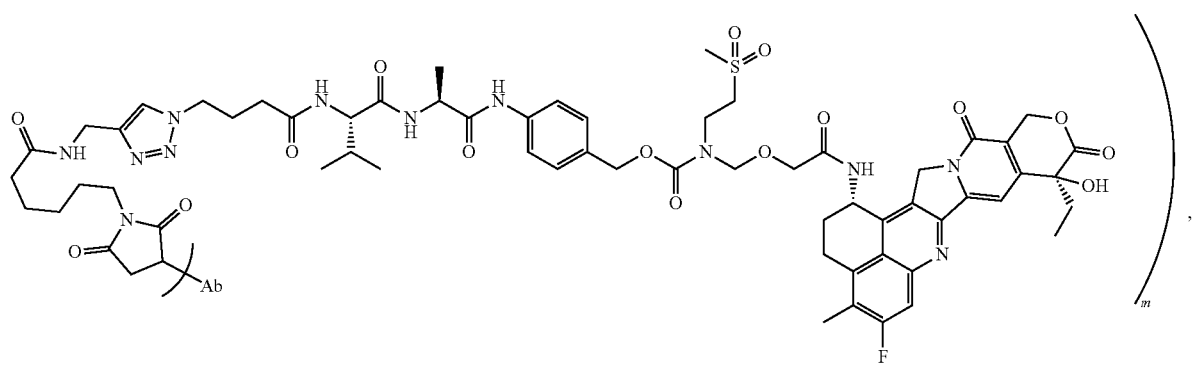
Ab is HER3 antibody A, and m is preferably 7.78;
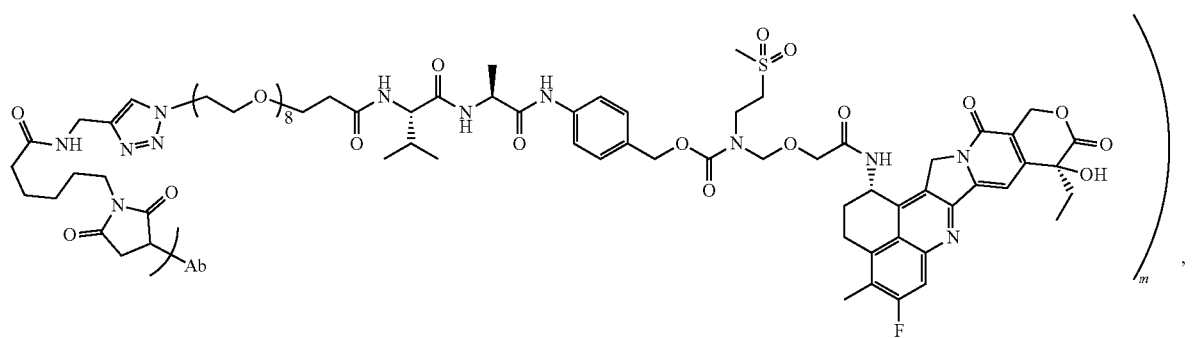

Ab is HER3 antibody A, and m is preferably 7.65;

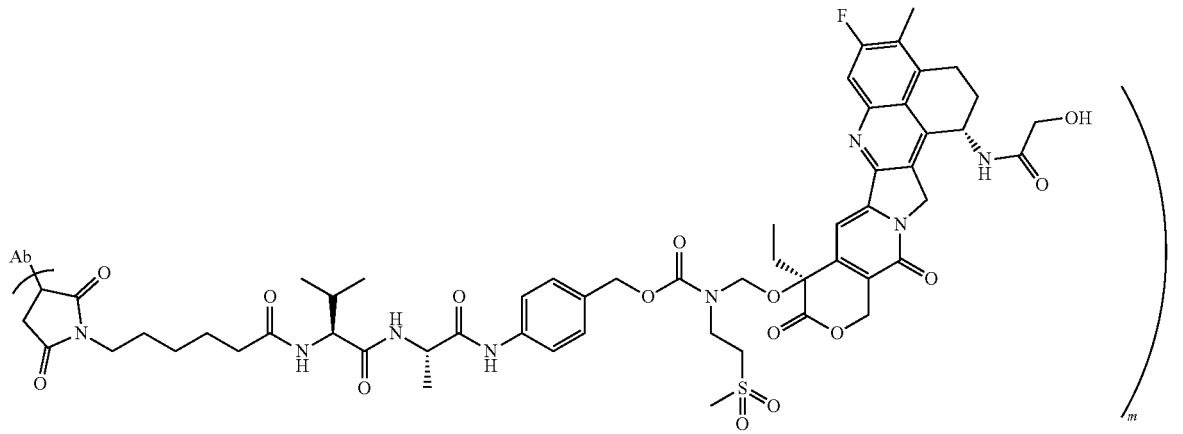

Ab is HER3 antibody A, and m is preferably 7.83; or

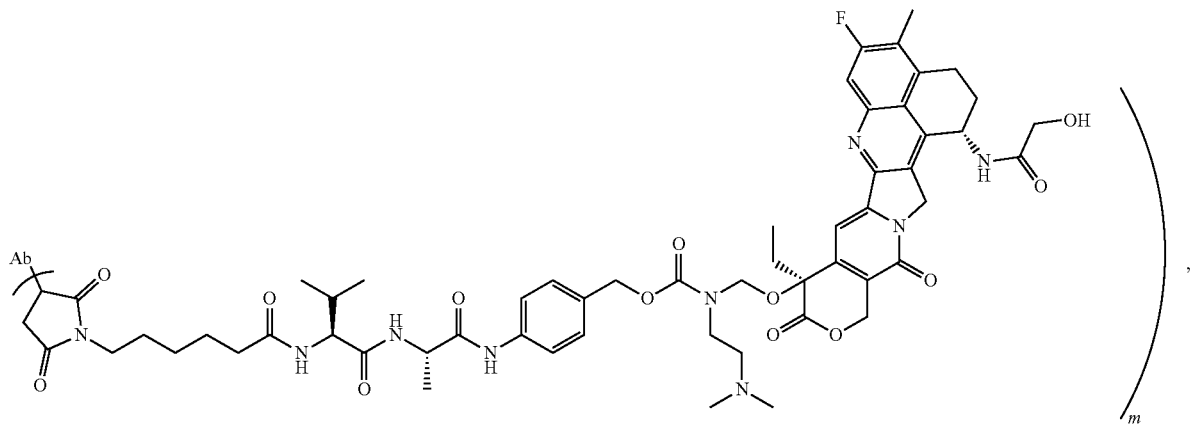

Ab is HER3 antibody A, and m is preferably 7.82.

The present disclosure also provides an antibody, the amino acid sequence of the light chain in the antibody is preferably shown in SEQ ID NO: 1; the amino acid sequence of the heavy chain in the antibody is shown in SEQ ID NO: 3 or SEQ ID NO: 4.

The present disclosure also provides a method for preparing the antibody-drug conjugate, comprising the following step: carrying out a coupling reaction between a compound of formula II and Ab-hydrogen as shown below;

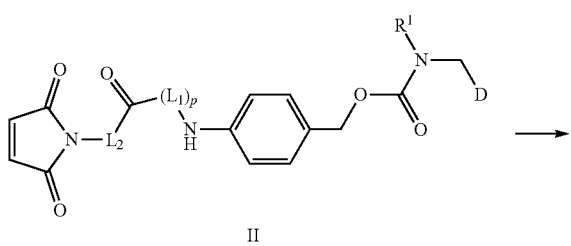

-continued

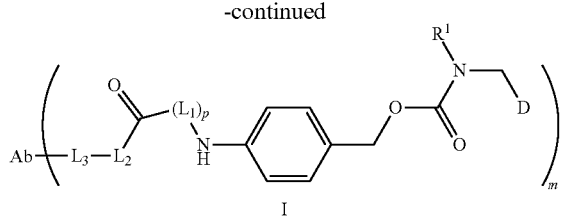

wherein $L_1$, $L_2$, $L_3$, $R^1$, p, and Ab are defined as above.

In the present disclosure, the conditions and operations of the coupling reaction can be conventional conditions and operations for the coupling reaction in the art.

The present disclosure also provides a pharmaceutical composition, comprising substance X and a pharmaceutically acceptable excipient; the substance X is the antibody-drug conjugate, the pharmaceutically acceptable salt thereof, the solvate thereof, or the solvate of the pharmaceutically acceptable salt thereof as defined above.

In the pharmaceutical composition, the substance X may be used in a therapeutically effective amount.

The present disclosure also provides a use of the substance X or the pharmaceutical composition in the manufacture of a HER3 protein inhibitor.

The present disclosure also provides a use of the substance X or the pharmaceutical composition in the manufacture of a drug for treating and/or preventing a tumor, and the tumor is preferably a HER3-positive tumor.

In the use, the HER3 positive tumor is preferably one or more than one of HER3 positive lung cancer, ovarian cancer, colorectal cancer, breast cancer, prostate cancer, and gastric cancer.

In some embodiments of the present disclosure, for the prostate cancer, the prostate cancer cells are 22Rv1 cells.

In some embodiments of the present disclosure, for the prostate cancer, the prostate cancer cells are LNCaP cells.

In some embodiments of the present disclosure, for the colorectal cancer, the colorectal cancer cells are SW620 cells.

In some embodiments of the present disclosure, for the lung cancer, the lung cancer cells are NCI-H820 cells.

In some embodiments of the present disclosure, for the ovarian cancer, the ovarian cancer cells are OVCAR-8 cells.

In some embodiments of the present disclosure, for the lung cancer, the lung cancer cells are HCC827 cells.

In some embodiments of the present disclosure, for the breast cancer, the breast cancer cells are SK-BR-3 cells.

Unless otherwise indicated, the following terms appearing in the specification and claims of the present disclosure have the following meanings:

The pharmaceutical excipient may be an excipient widely used in the field of pharmaceutical production. The excipient is mainly used to provide a safe, stable, and functional pharmaceutical composition, and can also provide a method for the subject to dissolve the active ingredient at a desired rate after administration, or to facilitate effective absorption of the active ingredient after the subject receives administration of the composition. The pharmaceutical excipient can be an inert filler or provide a certain function, such as stabilizing the overall pH value of the composition or preventing degradation of the active ingredient in the composition. The pharmaceutical excipients may include one or more of the following excipients: buffers, chelating agents, preservatives, solubilizers, stabilizers, vehicles, surfactants, colorants, flavoring agents and sweeteners.

The term "pharmaceutically acceptable" refers to salts, solvents, excipients and the like that are generally non-toxic, safe, and suitable for patient use. The "patient" is preferably a mammal, more preferably a human being.

The term "pharmaceutically acceptable salt" refers to a salt prepared from the compound of the present disclosure and a relatively non-toxic and pharmaceutically acceptable acid or alkali. When the compound of the present disclosure contains relatively acidic functional groups, an alkali addition salt can be obtained by contacting a sufficient amount of pharmaceutically acceptable alkali with the neutral form of the compound in a pure solution or an appropriate inert solvent. The pharmaceutically acceptable alkali addition salt includes, but is not limited to, lithium salt, sodium salt, potassium salt, calcium salt, aluminium salt, magnesium salt, zinc salt, bismuth salt, ammonium salt, and diethanolamine salt. When the compound of the present disclosure contains relatively alkaline functional groups, an acid addition salt can be obtained by contacting a sufficient amount of pharmaceutically acceptable acid with the neutral form of the compound in a pure solution or an appropriate inert solvent. The pharmaceutically acceptable acid includes inorganic acid, and the inorganic acid includes, but is not limited to, hydrochloric acid, hydrobromic acid, hydroiodic acid, nitric acid, carbonic acid, phosphoric acid, phosphorous acid, sulfuric acid, etc. The pharmaceutically acceptable acid includes organic acid, and the organic acid includes, but is not limited to, acetic acid, propionic acid, oxalic acid, isobutyric acid, maleic acid, malonic acid, benzoic acid, succinic acid, suberic acid, trans-butenedioic acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, bitartrate, ascorbic acid, gentisic acid, fumaric acid, gluconic acid, saccharic acid, formic acid, ethanesulfonic acid, pamoic acid (i.e., 4,4'-methylene-bis(3-hydroxy-2-naphthoic acid)), amino acid (e.g., glutamic acid and arginine), etc. When the compound of the present disclosure contains relatively acidic functional groups and relatively alkaline functional groups, it can be converted into an alkali addition salt or an acid addition salt. For details, see Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

The term "solvate" refers to a substance formed by combining the compound of the present disclosure with a stoichiometric or non-stoichiometric amount of solvent. Solvent molecules in the solvate can exist in an ordered or non-ordered arrangements. The solvent includes, but is not limited to, water, methanol, ethanol, etc.

Natural or natural sequence HER3 can be isolated from nature or produced by recombinant DNA technology, chemical synthesis, or a combination of the above and similar techniques.

Antibody is interpreted in the broadest sense here, which can specifically bind to the target through at least one antigen recognition region located in the variable region of the immunoglobulin molecule, such as carbohydrate, polynucleotide, fat, polypeptide, etc. Specifically, it includes complete monoclonal antibodies, polyclonal antibodies, bi specific antibodies and antibody fragments, as long as they have the required biological activity. Variants of antibodies of the present disclosure refer to amino acid sequence mutants, and covalent derivatives of natural polypeptides, provided that the biological activity equivalent to that of natural polypeptides is retained. The difference between amino acid sequence mutants and natural amino acid sequences is generally that one or more than one amino acid in the natural amino acid sequence is substituted or one or more than one amino acid is deleted and/or inserted in the polypeptide sequence. Deletion mutants include fragments of natural polypeptides and N-terminal and/or C-terminal truncation mutants. Generally, the amino acid sequence mutant is at least 70% (e.g., 70%, 75%, 80%, 85%, 90%, 95%, or 99%) identical to the natural sequence.

Monoclonal antibody means that the antibody comes from a group of basically homogeneous antibodies, that is, the antibodies constituting the cluster are completely identical, except for a few natural mutations that may exist or isomers produced during the preparation and expression of antibody. Monoclonal antibodies have a high degree of specificity against a single antigen. Polyclonal antibodies, on the other hand, contain different antibodies targeting different determinants, with each monoclonal antibody targeting only one determinant of the antigen.

In the present disclosure, the monoclonal antibody also specifically includes chimeric antibody and fragments thereof, that is, part of the heavy chain and/or light chain of the antibody comes from a certain kind, a certain class or a certain subclass, and the rest is related to another kind, another class or another subclass.

The antibodies of the present disclosure can be prepared using techniques well known in the art, such as hybridoma methods, recombinant DNA techniques, phage display techniques, synthetic techniques or combinations thereof, or other techniques known in the art.

Description of the term "drug-antibody ratio" (DAR). L-D is a reactive group with the conjugation site on the antibody, L is a linker, D is a cytotoxic agent further coupled to the antibody connected to L. In the present disclosure, D is Dxd. The number of D coupled to each antibody is represented by m or m can also represent the number of D coupled to a single antibody. In some embodiments, m is actually an average value between 2 and 8, 4 and 8, or 6 and 8, or m is an integer of 2, 3, 4, 5, 6, 7, or 8; in some embodiments, m is an average value of 2, 4, 6, or 8; in other embodiments, m is an average value of 2, 3, 4, 5, 6, 7, or 8.

The linker refers to the direct or indirect connection between the antibody and the drug. The linker can be connected to the mAb in many ways, such as through surface lysine, reductive coupling to oxidized carbohydrates, and through cysteine residues released by reducing interchain disulfide bonds. Many ADC connection systems are known in the art, including connections based on hydrazones, disulfides and peptides.

The term "treatment" or its equivalent expression, when used for, for example, cancer, refers to a procedure or process for reducing or eliminating the number of cancer cells in a patient or alleviating the symptoms of cancer. The "treatment" of cancer or another proliferative disorder does not necessarily mean that the cancer cells or other disorders will actually be eliminated, but the number of cells or disorders will actually be reduced or the symptoms of cancers or other disorders will actually be alleviated. Generally, the method of treating cancer will be carried out even if it has only a low probability of success, but it is still considered to induce an overall beneficial course of action considering the patient's medical history and estimated survival expectation.

The term "prevention" refers to a reduced risk of acquiring or developing a disease or disorder.

The term "cycloalkyl" refers to a saturated cyclic hydrocarbon group with three to twenty carbon atoms (e.g., $C_3$-$C_6$ cycloalkyl), including monocyclic and polycyclic cycloalkyl. The cycloalkyl contains 3 to 20 carbon atoms, preferably 3 to 10 carbon atoms, and more preferably 3 to 6 carbon atoms. Examples of cycloalkyl include, but are not limited to, cyclopropyl, cyclobutyl, cyclopentyl, cyclohexyl, cycloheptyl, cyclooctyl, cyclononyl, and cyclodecyl.

The term "alkyl" refers to a straight or branched chain alkyl group with a specified number of carbon atoms. Examples of alkyl groups include methyl, ethyl, n-propyl, isopropyl, n-butyl, t-butyl, isobutyl, sec-butyl, n-pentyl, isopentyl, n-hexyl, n-heptyl, n-octyl, and similar alkyl groups.

The term "halogen" refers to fluorine, chlorine, bromine, or iodine.

The term "heteroaryl" refers to an aryl group (or aromatic ring) containing 1, 2, 3, or 4 heteroatoms independently selected from N, O, and S, which may be a monocyclic, bicyclic, or tricyclic aromatic system, such as furyl, pyridinyl, pyridazinyl, pyrimidinyl, pyrazinyl, thiophenyl, isoxazolyl, oxazolyl, diazolyl, imidazolyl, pyrrolyl, pyrazolyl, triazolyl, tetrazolyl, thiazolyl, isothiazolyl, thiadiazolyl, benzimidazolyl, indolyl, indazolyl, benzothiazolyl, benzisothiazolyl, benzoxazolyl, benzisoxazolyl, quinolyl, isoquinolyl, etc.

The term "aryl" refers to any stable monocyclic or bicyclic carbocycle, wherein all rings are aromatic. Examples of the aryl moiety include phenyl or naphthyl.

The above preferred conditions can be combined arbitrarily to obtain preferred embodiments of the present disclosure without violating common knowledge in the art.

Unless otherwise specified, room temperature in the present disclosure refers to 20 to 30° C.

The reagents and raw materials used in the present disclosure are all commercially available.

The positive progressive effects of the present disclosure are as follows:

1. The antibody-drug conjugate containing HER3 antibody provided by the present disclosure has good targeting and has a good inhibitory effect on various tumor cells expressing HER3, etc.
2. In vivo studies have shown that the antibody-drug conjugate of the present disclosure has better in vitro cytotoxicity and in vivo antitumor activity.
3. The antibody-drug conjugate of the present disclosure has good solubility and good druggability. There are no abnormal phenomena such as precipitation during the coupling preparation process, which is very conducive to the preparation of the antibody-drug conjugate.

BRIEF DESCRIPTION OF THE DRAWINGS

FIG. 1 shows the construction of expression vectors for the light and heavy chains of an antibody; wherein Ab-L is the light chain of the antibody, and Ab-H is the heavy chain of the antibody.

DETAILED DESCRIPTION OF THE PREFERRED EMBODIMENT

The present disclosure will be further described below with reference to embodiments, but the present disclosure is not therefore limited to the scope of the embodiment. Experimental methods without specific conditions in the following embodiments are selected according to conventional methods and conditions, or according to the commercial specification.

DESCRIPTION OF ABBREVIATIONS

PCR polymerase chain reaction
CHO Chinese hamster ovary cells
HTRF homogeneous time-resolved fluorescence
PB phosphate buffer
EDTA ethylenediaminetetraacetic acid
TECP tris(2-carboxyethyl)phosphine
DMSO dimethyl sulfoxide
DMF N,N-dimethylformamide
HATU 2-(7-azabenzotriazol-1-yl)-N,N,N',N'-tetramethyluronium hexafluorophosphate
v/v V/V, volume ratio
UV ultraviolet visible light
ELISA enzyme-linked immunosorbent assay
BSA bovine serum albumin
rpm revolutions per minute
FBS fetal bovine serum

Example 1: Preparation of HER3 Antibody

In the present disclosure, the monoclonal antibody FDA026 with high affinity and specific targeting HER3 was selected, the amino acid sequence of its light chain was shown in SEQ ID NO: 1, and the amino acid sequence of its heavy chain was shown in SEQ ID NO: 2. The light and heavy chain nucleotide sequences of FDA026 were obtained by whole gene synthesis (Suzhou Genewiz). They were separately constructed into the pV81 vector (as shown in FIG. 1) by double digestion with EcoR I and Hind III (purchased from TAKARA), and then transformed into Trans 1-T1 competent cells (purchased from Beijing TransGen Biotech, product number: CD501-03) by ligation, which were picked for cloning, PCR identification and sent for sequencing confirmation. Positive clones were cultured and expanded for plasmid extraction, thus obtaining the antibody light chain eukaryotic expression plasmid FDA026-L/pV81 and the antibody heavy chain eukaryotic expression plasmid FDA026-H/pV81. These two plasmids were linearized by digestion with XbaI (purchased from Takara, product number: 1093S). The light and heavy chain eukaryotic expression plasmids were transformed into CHO cells adapted to suspension growth (purchased from ATCC) at a ratio of 1.5/1 by electroporation. After electroporation, the cells were seeded at 2000 to 5000 cells/well in a 96-well plate. After 3 weeks of culture, the expression level was measured by HTRF method (homogeneous time-resolved fluorescence). The top ten cell pools in terms of expression level were selected for expansion and cryopreservation. A cell was revived into a 125 mL shake flask (culture volume of 30 mL) and cultured at 37° C., 5.0% $CO_2$, and 130 rpm by vibration for 3 days, then expanded to a 1000 mL shake flask (culture volume of 300 mL) and cultured at 37° C., 5.0% $CO_2$, and 130 rpm by vibration. Starting on the 4th day, 5 to 8% of the initial culture volume of replenishment culture medium was added every other day. The culture was ended on 10th to 12th day and the harvest liquid was centrifuged at 9500 rpm for 15 minutes to remove the cell sediment. The supernatant was collected and filtered through a 0.22 μm filter membrane. The treated sample was purified using a Mab Select affinity chromatography column (purchased from GE) to obtain antibody FDA026.

Same preparation method as described above was used to prepare HER3 antibody FDA028 with Fc mutations (i.e., E233P, L234V, L235A) (the light chain amino acid sequence is shown in SEQ ID NO: 1 and the heavy chain sequence is shown in SEQ ID NO: 3) and HER3 antibody FDA029 with Fc mutations (i.e., L234F, L235E, P331S) (the amino acid sequence of the light chain is shown in SEQ ID NO: 1, and the heavy chain sequence is shown in SEQ ID NO: 4).

The light chain sequences of FDA026, FDA028, and FDA029 are shown below:

```
SEQ ID NO: 1:
DIEMTQSPDS LAVSLGERAT INCRSSQSVL YSSSNRNYLA WYQQNPGQPP    50

KLLIYWASTR ESGVPDRFSG SGSGTDFTLT ISSLQAEDVA VYYCQQYYST   100

PRTFGQGTKV EIKRTVAAPS VFIFPPSDEQ LKSGTASVVC LLNNFYPREA   150

KVQWKVDNAL QSGNSQESVT EQDSKDSTYS LSSTLTLSKA DYEKHKVYAC   200

EVTHQGLSSP VTKSFNRGEC                                    220
```

The heavy chain sequence of FDA026 is shown below:

```
SEQ ID NO: 2:
QVQLQQWGAG LLKPSETLSL TCAVYGGSFS GYYWSWIRQP PGKGLEWIGE    50

INHSGSTNYN PSLKSRVTIS VETSKNQFSL KLSSVTAADT AVYYCARDKW   100

TWYFDLWGRG TLVTVSSAST KGPSVFPLAP SSKSTSGGTA ALGCLVKDYF   150

PEPVTVSWNS GALTSGVHTF PAVLQSSGLY SLSSVVTVPS SSLGTQTYIC   200

NVNHKPSNTK VDKRVEPKSC DKTHTCPPCP APELLGGPSV FLFPPKPKDT   250

LMISRTPEVT CVVVDVSHED PEVKFNWYVD GVEVHNAKTK PREEQYNSTY   300

RVVSVLTVLH QDWLNGKEYK CKVSNKALPA PIEKTISKAK GQPREPQVYT   350

LPPSREEMTK NQVSLTCLVK GFYPSDIAVE WESNGQPENN YKTTPPVLDS   400

DGSFFLYSKL TVDKSRWQQG NVFSCSVMHE ALHNHYTQKS LSLSPGK     447
```

The heavy chain sequence of FDA028 is shown below:

```
FDA028 heavy chain
                                              SEQ ID NO: 3
QVQLQQWGAGLLKPSETLSLTCAVYGGSFSGYYWSWIRQPPGKGLEWIG
EINHSGSTNYNPSLKSRVTISVETSKNQFSLKLSSVTAADTAVYYCARD
KWTWYFDLWGRGTLVTVSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKKVEPKSCDKTHTCPPCPAPPVAGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK
```

The heavy chain sequence of FDA029 is shown below:

```
FDA029 heavy chain
                                              SEQ ID NO: 4
QVQLQQWGAGLLKPSETLSLTCAVYGGSFSGYYWSWIRQPPGKGLEWIG
EINHSGSTNYNPSLKSRVTISVETSKNQFSLKLSSVTAADTAVYYCARD
KWTWYFDLWGRGTLVTVSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKKVEPKSCDKTHTCPPCPAPEFEGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPASIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK
```

Example 2: Synthesis of Linker-Drug Conjugates

Example 2-1: Synthesis of LE12

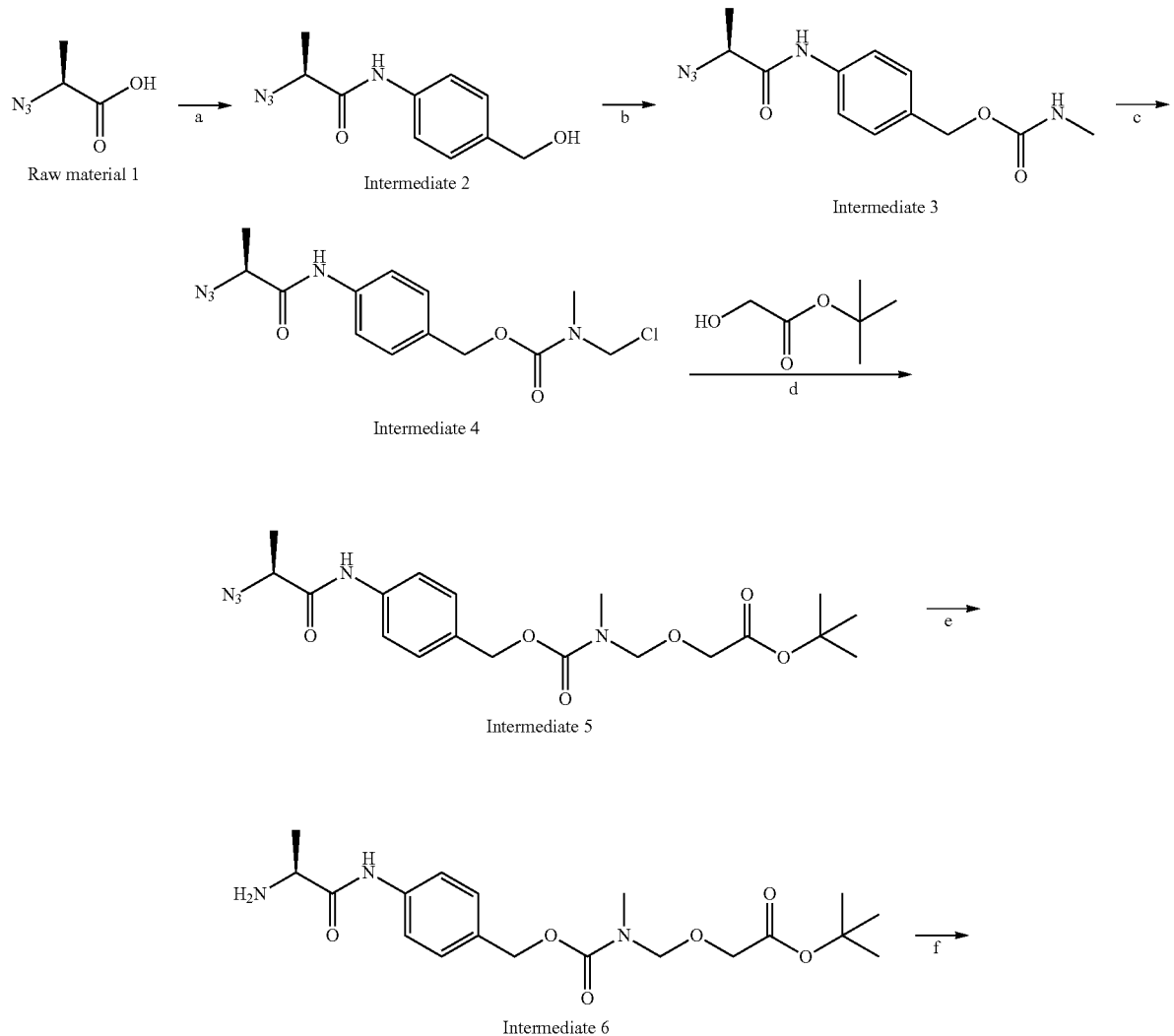

-continued
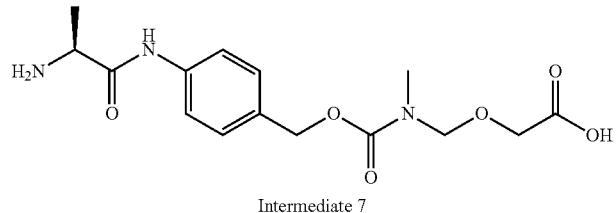
Intermediate 7
↓ g
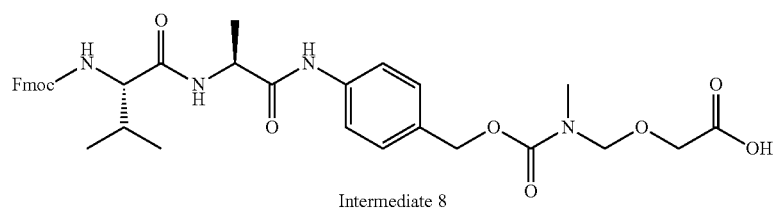
Intermediate 8
↓ h
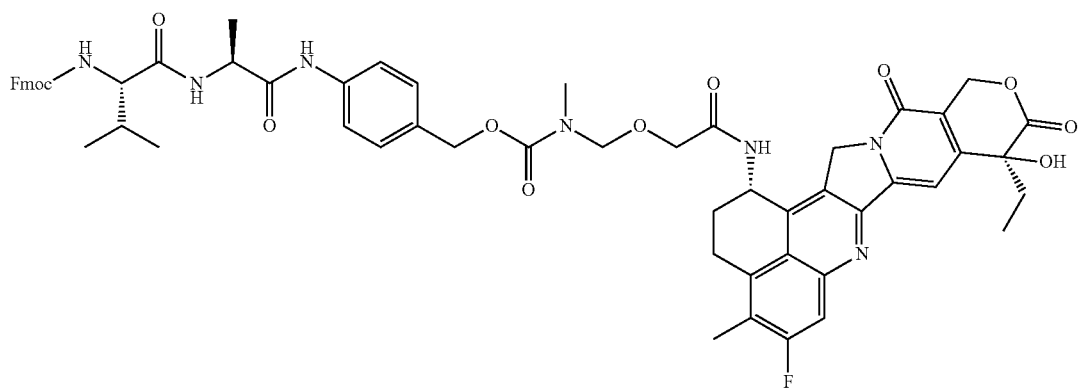
Intermediate 9
↓ i
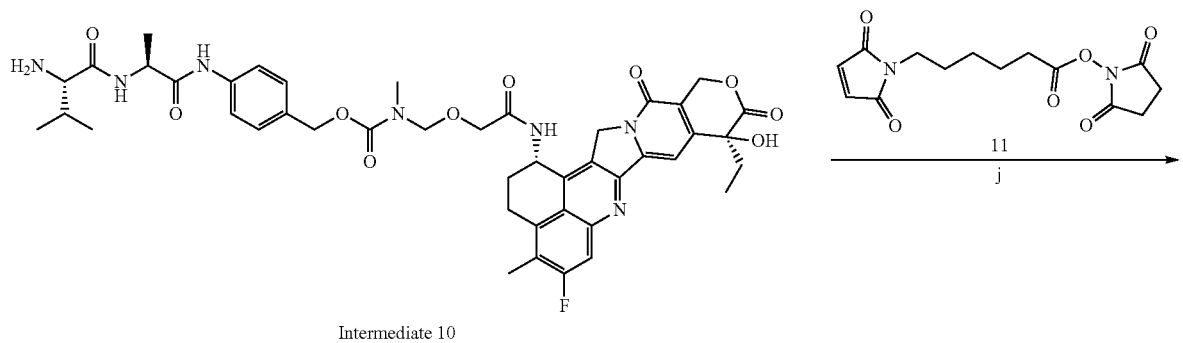
Intermediate 10

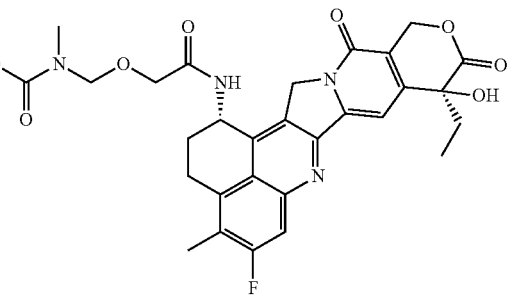

LE12

Synthesis of Intermediate 2:

(S)-2-Azidopropionic acid (10 g, 86.9 mmol) and 4-aminobenzyl alcohol (21.40 g, 173.8 mmol) were dissolved in a mixed solvent of 300 mL of dichloromethane and methanol (in a volume ratio of 2:1), and then 2-ethoxy-1-ethoxycarbonyl-1,2-dihydroquinoline (21.49 g, 86.9 mmol) was added thereto. The reaction was carried out at room temperature for 5 hours. The solvent was then evaporated under reduced pressure and the obtained crude product was purified by silica gel column chromatography [dichloromethane:ethyl acetate=1:1 (v/v)] to obtain intermediate 2 (16.3 g, yield of 85%), ESI-MS m/z: 221 (M+H).

Synthesis of Intermediate 3:

Intermediate 2 (15 g, 68.2 mmol) was mixed with bis(p-nitrophenyl)carbonate (22.82 g, 75.02 mmol) and dissolved in 200 mL of anhydrous N,N-dimethylformamide, and then 25 mL of triethylamine was added thereto, and the reaction was carried out at room temperature for 2 hours. After the complete reaction of the raw materials was monitored by liquid chromatography-mass spectrometry, methylamine hydrochloride (6.91 g, 102.3 mmol) was added thereto, and the reaction was continued at room temperature for 1 hour. After the reaction was completed, most of the solvent was removed by distillation under reduced pressure, then 200 mL of water and 200 mL of ethyl acetate were added thereto. The organic phase was collected after the phases were separated, and the organic phase was dried and concentrated, and then the obtained crude product was purified by silica gel column chromatography [dichloromethane:ethyl acetate=10:1 (v/v)] to obtain intermediate 3 (18.9 g, yield of 100%), ESI-MS m/z: 278 (M+H).

Synthesis of Intermediate 5:

Intermediate 3 (10 g, 36.1 mmol) was mixed with polyformaldehyde (1.63 g, 54.2 mmol) and dissolved in 150 mL of anhydrous dichloromethane. Trimethylchlorosilane (6.28 g, 57.76 mmol) was slowly added thereto and the reaction was carried out at room temperature for 2 hours to obtain a crude solution of intermediate 4. The reaction was monitored by liquid chromatography-mass spectrometry after sampling and quenching with methanol. After the reaction was completed, the reaction mixture was filtered and then tert-butyl hydroxyacetate (9.54 g, 72.2 mmol) and triethylamine (10 mL, 72.2 mmol) were added to the filtrate and the reaction was continued at room temperature for 2 hours. After the reaction was completed, most of the solvent was removed by distillation under reduced pressure, and then the obtained crude product was purified by silica gel column chromatography [petroleum ether:ethyl acetate=3:1 (v/v)] to obtain intermediate 5 (11.2 g, yield of 74%), ESI-MS m/z: 422 (M+H).

Synthesis of Intermediate 6:

Intermediate 5 (10 g, 23.8 mmol) was dissolved in 80 mL of anhydrous tetrahydrofuran, and 80 mL of water was added thereto, and then tris(2-carboxyethylphosphine) hydrochloride (13.6 g, 47.6 mmol) was added thereto and the reaction was carried out for 4 hours at room temperature. After the reaction was completed, the tetrahydrofuran was removed by distillation under reduced pressure, and then the mixture was extracted with ethyl acetate. The obtained organic phase was dried and evaporated to remove the solvent under reduced pressure, and purified by silica gel column chromatography [dichloromethane:methanol=10:1 (v/v)] to obtain intermediate 6 (8.1 g, yield 86%), ESI-MS m/z: 396 (M+H).

Synthesis of Intermediate 8:

Intermediate 6 (5 g, 12.7 mmol) was dissolved in 60 mL of a mixed solvent of dichloromethane and methanol (v/v=2:1), and 3 mL of trifluoroacetic acid was slowly added thereto, and the reaction was carried out at room temperature for 30 min. After the reaction was completed, an equal volume of water and ethyl acetate were added thereto, and the organic phase was dried and concentrated, and the obtained crude product was directly used in the next step.

The crude product obtained from the previous step was dissolved in 50 mL of anhydrous N,N-dimethylformamide, and then Fmoc-L-valine N-hydroxysuccinimide ester (8.3 g, 19.1 mmol) and triethylamine (5 mL) were added thereto, and the reaction was carried out at room temperature for 2 hours. After the reaction was completed, most of the solvent was removed by distillation under reduced pressure, and then the obtained crude product was purified by silica gel column chromatography [dichloromethane:methanol=10:1 (v/v)] to obtain intermediate 8 (5.4 g, yield of 64%), ESI-MS m/z: 661 (M+H).

Synthesis of Intermediate 9:

Intermediate 8 (1 g, 1.5 mmol) was mixed with Exatecan methanesulfonate (0.568 g, 1 mmol) in 30 mL of anhydrous N,N-dimethylformamide, and then 2-(7-azabenzotriazol-1-yl)-N,N,N',N'-tetramethyluronium hexafluorophosphate (1.14 g, 3.0 mmol) and 2 mL of triethylamine were added thereto, and the reaction was carried out at room temperature for 2 hours. After the reaction was completed, the solvent was removed by distillation under reduced pressure, and then the obtained crude product was purified by silica gel column chromatography [chloroform:methanol=10:1 (v/v)] to obtain intermediate 9 (0.94 g, yield of 87%), ESI-MS m/z: 1078 (M+H).

Synthesis of Compound LE12:

Intermediate 9 (1 g, 0.929 mmol) was dissolved in 20 mL of anhydrous DMF, then 0.5 mL of 1,8-diazabicyclo[5.4.0]undec-7-ene was added thereto, and the reaction was carried out at room temperature for 1 hour. After the reaction of the raw materials was completed, N-succinimidyl 6-maleimidohexanoate (428.5 mg, 1.39 mmol) was added directly, and the reaction mixture was stirred at room temperature for 1 hour. The solvent was removed by distillation under reduced pressure, and then the obtained crude product was purified by silica gel column chromatography [chloroform:methanol=8:1 (v/v)] to obtain the title compound (0.7 g, yield of 73%), ESI-MS m/z: 1035 (M+H).

Example 2-2: Synthesis of Compound LE13

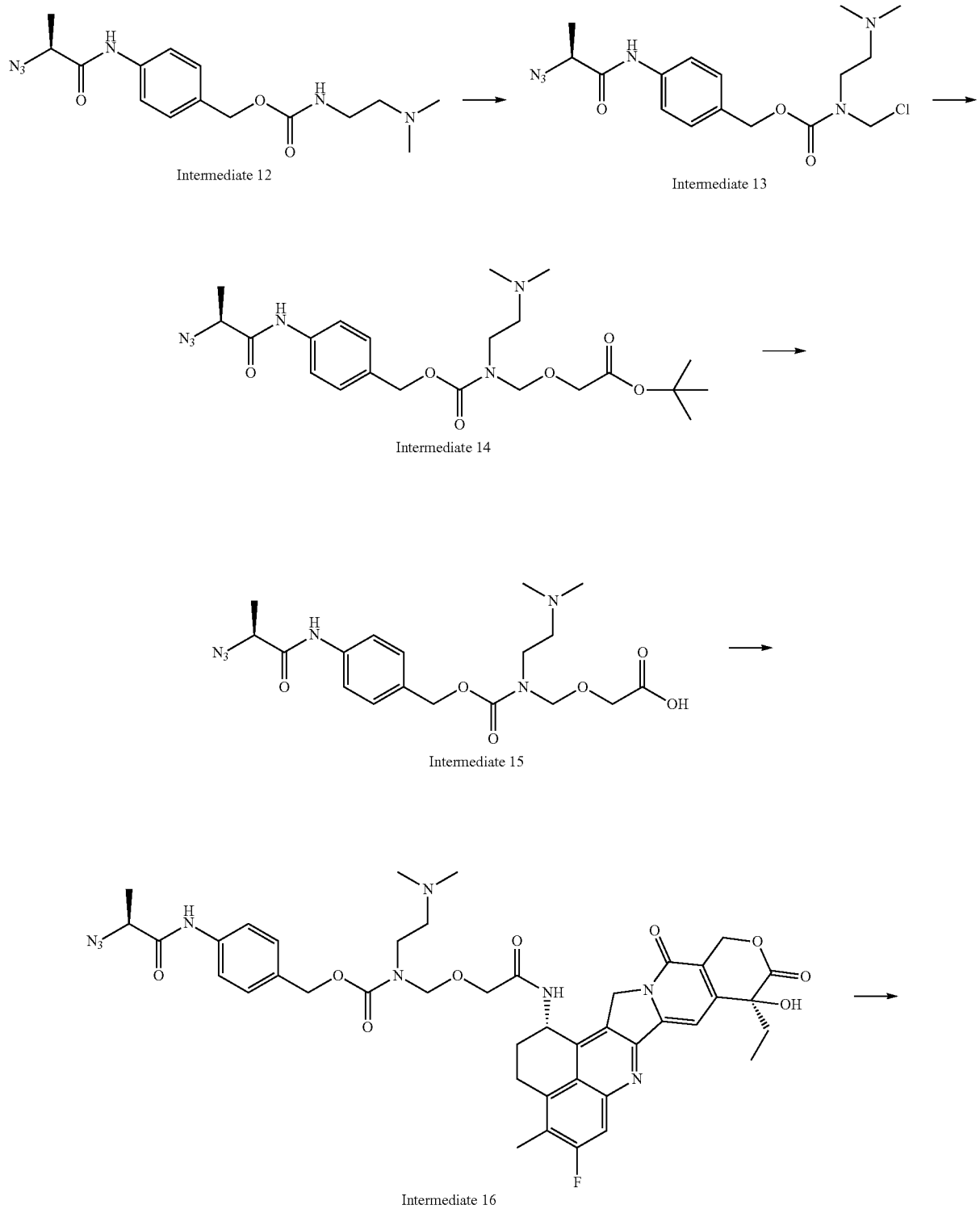

Intermediate 12

Intermediate 13

Intermediate 14

Intermediate 15

Intermediate 16

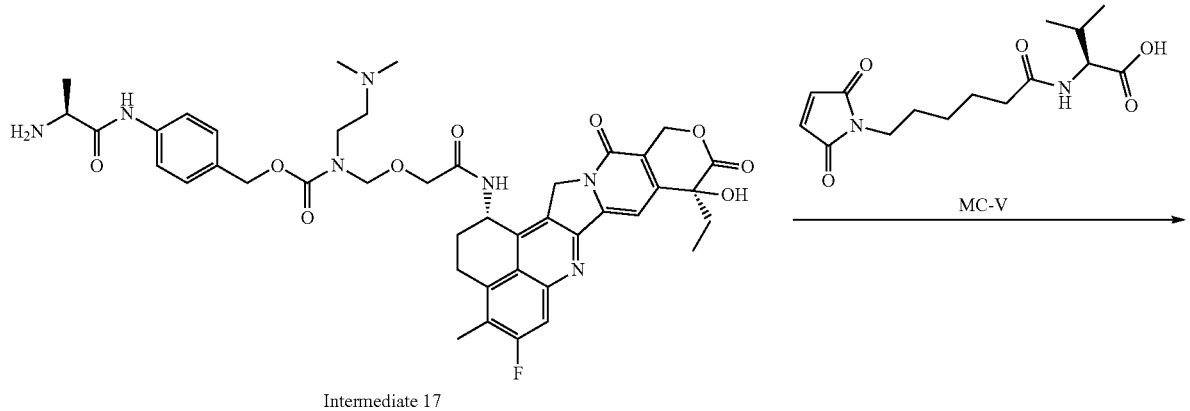

Intermediate 17

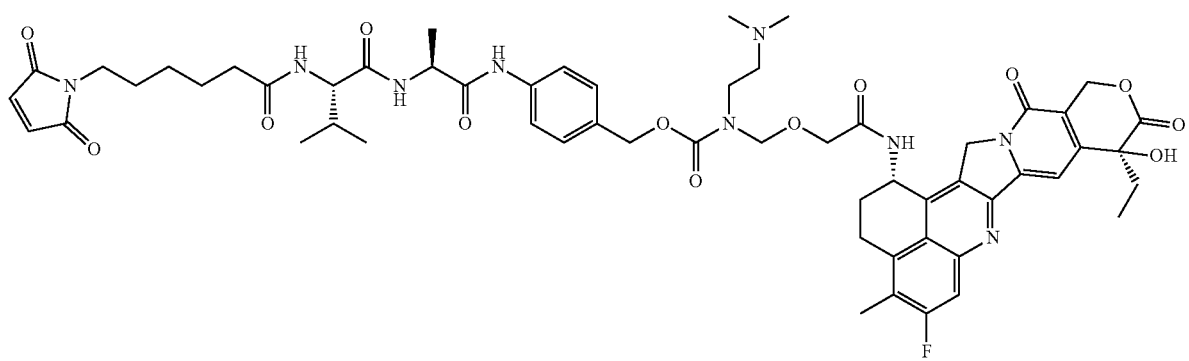

LE13

Synthesis of Intermediate 14

The commercially available intermediate 12 (267 mg, 0.8 mmol) was mixed with paraformaldehyde (50 mg, 1.6 mmol) and dissolved in 20 mL of anhydrous dichloromethane. Then, trimethylchlorosilane (0.3 mL, 3.4 mmol) was added slowly. After the addition was completed, the reaction was carried out at room temperature for 2 hours. Then, the reaction was monitored by liquid chromatography-mass spectrometry after sampling and quenching with methanol. After the reaction was completed, the reaction solution was filtered, and then tert-butyl 2-hydroxyacetate (211 mg, 1.6 mmol) and pempidine (0.5 mL) were added to the filtrate, and the reaction was continued at room temperature for about 2 hours. After the reaction was completed, most of the solvent was removed by distillation under reduced pressure, and the obtained crude product was purified by silica gel column chromatography [dichloromethane:methanol=20:1 (v/v)] to obtain intermediate 14 (260 mg, yield of 68%), ESI-MS m/z: 479 (M+H).

Synthesis of Intermediate 15

Intermediate 14 (238 mg, 0.50 mmol) was dissolved in 6 mL of a mixed solvent of dichloromethane and methanol (v/v=2:1), and 0.3 mL of trifluoroacetic acid was slowly added thereto, and the reaction was carried out at room temperature for 30 min. After the reaction was completed, an equal volume of water and ethyl acetate were added thereto, and the organic phase was dried and concentrated, and the obtained crude product was directly used in the next step.

Synthesis of Intermediate 16

The crude product obtained from the previous step was mixed with Exatecan methanesulfonate (170 mg, 0.30 mmol) in 5 mL of anhydrous N,N-dimethylformamide, and then 2-(7-azabenzotriazol-1-yl)-N,N,N',N'-tetramethyluronium hexafluorophosphate (341 mg, 0.90 mmol) and 0.60 mL of triethylamine were added thereto, and the reaction was carried out at room temperature for 2 hours. After the reaction was completed, the solvent was removed by distillation under reduced pressure, and then the obtained crude product was purified by silica gel column chromatography [chloroform:methanol=10:1 (v/v)] to obtain intermediate 16 (210 mg, yield of 83%), ESI-MS m/z: 840 (M+H).

Synthesis of Intermediate 17

Intermediate 16 (100 mg, 0.12 mmol) was dissolved in 15 mL of anhydrous tetrahydrofuran, and 3 mL of water was added thereto, then 0.3 mL of 1 mol/L triethylphosphine aqueous solution was added thereto, and the reaction was carried out at room temperature for 4 hours. After the reaction was monitored to be completed, the reaction mixture was distilled under reduced pressure to remove tetrahydrofuran. Sodium bicarbonate was added to the remaining aqueous solution to adjust the pH to neutral, and then dichloromethane was added for extraction. The obtained organic phase was dried and evaporated under reduced pressure to remove the solvent. The obtained crude product was purified by silica gel column chromatography [dichloromethane:methanol=10:1 (v/v)] to obtain intermediate 17 (69 mg, yield of 71%), ESI-MS m/z: 814 (M+H).

Synthesis of Compound LE13

Intermediate 17 (120 mg, 0.15 mmol) obtained according to the previous synthesis method was mixed with the commercially available raw material MC-V (102 mg, 0.33 mmol) in 40 mL of dichloromethane, and the condensation agent 2-ethoxy-1-ethoxycarbonyl-1,2-dihydroquinoline (82 mg, 0.33 mmol) was added to react overnight at room temperature. After the reaction was completed, the solvent was evaporated under reduced pressure and the obtained crude product was purified by silica gel column chromatography [dichloromethane:methanol=10:1 (v/v)] to obtain compound LE13 (116 mg, yield of 70%), ESI-MS m/z: 1106.5 (M+H).

Example 2-3: Synthesis of Compound LE14

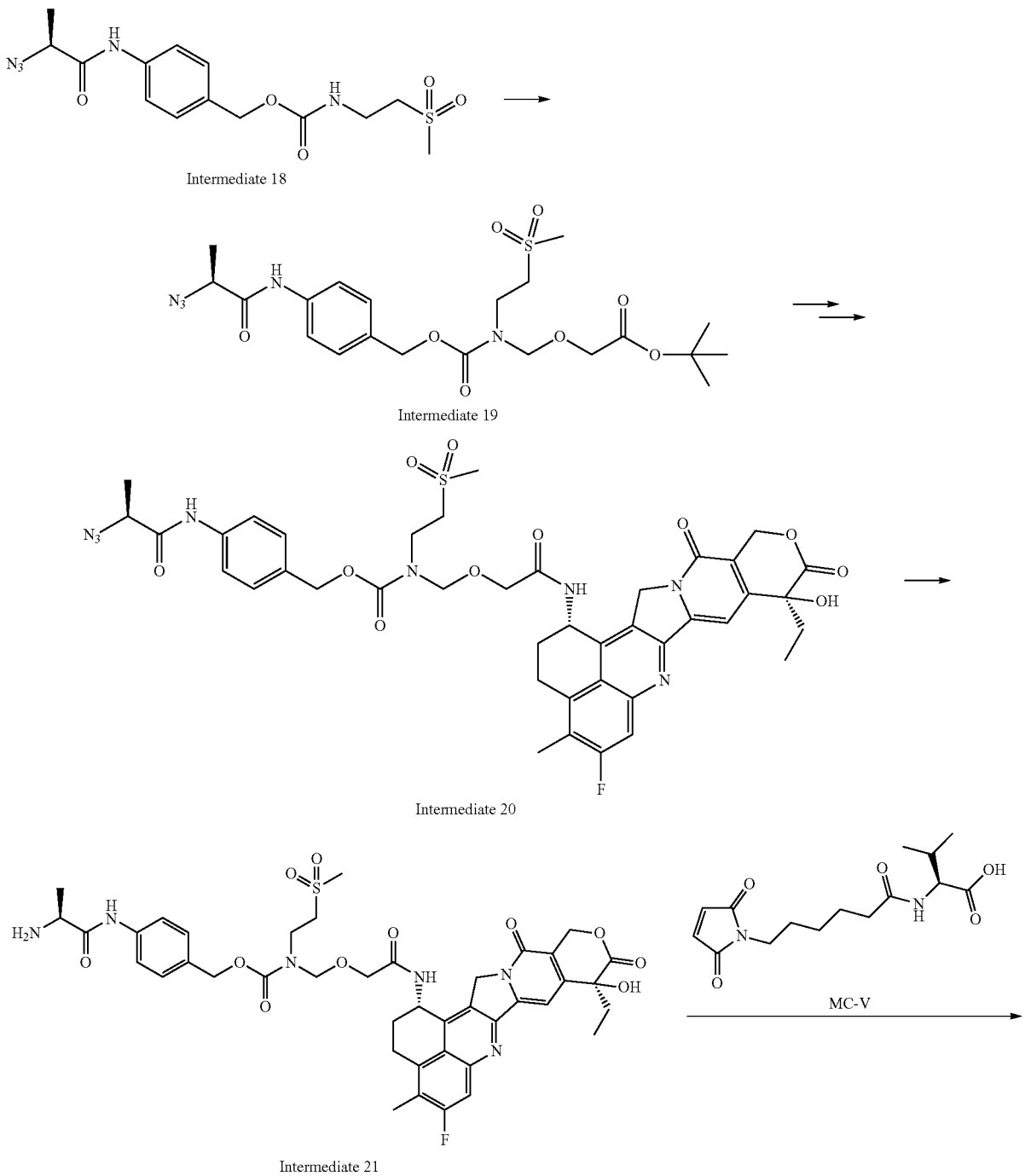

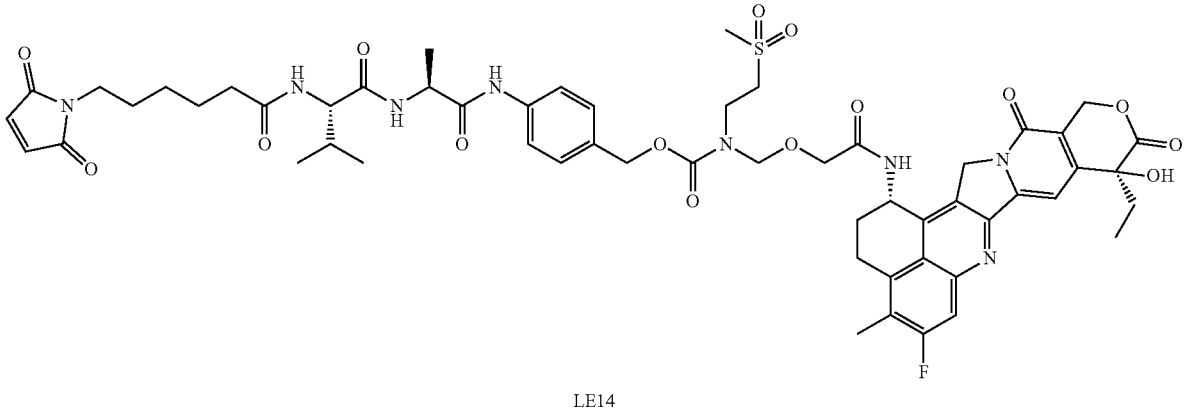 [SMILES: CC[C@@]1(O)C(=O)OCc2c1cc1n(c2=O)Cc2c-1nc1cc(F)c(C)c3c1c2[C@@H](NC(=O)COCN(CCS(C)(=O)=O)C(=O)OCc1ccc(NC(=O)[C@H](C)NC(=O)[C@@H](NC(=O)CCCCCN2C(=O)C=CC2=O)C(C)C)cc1)CC3]

LE14

Synthesis of Intermediate 19

The commercially available intermediate 18 (300 mg, 0.8 mmol) was mixed with paraformaldehyde (50 mg, 1.6 mmol) and dissolved in 20 mL anhydrous dichloromethane. Then, trimethylchlorosilane (0.3 mL, 3.4 mmol) was slowly added thereto, and the reaction was carried out at room temperature for 2 hours. The reaction was monitored by liquid chromatography-mass spectrometry after sampling and quenching with methanol. After the reaction was completed, the reaction mixture was filtered and then tert-butyl 2-hydroxyacetate (211 mg, 1.6 mmol) and triethylamine (0.22 mL, 1.6 mmol) were added to the filtrate. The reaction was continued at room temperature for about 2 hours. After the reaction was completed, most of the solvent was removed by distillation under reduced pressure and the obtained crude product was purified by silica gel column chromatography [dichloromethane:methanol=20:1 (v/v)] to obtain intermediate 19 (349 mg, yield of 85%), ESI-MS m/z: 514 (M+H), $^1$H NMR (400 MHz, CDCl$_3$) δ 8.13 (s, 1H), 7.56 (d, J=7.5 Hz, 2H), 7.35 (s, 2H), 5.14 (s, 2H), 4.91 (s, 2H), 4.25 (q, J=7.1 Hz, 1H), 3.99 (d, J=42.5 Hz, 2H), 3.85 (t, J=6.2 Hz, 2H), 3.40 (dd, J=18.5, 7.6 Hz, 2H), 2.89 (d, J=48.6 Hz, 3H), 1.65 (d, J=6.8 Hz, 3H), 1.46 (s, 9H).

Synthesis of Intermediate 20

Intermediate 19 (257 mg, 0.50 mmol) was dissolved in 6 mL of a mixed solvent of dichloromethane and methanol (v/v=2:1), and 0.3 mL of trifluoroacetic acid was slowly added thereto, and the reaction was carried out at room temperature for 30 min. After the reaction was completed, an equal volume of water and ethyl acetate were added thereto, and the organic phase was dried and concentrated, and the obtained crude product was directly used in the next step.

The obtained crude product was mixed with Exatecan methanesulfonate (170 mg, 0.30 mmol) in 5 mL of anhydrous N,N-dimethylformamide, and then 2-(7-azabenzotriazol-1-yl)-N,N,N',N'-tetramethyluronium hexafluorophosphate (341 mg, 0.90 mmol) and 0.60 mL of triethylamine were added thereto, and the reaction was carried out at room temperature for 2 hours. After the reaction was completed, the solvent was removed by distillation under reduced pressure, and then the obtained crude product was purified by silica gel column chromatography [dichloromethane:methanol=20:1 (v/v)] to obtain intermediate 20 (212 mg, yield of 81%), ESI-MS m/z: 875 (M+H). $^1$H NMR (400 MHz, CDCl$_3$) δ 8.27 (d, J=34.7 Hz, 1H), 7.63-7.35 (m, 5H), 7.21-7.10 (m, 1H), 5.71-5.48 (m, 2H), 5.24-4.95 (m, 3H), 4.95-4.72 (m, 4H), 4.45 (s, 1H), 4.33-3.97 (m, 3H), 3.75 (s, 2H), 3.39-2.99 (m, 4H), 2.76 (d, J=15.3 Hz, 3H), 2.43-2.15 (m, 5H), 2.04 (s, 1H), 1.94-1.75 (m, 2H), 1.62 (d, J=6.6 Hz, 3H), 1.11-0.89 (m, 3H).

Synthesis of Intermediate 21

Intermediate 20 (77 mg, 0.09 mmol) was dissolved in 12 mL of anhydrous tetrahydrofuran, and 3 mL of water was added thereto, then 0.3 mL of 1 mol/L triethylphosphine aqueous solution was added thereto, and the reaction was carried out at room temperature for 4 hours. After the reaction was completed, the reaction mixture was distilled under reduced pressure to remove tetrahydrofuran. Sodium bicarbonate was added to the remaining aqueous solution to adjust the pH to neutral, and then dichloromethane was added for extraction. The obtained organic phase was dried and evaporated under reduced pressure to remove the solvent. The obtained crude product was purified by silica gel column chromatography [dichloromethane:methanol=10:1 (v/v)] to obtain intermediate 21 (53 mg, yield of 69%), ESI-MS m/z: 849 (M+H). $^1$H NMR (400 MHz, DMSO) δ 8.52 (s, 1H), 7.79 (d, J=10.8 Hz, 1H), 7.67-7.55 (m, 2H), 7.47-7.21 (m, 3H), 6.51 (s, 1H), 5.60 (s, 1H), 5.52-5.32 (m, 2H), 5.30-5.11 (m, 2H), 5.11-4.94 (m, 2H), 4.94-4.74 (m, 2H), 4.02 (s, 2H), 3.81-3.66 (m, 2H), 3.60-3.35 (m, 4H), 3.24-3.08 (m, 2H), 2.94 (d, J=30.8 Hz, 3H), 2.39 (s, 3H), 2.28-2.04 (m, 2H), 2.00-1.73 (m, 2H), 1.22 (d, J=6.6 Hz, 3H), 0.96-0.70 (m, 3H).

Synthesis of Compound LE14

Intermediate 21 (134 mg, 0.16 mmol) was mixed with the commercially available raw material MC-V (102 mg, 0.33 mmol) in 40 mL of dichloromethane, and the condensation agent 2-ethoxy-1-ethoxycarbonyl-1,2-dihydroquinoline (82 mg, 0.33 mmol) was added to react overnight at room temperature. After the reaction was completed, the solvent was evaporated under reduced pressure and the obtained crude product was purified by silica gel column chromatography [dichloromethane:methanol=10:1 (v/v)] to obtain compound LE14 (137 mg, yield of 75%), ESI-MS m/z: 1141.4 (M+H). $^1$H NMR (400 MHz, DMSO) δ 9.97 (s, 1H), 8.52 (s, 1H), 8.27-8.09 (m, 1H), 7.88-7.70 (m, 2H), 7.63-7.51 (m, 2H), 7.28 (s, 3H), 6.99 (s, 2H), 6.51 (s, 1H), 5.59 (s, 1H), 5.50-5.32 (m, 2H), 5.17 (s, 2H), 4.98 (s, 2H), 4.85 (d, J=17.3 Hz, 2H), 4.43-4.33 (m, 1H), 4.21-4.12 (m, 1H), 4.03 (s, 2H), 3.74-3.64 (m, 2H), 3.20-3.03 (m, 3H), 3.02-2.84 (m, 4H), 2.36 (s, 3H), 2.23-2.09 (m, 4H), 2.01-1.90 (m, 1H), 1.90-1.78 (m, 2H), 1.55-1.39 (m, 4H), 1.30 (d, J=6.7 Hz, 3H), 1.23-1.11 (m, 2H), 0.93-0.77 (m, 9H).

Example 2-4: Synthesis of Compound LE15-LE20
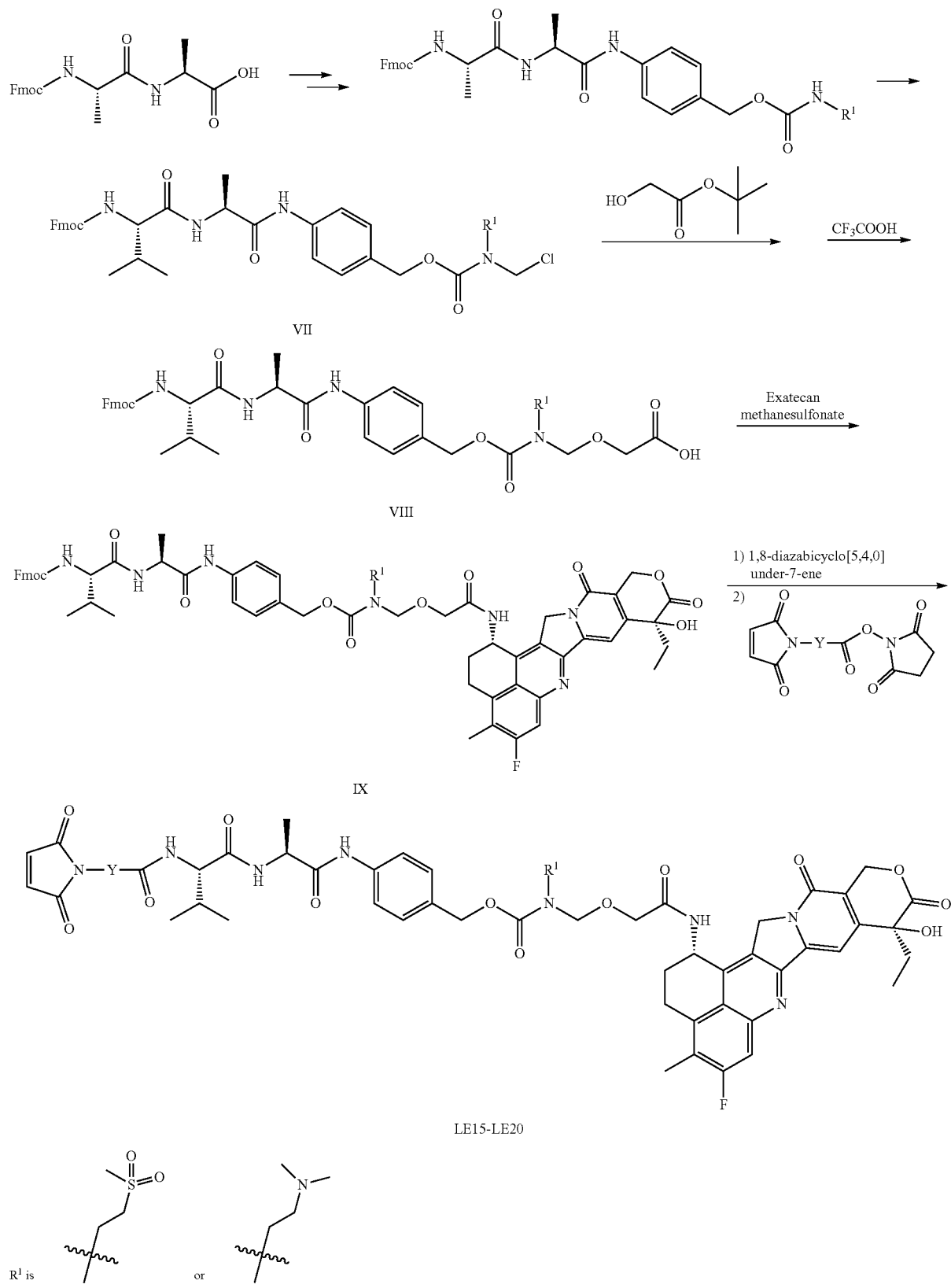

Intermediate VI could be prepared by replacing the methylamine hydrochloride in step b with the corresponding commercially available amino compound, using Fmoc-L-valyl-L-alanine as the starting material and referring to steps a and b in the synthesis method of intermediate 3 in Example 2-1. The subsequent steps were carried out starting from intermediate VI, and with the same methods as those in steps c, d, f, and h of Example 2-1, and intermediate IX similar to intermediate 9 was obtained. Then, following the same steps i and j as Example 6, the amino protecting group was removed, and the obtained product was condensed with different commercially available maleimide compounds to obtain the final product. The structures of the amino compounds and maleimides used are shown in Table 1. Compound LE15: gray-white solid, ESI-MS m/z: 1121.2 (M+H); compound LE16: light yellow solid, ESI-MS m/z: 1167.1 (M+H); compound LE17: yellow solid, ESI-MS m/z: 1132.3 (M+H); compound LE18: light yellow solid, ESI-MS m/z: 1305.4 (M+H); compound LE19: light yellow solid, ESI-MS m/z: 1307.4 (M+H); compound LE20: light yellow solid, ESI-MS m/z: 1337.6 (M+H).

TABLE 1

Intermediates used for the synthesis of LE15 to LE20

| Product | R¹ | Amino Compound | Maleimide Structure 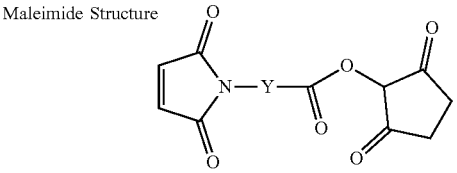 |
|---|---|---|---|
| LE15 | 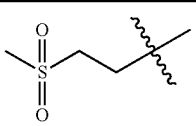 | Methylsulfonyl ethylamine hydrochloride | 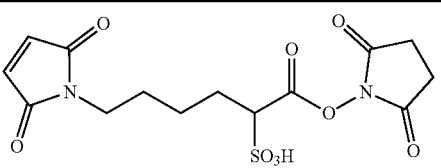 |
| LE16 | 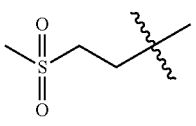 [SMILES: *CCS(C)(=O)=O] | Methylsulfonyl ethylamine hydrochloride | 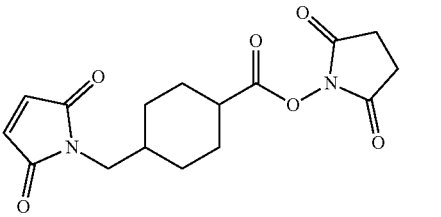 [SMILES: O=C(ON1C(=O)CCC1=O)C1CCC(CN2C(=O)C=CC2=O)CC1] |
| LE17 | 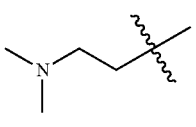 [SMILES: *CCN(C)C] | Dimethylethyl amine hydrochloride | 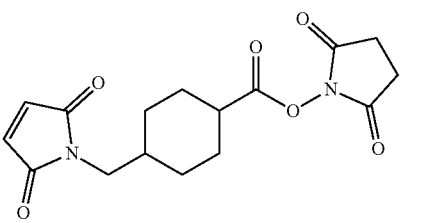 [SMILES: O=C(ON1C(=O)CCC1=O)C1CCC(CN2C(=O)C=CC2=O)CC1] |
| LE18 | 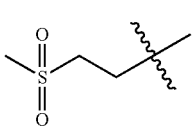 [SMILES: *CCS(C)(=O)=O] | Methylsulfonyl ethylamine hydrochloride | 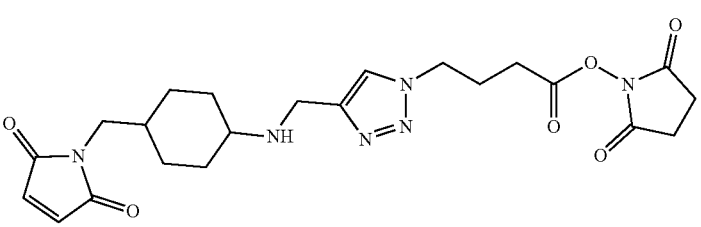 [SMILES: O=C(CCCn1cc(CNC2CCC(CN3C(=O)C=CC3=O)CC2)nn1)ON1C(=O)CCC1=O] |
| LE19 | 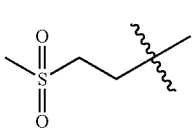 | Methylsulfonyl ethylamine hydrochloride | 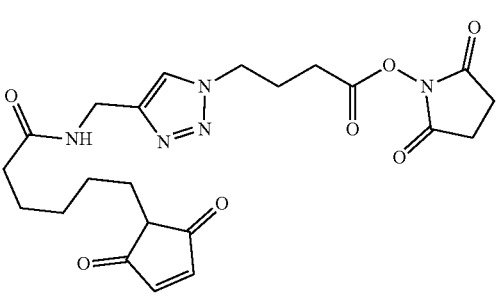 [SMILES: O=C(CCCCCC1C(=O)C=CC1=O)NCc1cn(CCCC(=O)ON2C(=O)CCC2=O)nn1] |

TABLE 1-continued
Intermediates used for the synthesis of LE15 to LE20
| Product | R¹ | Amino Compound | Maleimide Structure 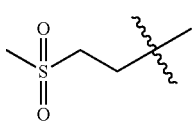 [SMILES: *CCS(C)(=O)=O] |
|---|---|---|---|
| LE20 | 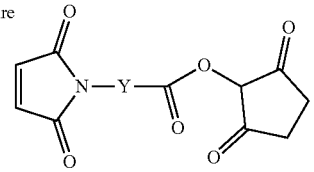 | Methylsulfonyl ethylamine hydrochloride | 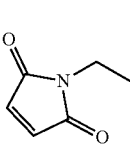 |
LE15
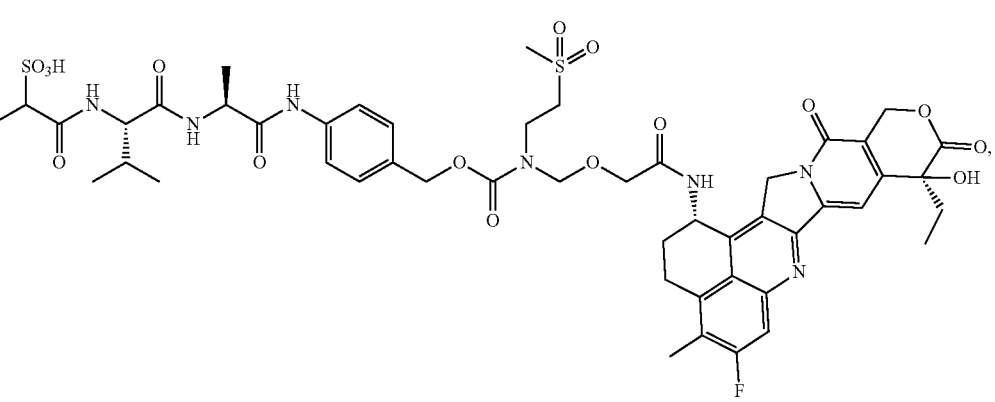
LE16
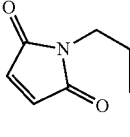

TABLE 1-continued
Intermediates used for the synthesis of LE15 to LE20
| Product | R¹ | Amino Compound | Maleimide Structure |
|---|---|---|---|
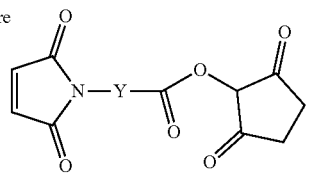
LE17
Example 2-5: Synthesis of Compounds LE21 and LE22
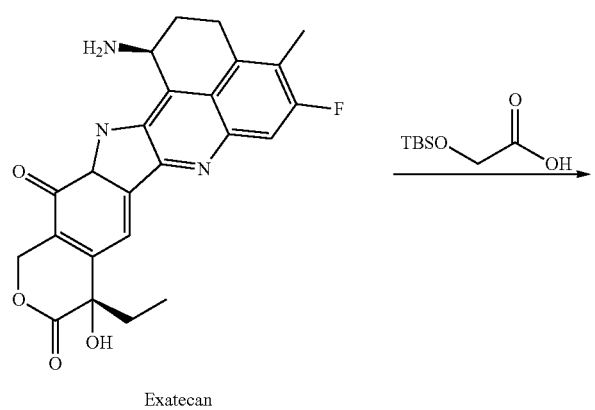
Exatecan

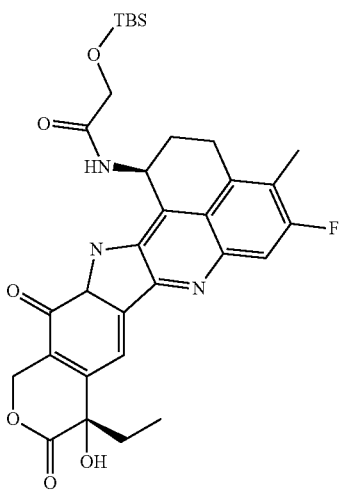

DXD-1

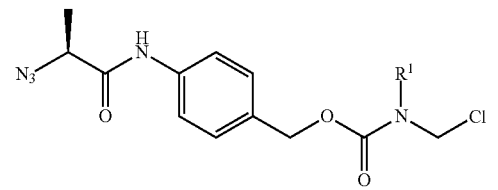

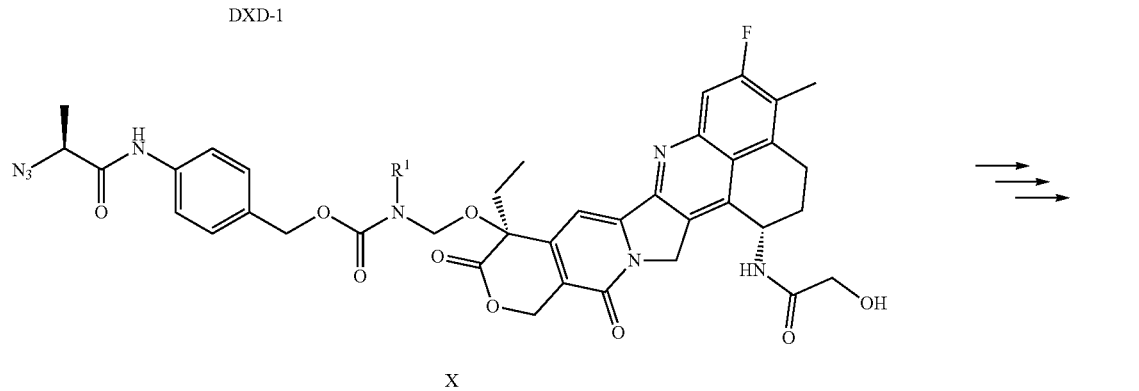

X

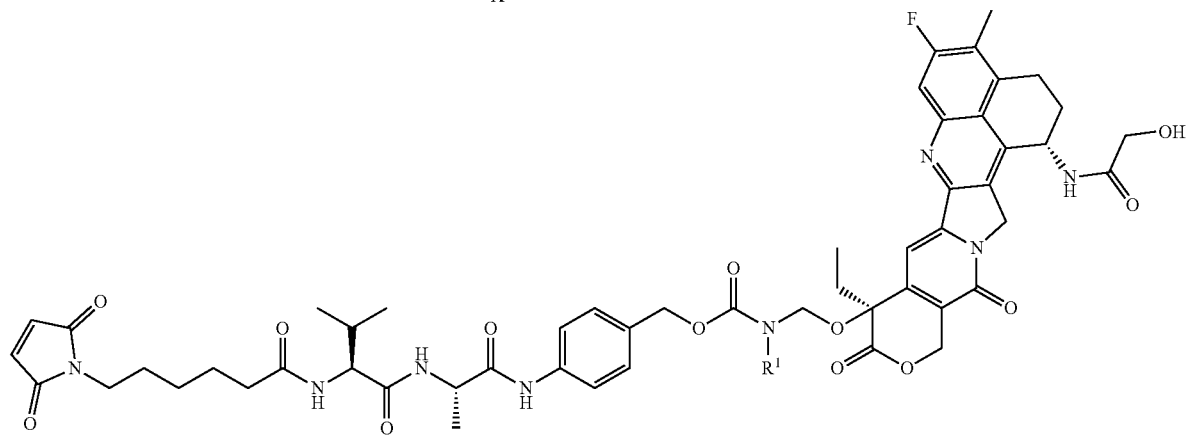

LE21-LE22

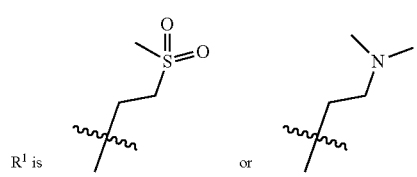

R¹ is

Synthesis of Compound DXD-1

Commercially available Exatecan methanesulfonate (0.568 g, 1 mmol) was mixed with commercially available 2-(tert-butyldimethylsilyloxy)acetic acid (CAS: 105459-05-0, 0.38 g, 2 mmol) in 20 mL anhydrous dichloromethane. The condensation agent HATU (0.76 g, 2 mmol) and 1 mL of pyridine were added thereto and stirred at room temperature for 2 hours. After the reaction was completed, the solvent was evaporated to dryness under reduced pressure, and the obtained crude product was purified by column chromatography [dichloromethane:methanol=50:1 (v/v)] to obtain title compound DXD-1 (0.55 g, yield of 90%), ESI-MS m/z: 608.1 (M+H). $^1$H NMR (400 MHz, CDCl$_3$) δ 7.73 (d, J=10.5 Hz, 1H), 7.64 (s, 1H), 7.05 (d, J=9.2 Hz, 1H), 5.80-5.62 (m, 2H), 5.41-5.14 (m, 4H), 4.29-4.15 (m, 2H), 4.08-4.03 (m, 1H), 3.27-3.07 (m, 2H), 2.45 (s, 3H), 2.38-2.28 (m, 2H), 1.96-1.81 (m, 2H), 1.04 (t, J=7.4 Hz, 3H), 0.80 (s, 9H), 0.11 (s, 3H), 0.03 (s, 3H).

Preparation of Intermediate V

Intermediate V could be prepared by replacing the methylamine hydrochloride in step b with the corresponding commercially available amino compound, referring to the preparation method of compound 4 in Example 2-1.

Synthesis of LE21 to LE22

Intermediate V was reacted with DXD-1, and then treated with 10% trifluoroacetic acid/dichloromethane solution to obtain intermediate X. Then, intermediate X was reacted according to the subsequent steps e, g, i, and j of compound 5 in Example 2-1: Intermediate X was reduced to obtain an amino compound, and the amino compound was then condensed with Fmoc-L-valine N-hydroxysuccinimide ester. Then the Fmoc protecting group of the amino group was removed from the obtained product, and the obtained amino product was then reacted with N-succinimidyl 6-maleimidohexanoate to obtain the final product. Compound LE21: yellow solid, ESI-MS m/z: 1141.2 (M+H); compound LE22: yellow solid, ESI-MS m/z: 1106.6 (M+H).

LE21

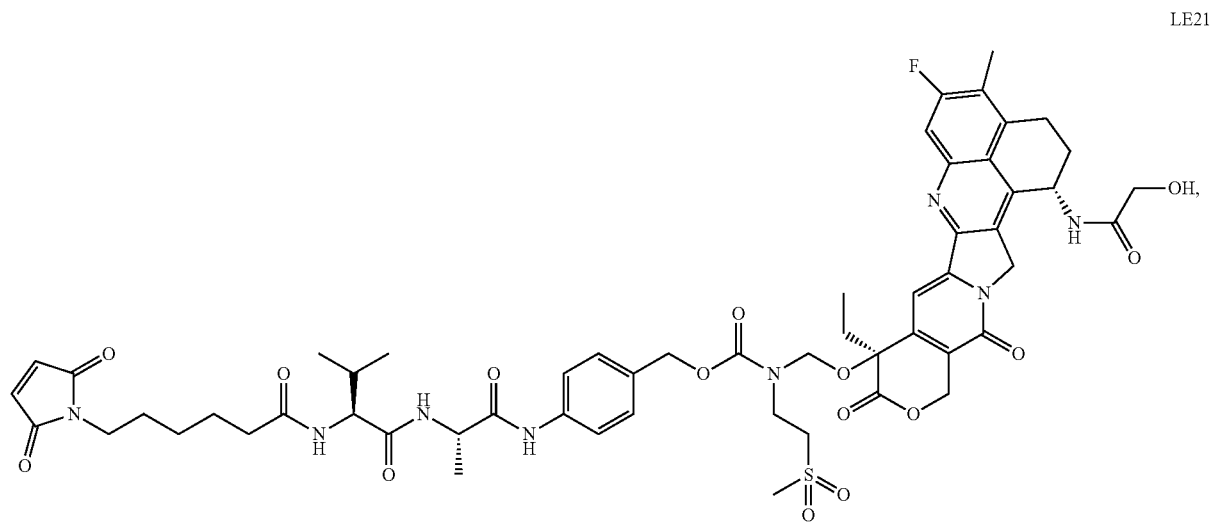

LE22

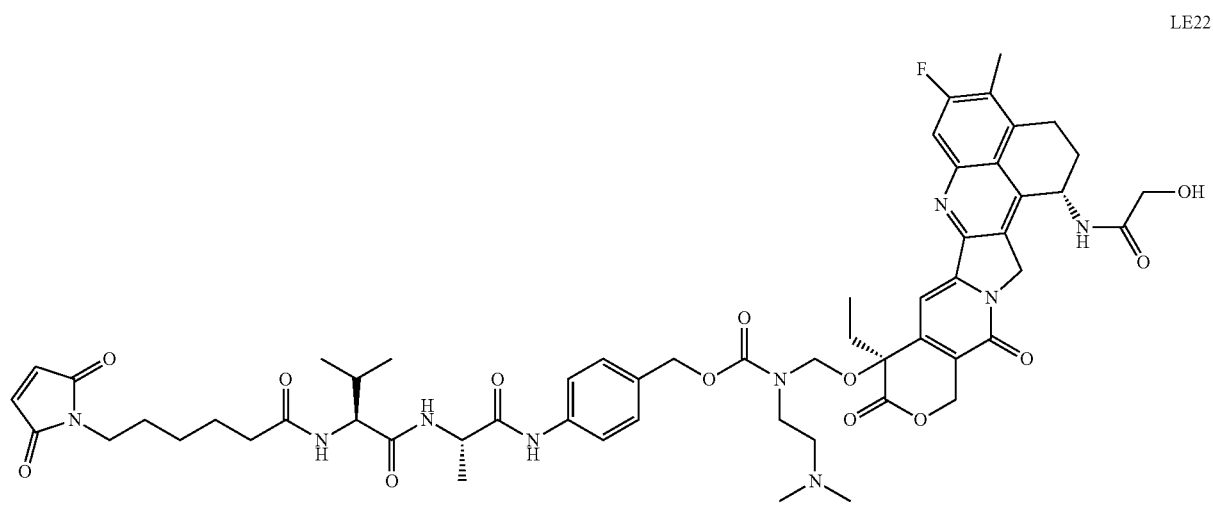

Example 2-6: Synthesis of Compound LS13

Referring to the synthesis method of LE1S in Examples 2 to 4, SN-38 (7-ethyl-10-hydroxycamptothecin) was reacted with intermediate VII (10 is methyl sulfonyl ethyl) to obtain compound LS13 after deprotection, condensation and other steps: $^1$H NMR (400 MHz, DMSO) δ 9.92 (d, J=22.4 Hz, 1H), 8.14 (s, 1H), 8.08 (d, J=9.1 Hz, 1H), 7.81 (d, J=8.0 Hz, 1H), 7.70-7.50 (m, 3H), 7.47 (d, J=7.2 Hz, 1H), 7.34 (d, J=7.2 Hz, 1H), 7.27 (s, 1H), 7.20 (s, 1H), 6.98 (s, 2H), 6.51 (s, 1H), 5.61 (s, 2H), 5.48-5.35 (m, 2H), 5.27 (s, 2H), 5.10 (d, J=20.6 Hz, 2H), 4.36 (s, 1H), 4.21-4.07 (m, 1H), 3.84 (s, 2H), 3.48 (s, 2H), 3.21-2.92 (m, 6H), 2.25-2.04 (m, 2H), 2.04-1.78 (m, 3H), 1.55-1.36 (m, 4H), 1.36-1.10 (m, 9H), 0.95-0.71 (m, 10H).

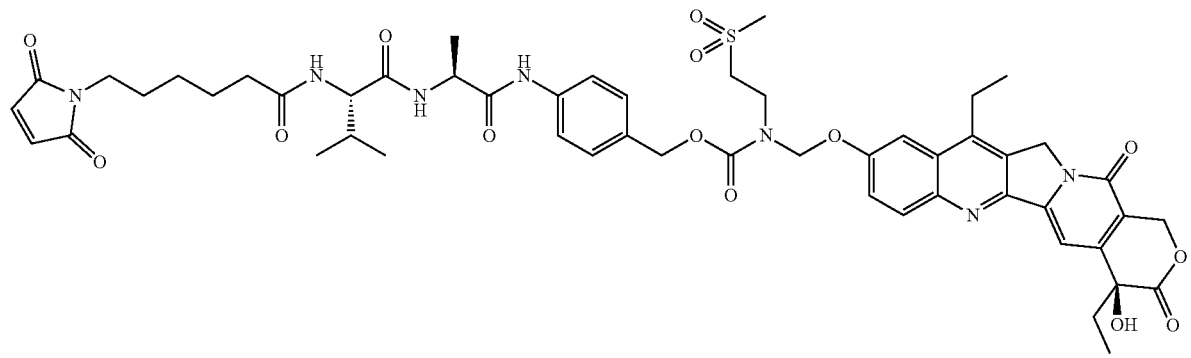

LS13

Example 2-7: Synthesis of Compound GGFG-Dxd

Compound GGFG-Dxd was prepared according to the known synthesis method reported in WO2015146132A1. ESI-MS m/z: 1034.5 (M+H), $^1$H-NMR (400 MHz, DMSO-$d_6$) δ 8.61 (t, J=6.4 Hz, 1H), 8.50 (d, J=8.5 Hz, 1H), 8.28 (t, J=5.1 Hz, 1H), 8.11 (d, J=7.5 Hz, 1H), 8.05 (t, J=5.7 Hz, 1H), 7.99 (t, J=5.9 Hz, 1H), 7.77 (d, J=11.0 Hz, 1H), 7.31 (s, 1H), 7.25-7.16 (m, 5H), 6.98 (s, 2H), 6.51 (s, 1H), 5.59 (dt, J=7.4, 4.1 Hz, 1H), 5.41 (s, 2H), 5.20 (s, 2H), 4.64 (d, J=6.1 Hz, 2H), 4.53-4.40 (m, 1H), 4.02 (s, 2H), 3.74-3.37 (m, 8H), 3.18-3.00 (m, 2H), 3.04-2.97 (m, 1H), 2.77 (dd, J=13.5, 9.4 Hz, 1H), 2.38 (s, 3H), 2.19 (dd, J=14.9, 8.5 Hz, 2H), 2.11-2.05 (m, 2H), 1.86 (dd, J=14.0, 6.7 Hz, 2H), 1.45 (s, 4H), 1.20-1.14 (m, 2H), 0.87 (t, J=7.1 Hz, 3H).

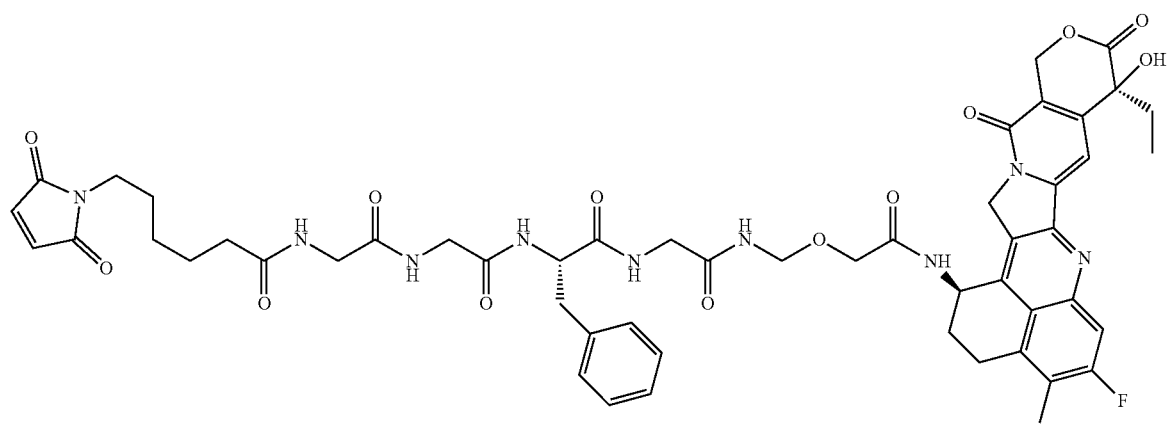

GGFG-Dxd

Example 3: Preparation of Antibody-Drug Conjugates

The antibodies FDA026, FDA028, and FDA029 against HER3 were prepared according to the method of Example 1 and were respectively exchanged into 50 mM PB/1.0 mM EDTA buffer (pH 7.0) using a G25 desalting column. 12 equivalents of TECP were added thereto and the mixture was stirred at 37° C. for 2 hours to fully open the disulfide bonds between the antibody chains. Then, phosphoric acid was used to adjust the pH of the reduced antibody solution to 6.0 and the temperature of the water bath was lowered to 25° C. for coupling reaction. The linker-drug conjugates LE12 to LE22, LS13, and GGFG-Dxd prepared according to the above Example 2 were dissolved in DMSO respectively and 12 equivalents of linker-drug conjugate were added dropwise to the reduced antibody solution. Additional DMSO was added to a final concentration of 10% (v/v) and the reaction was stirred at 25° C. for 0.5 hours. After the reaction was completed, the sample was filtered through a 0.22 μm membrane. The tangential flow filtration system was used to purify and remove unconjugated small molecules. The buffer was a 50 mM PB/1.0 mM EDTA solution (pH 6.0). After purification, a final concentration of 6% sucrose was added and stored in a −20° C. refrigerator. The absorbance values were measured at 280 nm and 370 nm by UV method, respectively, and the DAR value was calculated. The results are shown in Table 2 below.

The coupling reaction was carried out in the same manner as in this example and all samples were prepared according to the highest DAR (i.e., excessive coupling). The occurrence of precipitation during each coupling reaction was observed and the polymer ratio and recovery rate after each coupling reaction were calculated. The results are also shown in Table 2.

In practical research, it was found that the linker-drug conjugate GGFG-Dxd produces precipitation when coupled with other antibodies and has a high aggregation ratio, which is not universal. However, when the linker-drug conjugates of the present technical solution were attempted to be coupled with different antibodies, no precipitation was produced and the aggregation ratio was within the normal range, indicating that the linker-drug conjugates provided by the present disclosure have better physicochemical properties.

Effect Example 1: Evaluation of Binding Ability Between Antibody-Drug Conjugates and Antigens The binding ability of FDA026 antibody to Her3 antigen before and after conjugation with linker-drug conjugate LE12-LE22 was evaluated by competitive ELISA method. The specific method is as follows: 100 ng/mL HER3 antigen (purchased from Sino Biological, product number: 10201-H8H) was coated on a hydrophilic ELISA plate strip at 100 μL/well and blocked with 3% BSA at room temperature for 2 hours. 33 ng/mL biotin-labeled FDA026 antibody (DAR-2.82) was pre-mixed at a ratio of 1:1 with a series of final concentrations (100000, 10000, 1000, 400, 160, 64, 3.2, and 0.16 ng/mL) of FDA026 antibody and the antibody-drug conjugate prepared in Example 3, and then added to the ELISA plate coated with HER3 antigen. The plate was shaken horizontally at 200 rpm for 1 hour at room temperature. Pierce™ High Sensitivity Streptavidin-HRP, Pre-Diluted enzyme-linked antibody (Thermo, product number: 21134) (dilution ratio of 1:500) was added at 100 μL/well and Sigma's TMB color developing solution (Sigma, product number: T0440) was used for color development for 25 minutes before being terminated with 1 mol/L $H_2SO_4$. The reference wavelength of the microplate reader was 650 nm, and the absorbance reading was measured at 450 nm. The results (as shown in Table 3) showed that there was no difference in the binding activity to the HER3 antigen before and after coupling of the FDA026 antibody with the linker-drug conjugate. Using the same method, the binding ability of the antibodies FDA028 and FDA029 to the HER3 antigen before and after coupling with the linker-drug conjugate was evaluated separately. The results (as shown in Table 3) indicated that there was no difference in the binding activity to the HER3 antigen before and after coupling of the antibodies FDA028 and FDA029 with the linker-drug conjugate.

TABLE 2

Coupling conditions for preparing different antibody-drug conjugates (ADCs)

| ADC Number | Antibody | Linker-Drug Conjugate | DAR Value | Whether Precipitation | Aggregation Ratio | Recovery Rate |
|---|---|---|---|---|---|---|
| FDA026-1402 | FDA026 | GGFG-Dxd | 7.76 | No | 0.5% | 90% |
| FDA026-LE12 | FDA026 | LE12 | 7.56 | No | 0.6% | 88% |
| FDA026-LE13 | FDA026 | LE13 | 7.63 | No | 0.1% | 90% |
| FDA026-LE14 | FDA026 | LE14 | 7.81 | No | 0.1% | 92% |
| FDA026-LE15 | FDA026 | LE15 | 7.56 | No | 0.2% | 90% |
| FDA026-LE16 | FDA026 | LE16 | 7.83 | No | 0.2% | 82% |
| FDA026-LE17 | FDA026 | LE17 | 7.49 | No | 0.2% | 82% |
| FDA026-LE18 | FDA026 | LE18 | 7.60 | No | 0.3% | 93% |
| FDA026-LE19 | FDA026 | LE19 | 7.78 | No | 0.2% | 88% |
| FDA026-LE20 | FDA026 | LE20 | 7.65 | No | 0.2% | 84% |
| FDA026-LE21 | FDA026 | LE21 | 7.83 | No | 0.3% | 91% |
| FDA026-LE22 | FDA026 | LE22 | 7.72 | No | 0.4% | 89% |
| FDA026-LS13 | FDA026 | LS13 | 7.68 | No | 0.5% | 92% |
| FDA028-LE12 | FDA028 | LE12 | 7.67 | No | 0.6% | 88% |
| FDA028-LE13 | FDA028 | LE13 | 7.59 | No | 0.1% | 90% |
| FDA028-LE14 | FDA028 | LE14 | 7.63 | No | 0.1% | 92% |
| FDA029-LE12 | FDA029 | LE12 | 7.72 | No | 0.3% | 89% |
| FDA029-LE13 | FDA029 | LE13 | 7.67 | No | 0.2% | 91% |
| FDA029-LE14 | FDA029 | LE14 | 7.82 | No | 0.2% | 90% |

"/" indicates that the recovery rate is not calculated

TABLE 3

Data on the binding activity of HER3 antibody to HER3 before and after coupling with linker-drug conjugate

| $OD_{450-650}$ | Concentration ng/ml | | | | | | | |
|---|---|---|---|---|---|---|---|---|
| | 100000 | 10000 | 1000 | 400 | 160 | 64 | 3.2 | 0.32 |
| Antibody FDA026 | 0.051 | 0.1 | 0.319 | 1.254 | 2.845 | 3.573 | 3.766 | 3.586 |
| FDA026-LE12 | 0.046 | 0.11 | 0.33 | 1.253 | 2.794 | 3.567 | 3.745 | 3.546 |
| FDA026-LE13 | 0.054 | 0.09 | 0.32 | 1.247 | 2.764 | 3.613 | 3.756 | 3.596 |
| FDA026-LE14 | 0.06 | 0.098 | 0.347 | 1.173 | 2.722 | 3.507 | 3.673 | 3.616 |
| FDA026-LE15 | 0.052 | 0.11 | 0.33 | 1.25 | 2.85 | 3.58 | 3.766 | 3.58 |
| FDA026-LE16 | 0.045 | 0.11 | 0.32 | 1.24 | 2.784 | 3.557 | 3.735 | 3.556 |
| FDA026-LE17 | 0.055 | 0.09 | 0.33 | 1.253 | 2.767 | 3.623 | 3.766 | 3.58 |
| FDA026-LE18 | 0.06 | 0.099 | 0.35 | 1.176 | 2.73 | 3.517 | 3.663 | 3.676 |
| FDA026-LE19 | 0.053 | 0.011 | 0.035 | 1.182 | 2.83 | 3.521 | 3.665 | 3.681 |
| FDA026-LE20 | 0.051 | 0.01 | 0.035 | 0.179 | 2.77 | 3.632 | 3.712 | 3.562 |
| FDA026-LE21 | 0.056 | 0.089 | 0.365 | 1.182 | 2.783 | 3.567 | 3.723 | 3.602 |
| FDA026-LE22 | 0.066 | 0.088 | 0.344 | 1.234 | 2.812 | 3.516 | 3.716 | 3.613 |
| Antibody FDA028 | 0.053 | 0.11 | 0.33 | 1.25 | 2.86 | 3.56 | 3.78 | 3.53 |
| FDA028-LE12 | 0.051 | 0.13 | 0.31 | 1.26 | 2.79 | 3.61 | 3.77 | 3.54 |
| FDA028-LE13 | 0.055 | 0.012 | 0.32 | 1.26 | 2.78 | 3.62 | 3.72 | 3.55 |
| FDA028-LE14 | 0.06 | 0.099 | 0.34 | 1.25 | 2.77 | 3.63 | 3.75 | 3.62 |
| Antibody FDA029 | 0.055 | 0.13 | 0.32 | 1.23 | 2.79 | 3.61 | 3.77 | 3.53 |
| FDA029-LE12 | 0.053 | 0.11 | 0.357 | 1.272 | 2.781 | 3.651 | 3.765 | 3.63 |
| FDA029-LE13 | 0.062 | 0.09 | 0.361 | 1.278 | 2.763 | 3.631 | 3.771 | 3.64 |
| FDA029-LE14 | 0.05 | 0.11 | 0.372 | 1.281 | 2.771 | 3.661 | 3.782 | 3.65 |

Effect Example 2: In Vitro Killing Activity Evaluation of Antibody-Drug Conjugates SK-BR-3 (ATCC) cells were selected as the cell line for in vitro activity detection. 2000 cells per well were seeded in a 96-well cell culture plate and cultured for 20 to 24 hours. The antibody-drug conjugates prepared according to the method of Example 3 were formulated into test solutions with 11 concentration gradients of 1000, 166.7, 55.6, 18.6, 6.17, 2.06, 0.69, 0.08, 0.008, and 0 nM using L15 cell culture medium containing 10% FBS. The diluted test solutions were added to the culture plate containing the seeded cells at 100 μL/well and incubated for 144 hours at 37° C. in a 5% $CO_2$ incubator. CellTiter-Glo® Luminescent Cell Viability Assay Reagent (50 μL/well) was added and the plate was shaken at 500 rpm at room temperature for 10 minutes to mix well. The data were read using a SpectraMaxL microplate reader (OD 570 nm, reading at 2 s intervals) and the IC50 results were calculated as shown in Table 4.

Using the same method as above, the cytotoxic killing activity of each antibody-drug conjugate against multiple tumor cells purchased from ATCC including 22Rv1, LNCaP, SW620, NCI-H820, OVCAR-8, and HCC827 was tested. The results are shown in Table 4. From the results in Table 4, it can be seen that the antibody-drug conjugates provided by the present disclosure have excellent in vitro cytotoxic activity against SK-BR-3, 22Rv1, LNCaP, SW620, NCI-H820, OVCAR-8, and HCC827 cells, etc.

TABLE 4

In vitro killing activity of antibody-drug conjugates

| ADC Number | IC50 (nM) | | | | | | |
|---|---|---|---|---|---|---|---|
| | SK-BR-3 Cell | 22Rv1 Cell | LNCaP Cell | SW620 Cell | NCI-H820 Cell | OVCAR-8 Cell | HCC827 Cell |
| FDA026-LE12 | 37.8 | 52.32 | 97.64 | 56.33 | 38.67 | Not Tested | Not Tested |
| FDA026-LE13 | 42.4 | 64.36 | 87.77 | 67.54 | Not Tested | 54.33 | Not Tested |
| FDA026-LE14 | Not Tested | 37.5 | 85.6 | 36.5 | 38.4 | 50.23 | 62.38 |
| FDA026-LE15 | 53.12 | Not Tested | Not Tested | 47.86 | Not Tested | Not Tested | Not Tested |
| FDA026-LE16 | 46.18 | Not Tested | Not Tested | 53.12 | Not Tested | Not Tested | Not Tested |
| FDA026-LE17 | 40.36 | Not Tested | Not Tested | 42.38 | Not Tested | Not Tested | Not Tested |
| FDA026-LE18 | 45.32 | Not Tested | Not Tested | 41.69 | Not Tested | Not Tested | Not Tested |
| FDA026-LE19 | 52.38 | Not Tested | Not Tested | 40.28 | Not Tested | Not Tested | Not Tested |
| FDA026-LE20 | 46.15 | Not Tested | Not Tested | 52.33 | Not Tested | Not Tested | Not Tested |
| FDA026-LE21 | 46.3 | 98.26 | Not Tested | Not Tested | 89.45 | Not Tested | Not Tested |
| FDA026-LE22 | 52.7 | 87.65 | Not Tested | Not Tested | 78.44 | 89.34 | 96.75 |
| FDA026-1402 | 43.2 | 36.9 | 93.26 | 40.20 | 41.64 | 55.46 | 70.75 |
| FDA026-LS13 | >1 μM | >600 | Not Tested | >500 | Not Tested | Not Tested | Not Tested |
| FDA028-LE12 | 38.2 | 55.3 | 96.5 | 56.45 | 38.76 | Not Tested | Not Tested |
| FDA028-LE13 | 42.4 | 65.2 | 88.23 | 67.82 | Not Tested | 54.45 | Not Tested |
| FDA028-LE14 | Not Tested | 37.2 | 93.28 | 41.2 | 43.12 | 55.75 | 70.13 |

TABLE 4-continued

In vitro killing activity of antibody-drug conjugates

| ADC Number | IC50 (nM) | | | | | | |
|---|---|---|---|---|---|---|---|
| | SK-BR-3 Cell | 22Rv1 Cell | LNCaP Cell | SW620 Cell | NCI-H820 Cell | OVCAR-8 Cell | HCC827 Cell |
| FDA029-LE12 | 38.45 | 55.34 | 96.8 | 56.52 | 38.68 | Not Tested | Not Tested |
| FDA029-LE13 | 42.35 | 66.1 | 88.34 | 67.75 | Not Tested | 54.56 | Not Tested |
| FDA029-LE14 | Not Tested | 37.6 | 93.32 | 41.6 | 43.23 | 55.87 | 70.25 |

Effect Example 3: Effects of Mutations at Fc-Terminal of Antibodies in Antibody-Drug Conjugates on Binding Activity and Cytotoxicity of Cells Expressing CD32a Receptors Effect Example 3-1: Effects of Mutations at Fc-Terminal of Antibodies in Antibody Drug Conjugates on Binding Activity of Cells Expressing CD32a Receptors Using the HTRF method to analyze the binding ability of the prepared ADC to cells expressing CD32a, HEK293 cells (ATCC) were quickly shaken in a 37° C. water bath to resuscitate the cells, centrifuged and the supernatant was removed, and 1.1 mL of 1× Tag-lite buffer was added to resuspend. 10 µL of cells were seeded into a 384-well plate per well. Then, in the wells where cells were added, pre-prepared antibody-drug conjugate samples such as FDA026-LE14, FDA028-LE14, and FDA029-LE14 were added at a series dilution concentration (100000, 3333.33, 1111.11, 370.37, 123.46, 41.15, 13.72, 4.57, and 1.52 nM) at 5 µL per well into a 384-well plate. Finally, 5 µL of d2-labeled immunoglobulin IgG-d2 conjugate was added to each well of the above plate. This IgG-d2 conjugate could bind to CD32a and was incubated for 3 hours at room temperature in the dark to produce a FRET signal. After adding the above ADC samples to the plate, the ADC samples could competitively bind to CD32a with labeled IgG, reducing its FRET signal. Readings were taken using a SpectraMax Paradigm microplate reader with an excitation wavelength of 340 nm, a reference wavelength of 616 nm and a characteristic emission wavelength of 665 nm. The absorbance was measured and its IC50 value was calculated. The results are shown in Table 5. The binding ability of each antibody-drug conjugate to CD32 is shown in Table 5; compared with FDA026-LE14 that has not been modified, the binding ability of FDA028-LE14 and FDA029-LE14 that have been modified in Fc-terminal amino acids is weaker (about 10%); indicating that the binding of antibody-drug conjugates modified in Fc-terminal amino acids to CD32a is weaker.

TABLE 5

Binding ability of antibody-drug conjugates to CD32a before and after Fc-terminal amino acid modification

| ADC Number | IC50 value (nM) 293 Cell |
|---|---|
| FDA026-LE14 | 52.69 |
| FDA028-LE14 | 523.81 |
| FDA029-LE14 | 535.42 |

Effect Example 3-2: Effects of Mutations at Fc-Terminal of Antibodies in Antibody-Drug Conjugates on Cytotoxicity of Cells Expressing CD32a Receptors K562 (ATCC) cells positively expressing FcγRIIa (note that the cells did not express HER3 antigen) were selected as the experimental cell line for in vitro activity detection. 5000 cells per well were seeded in a 96-well cell culture plate and cultured for 16 to 20 hours. The antibody-drug conjugates FDA026-LE14, FDA028-LE14, and FDA029-LE14 prepared as above were formulated into test solutions with 11 concentration gradients of 1000, 166.7, 55.6, 18.6, 6.17, 2.06, 0.69, 0.23, 0.08, 0.008, and 0 nM using L15 cell culture medium containing 10% FBS. The diluted test solutions were added to the culture plate containing the seeded cells at 100 µL/well and incubated for 144 hours at 37° C. in a 5% $CO_2$ incubator. CellTiter-Glo® Luminescent Cell Viability Assay Reagent (50 µL/well) was added and the plate was shaken at 500 rpm at room temperature for 10 minutes to mix well for 10 minutes. The data were read using a SpectraMaxL microplate reader (OD 570 nm, reading at 2 s intervals) and the IC50 results were calculated as shown in Table 5. The results show that FDA026-LE14 conjugated drugs without Fc modification have certain killing effects on K562 cells, while the killing activities of ADC drugs FDA028-LE14 and FDA029-LE14 modified with Fc modification are significantly reduced.

Using the same experimental method as the above K562 cell line, HSC cells differentiated for 4 days (purchased from stem cell company, product number: 70008.1) were selected and treated with the drug for 6 days for cytotoxic activity detection. After 6 days of treatment with antibody-drug conjugates, flow analysis of HSC cells showed that their surface antigen abundance (i.e., binding ratio, CD32a 7.4; HER3 antigen 0.8; CD34 69.0) showed high expression of CD32 and almost no expression of HER3 antigen. The results of the activity measurement are shown in Table 6. The results show that FDA026-LE14 conjugated drugs without Fc modification have certain killing effects on HSC cells, while the killing activities of ADC drugs FDA028-LE14 and FDA029-LE14 with Fc modification are significantly reduced.

TABLE 6

Evaluation of the killing activity of antibody-drug conjugates before and after modification of Fc-terminal amino acid on K562 and HSC cells

| ADC Number | IC50 value (nM) | |
|---|---|---|
| | K562 Cell | HSC Cell |
| FDA026-LE14 | 16.65 | 31.6 |
| FDA028-LE14 | 270.42 | 334 |
| FDA029-LE14 | 323.35 | 363 |

Effect Example 4: In Vitro Plasma Stability Assay

This example evaluates the stability of the antibody-drug conjugate prepared according to the method of Example 3 in human plasma. Specifically, in this example, the antibody-drug conjugate of Example 3 was added to human plasma and placed in a 37° C. water bath for 1, 3, 7, 14, 21, and 28 days. An internal standard (Exatecan as an internal standard substance) was added and extracted and then detected by high-performance liquid chromatography to detect the release of free drugs. The results are shown in Table 7.

TABLE 7

Stability evaluation of different ADCs in human plasma

| Sample Name | Free Drug Ratio | | | | | |
|---|---|---|---|---|---|---|
| | Day 1 | Day 3 | Day 7 | Day 14 | Day 21 | Day 28 |
| FDA026-1402 | 0.2% | 0.5% | 0.8% | 1.3% | 1.5% | 2.2% |
| FDA026-LE12 | 0.2% | 0.6% | 0.7% | 1.3% | 1.5% | 2.2% |
| FDA026-LE13 | 0.1% | 0.5% | 0.6% | 1.2% | 1.4% | 2.3% |
| FDA026-LE14 | 0.1% | 0.2% | 0.5% | 1.1% | 1.3% | 2.0% |
| FDA026-LS13 | 0.3% | 0.7% | 2.3% | 3.8% | 4.2% | 5.2% |
| FDA028-LE12 | 0.2% | 0.5% | 0.6% | 1.2% | 1.4% | 2.1% |
| FDA028-LE13 | 0.1% | 0.7% | 0.6% | 1.3% | 1.3% | 2.2% |
| FDA028-LE14 | 0.1% | 0.3% | 0.5% | 1.1% | 1.2% | 2.0% |
| FDA029-LE12 | 0.2% | 0.5% | 0.6% | 1.1% | 1.3% | 2.2% |
| FDA029-LE13 | 0.1% | 0.7% | 0.5% | 1.2% | 1.2% | 2.2% |
| FDA029-LE14 | 0.1% | 0.2% | 0.4% | 1.0% | 1.1% | 2.1% |

The plasma stability results show that the stability of the ADC obtained using the new technical solution is not inferior to FDA026-1402, and some are even better. At the same time, the above activity test results also prove that some of the newly obtained ADCs have better activity than FDA026-1402.

Effect Example 5: In Vitro Enzyme Digestion Experiment of Linker-Drug Conjugates The linker-drug conjugate (LE14 and GGFG-Dxd) was co-incubated with tissue proteinase B in three different pH (5.0, 6.0, 7.0) buffers. Samples were taken at different time points and entered into a high-performance liquid chromatography-mass spectrometry instrument. The external standard method (with DXD as the external standard) was used to determine the release percentage of the drug. The experimental results (as shown in Table 8) show that GGFG-Dxd has a slow speed of enzyme digestion within the pH range used, while LE14 of the present disclosure can be quickly enzymatically digested within the pH range of 5.0 to 7.0.

TABLE 8

In vitro enzyme digestion of LE14 and GGFG-Dxd at different pH

| | Percentage of drug release in the sample % | | | | | |
|---|---|---|---|---|---|---|
| | GGFG-Dxd | | | LE14 | | |
| Time (h) | pH 5.0 | pH 6.0 | pH 7.0 | pH 5.0 | pH 6.0 | pH 7.0 |
| 0 | 21.62 | 23.58 | 22.98 | 15 | 14.28 | 17.59 |
| 1 | 25 | 24.8 | 26.53 | 96.93 | 95.98 | 98.05 |
| 2 | 25.85 | 27.02 | 29.52 | 98.35 | 96.8 | 99.08 |
| 3 | 27.76 | 29.29 | 31.95 | 99.01 | 98.45 | 99.33 |
| 4 | 29.72 | 31.37 | 34.78 | 99.21 | 98.81 | 99.2 |
| 5 | 31.69 | 33.05 | 36.17 | 99.32 | 98.9 | 100 |
| 6 | 34.17 | 35.95 | 38.25 | 97.39 | 99 | 99.39 |

Effect Example 6: In Vitro Enzyme Digestion Experiment of FDA026-LS13

SK-BR-3 cell line was selected as the experimental cells. After the sample was incubated in tissue proteinase B system (100 mM sodium acetate-acetic acid buffer, 4 mM dithiothreitol, pH 5.0) at 37° C. for 4 hours, the obtained sample was diluted with culture medium to different concentrations. 8 concentrations (1.5 to 10-fold dilution) were set from 70 nM to 0.003 nM of SN-38 concentration. The killing (inhibitory) ability on the cell line was observed for 144 hours. The IC50 value was calculated by reading the fluorescence data after chemical luminescent staining with CellTiter-Glo® Luminescent Cell Viability Assay.

The above enzyme digestion samples obtained by incubating in a tissue proteinase B system at 37° C. for 4 hours were precipitated with an appropriate amount of ethanol to remove protein and detected by high-performance liquid chromatography to release small molecule compounds. The 4-hour release rate was measured with an equal amount of SN-38 as a reference, and the results showed that the release rate reached 99%.

The experimental results (as shown in Table 9) show that after enzyme digestion treatment, the cytotoxic activity of FDA026-LS13 is almost the same as that of SN-38 at an equivalent dose, which also indicates that FDA026-LS13 has almost completely released SN-38 under the action of tissue proteinase B and played a role. However, FDA026-LS13 may have undergone unpredictable changes when it is endocytosed into lysosomes, resulting in SN-38 not being able to function effectively.

TABLE 9

Changes in killing activity of FDA026-LS13 on NCI-N87 cell line before and after enzyme digestion by tissue proteinase B system

| | IC50 (based on SN-38 equivalent, nM) | |
|---|---|---|
| Sample | Before Enzyme Digestion | After Enzyme Digestion |
| FDA026-LS13 | >100 nM | 6.56 nM |
| SN-38 | 7.13 nM | 7.32 nM |

Effect Example 7: Testing Antitumor Activity of FDA026-LE14 in SW620 Human Colorectal Cancer Model 6 to 8 week old female Balb/c nude mice were subcutaneously injected with $5 \times 10^6$ human colorectal cancer cells (SW620) dissolved in 100 μL of PBS solution on the right side of the neck and back. When the tumor grew to an average volume of 150 to 200 mm³, mice were randomly divided into 8 groups according to tumor size and mouse weight, with 6 animals in each group. The groups were blank control group, Irinotecan hydrochloride group (100 mg/kg), and antibody-drug conjugate FDA026-1402, FDA028-LE14 and FDA026-LE14, respectively, with two dose groups of 5.0 mg/kg and 10.0 mg/kg, administered intraperitoneally once a week. The animal weight and tumor volume were measured twice a week, and the survival status of the experimental animals was observed during the experiment process. As shown in Table 9, the average tumor volume of the Irinotecan hydrochloride (100 mg/kg) treatment group was 1120.09 mm³ on the 14th day after the end of treatment (i.e., the 46th day of observation, same below), while the average tumor volume of the blank control group was 2074.5 mm³ at the end of treatment. The average tumor volume of the FDA026-1402 treatment group at 5.0 mg/kg was 260.87 mm³ on the 14th day after the end of treatment, and the average tumor volume of the FDA026-1402 treatment group at 10 mg/kg was 0.00 mm³ on the 14th day after the end of treatment. The average tumor volume of the FDA026-LE14 treatment group at 5.0 mg/kg was 13.79 mm³ on the 14th day after the end of treatment, and the average tumor volume of the FDA026-LE14 treatment group at 10 mg/kg was 0.00 mm³ on the 14th day after the end of treatment. The average tumor volume of the FDA028-LE14 treatment group at 5.0 mg/kg was 9.86 mm³ on the 14th day after the end of treatment, and the average tumor volume of the FDA028-LE14 treatment group at 10 mg/kg was 0.00 mm³ on the 14th day after the end of treatment. The experimental results show that both FDA026-LE14 and FDA028-LE14 have good antitumor activity in vivo, and all experimental mice have no death or weight loss, indicating that FDA026-LE14 has good safety.

TABLE 10

Antitumor activity of FDA026-LE14 in SW620 human colorectal cancer model

| Grouping | 11 | 14 | 18 | 21 | 25 | 28 | 32 | 35 | 39 | 42 | 46 |
|---|---|---|---|---|---|---|---|---|---|---|---|
| Average Tumor Volume/mm3 | | | | | | | | | | | |
| 01 | 159.75 | 284.67 | 538.37 | 797.32 | 1458.10 | 1740.41 | 2074.54 | / | / | / | / |
| 02 | 159.35 | 265.09 | 267.78 | 259.26 | 199.88 | 160.40 | 104.56 | 37.81 | 28.72 | 22.45 | 13.79 |
| 03 | 159.71 | 201.19 | 227.81 | 139.61 | 60.68 | 25.75 | 3.83 | 3.28 | 0.00 | 0.00 | 0.00 |
| 04 | 159.83 | 221.27 | 264.94 | 321.40 | 404.98 | 481.97 | 412.12 | 351.12 | 229.20 | 205.81 | 260.87 |
| 05 | 159.84 | 238.08 | 255.34 | 169.81 | 89.27 | 60.48 | 33.85 | 24.88 | 11.50 | 6.91 | 0.00 |
| 06 | 159.63 | 266.32 | 256.78 | 232.53 | 185.88 | 155.32 | 100.42 | 34.16 | 25.48 | 18.42 | 9.86 |
| 07 | 159.73 | 200.56 | 228.32 | 138.87 | 59.32 | 27.32 | 3.15 | 2.12 | 0.00 | 0.00 | 0.00 |
| 08 | 159.41 | 227.21 | 362.76 | 509.97 | 667.07 | 778.01 | 864.41 | 875.35 | 895.60 | 1017.45 | 1120.09 |
| Standard Deviation | | | | | | | | | | | |
| 01 | 10.37 | 31.73 | 32.42 | 77.06 | 85.50 | 81.66 | 92.36 | / | / | / | / |
| 02 | 10.81 | 30.80 | 21.55 | 22.67 | 31.96 | 34.21 | 20.45 | 10.13 | 8.38 | 6.24 | 6.25 |
| 03 | 11.03 | 23.15 | 33.03 | 29.12 | 13.67 | 7.39 | 3.83 | 3.28 | 0.00 | 0.00 | 0.00 |
| 04 | 10.74 | 27.49 | 32.75 | 53.43 | 65.56 | 87.31 | 85.57 | 90.69 | 63.81 | 69.14 | 86.58 |
| 05 | 10.93 | 18.63 | 20.43 | 21.58 | 12.07 | 7.35 | 9.19 | 6.84 | 5.87 | 4.37 | 0.00 |
| 06 | 10.82 | 25.36 | 26.54 | 25.36 | 23.46 | 26.57 | 19.23 | 9.47 | 8.53 | 5.47 | 5.32 |
| 07 | 11.31 | 18.34 | 22.01 | 21.32 | 12.01 | 7.12 | 5.32 | 5.93 | 0.00 | 0.00 | 0.00 |
| 08 | 10.40 | 31.79 | 63.03 | 98.30 | 119.71 | 162.30 | 206.93 | 204.40 | 218.88 | 253.08 | 273.36 |

Note:
Group 01 is the blank control group; group 02 is the FDA026-LE14 group with a dose of 5 mg/kg; group 03 is the FDA026-LE14 group with a dose of 10 mg/kg; group 04 is the FDA026-1402 group with a dose of 5 mg/kg; group 05 is the FDA026-1402 group with a dose of 10 mg/kg; group 06 is the FDA028-LE14 group with a dose of 5 mg/kg; group 07 is the FDA028-LE14 group with a dose of 10 mg/kg; group 08 is the Irinotecan hydrochloride group with a dose of 100 mg/kg.

What is claimed is:

1. An antibody-drug conjugate; the antibody-drug conjugate has a structure shown in formula I;

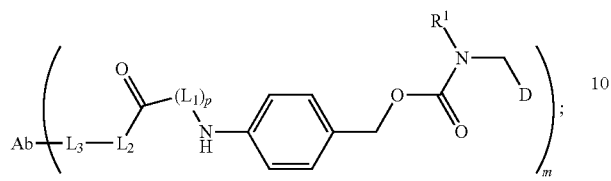

wherein Ab is a HER3 antibody A or a variant of the HER3 antibody A;
the amino acid sequence of the light chain in HER3 antibody A is shown in SEQ ID NO: 1, and the amino acid sequence of the heavy chain is shown in SEQ ID NO: 2;
the amino acid sequence of the light chain in the variant of HER3 antibody A is shown in SEQ ID NO: 1; the amino acid sequence of the heavy chain in the variant of HER3 antibody A is the amino acid sequence shown in SEQ ID NO: 2 having one or more than one site mutation of E233P, L234V, L234F, L235A, L235E, or P331S;
m is 2 to 8;
D is a cytotoxic drug topoisomerase inhibitor; the cytotoxic drug topoisomerase inhibitor is

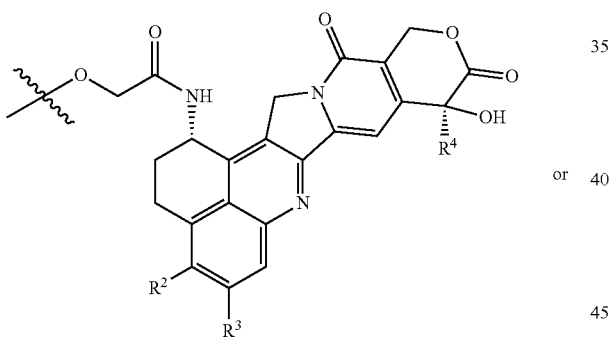

or

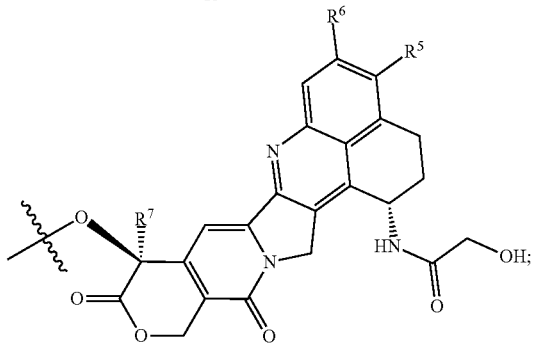

$R^2$ and $R^5$ are each independently H, $C_1$-$C_6$ alkyl or halogen;
$R^3$ and $R^6$ are each independently H, $C_1$-$C_6$ alkyl or halogen;
$R^4$ and $R^7$ are each independently $C_1$-$C_6$ alkyl;
$R^1$ is $C_1$-$C_6$ alkyl substituted by one $R^{1-3}S(O)_2$—, $R^{1-3}$ is $C_1$-$C_6$ alkyl;
$L_1$ is independently one or more than one of phenylalanine residue, alanine residue, glycine residue, glutamic acid residue, aspartic acid residue, cysteine residue, histidine residue, isoleucine residue, leucine residue, lysine residue, methionine residue, proline residue, serine residue, threonine residue, tryptophan residue, tyrosine residue, and valine residue; p is 2;
$L_2$ is

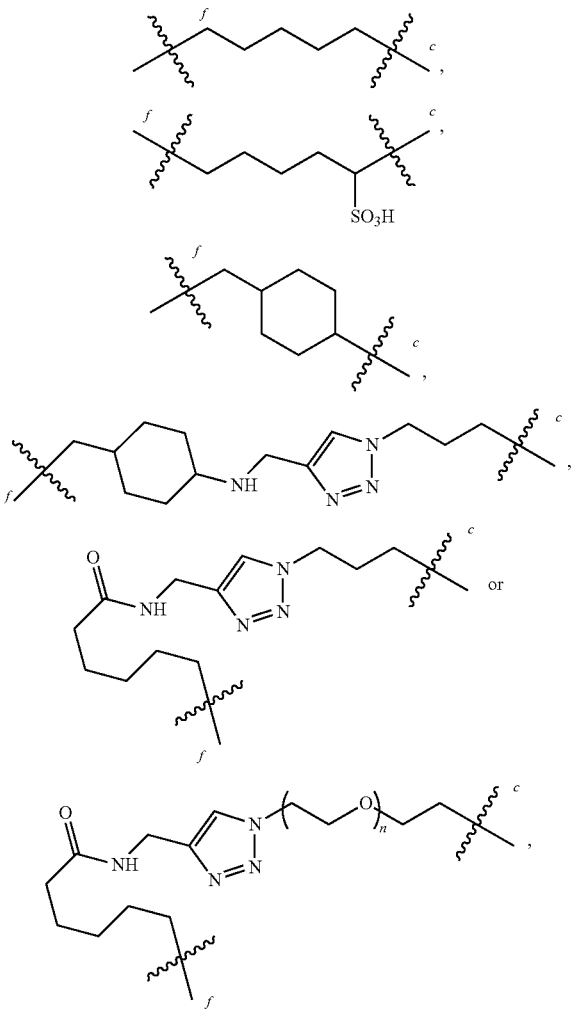

wherein n is independently 1 to 12, the c-terminal is connected to $L_1$ through a carbonyl group, and the f-terminal is connected to the d-terminal of $L_3$;
$L_3$ is

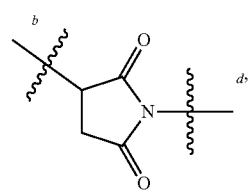 [SMILES: *C1CC(=O)N(*)C1=O]

wherein the b-terminal is connected to the Ab, and the d-terminal is connected to the f-terminal of $L_2$.

2. The antibody-drug conjugate according to claim 1, wherein the $C_1$-$C_6$ alkyl substituted by one $R^{1-3}S(O)_2$— is

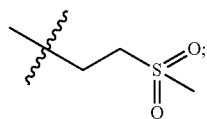
5
3. The antibody-drug conjugate according to claim 1, wherein the conjugate antibody-drug is
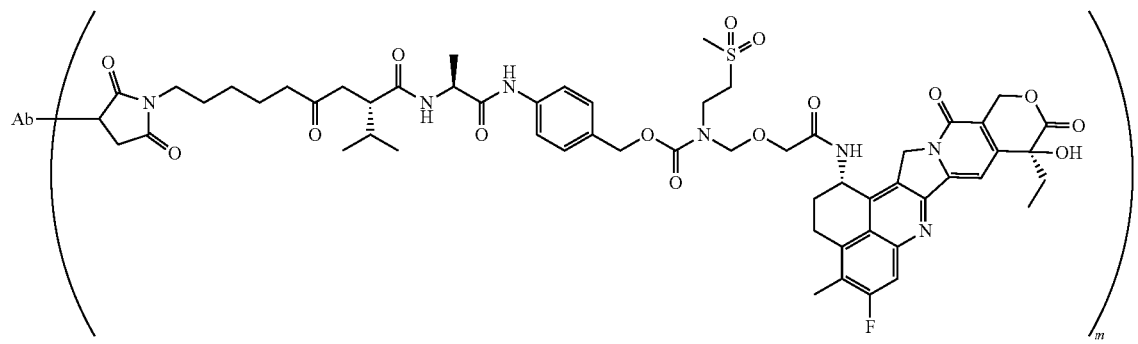
14
4. An antibody-drug conjugate wherein the antibody-drug conjugate is
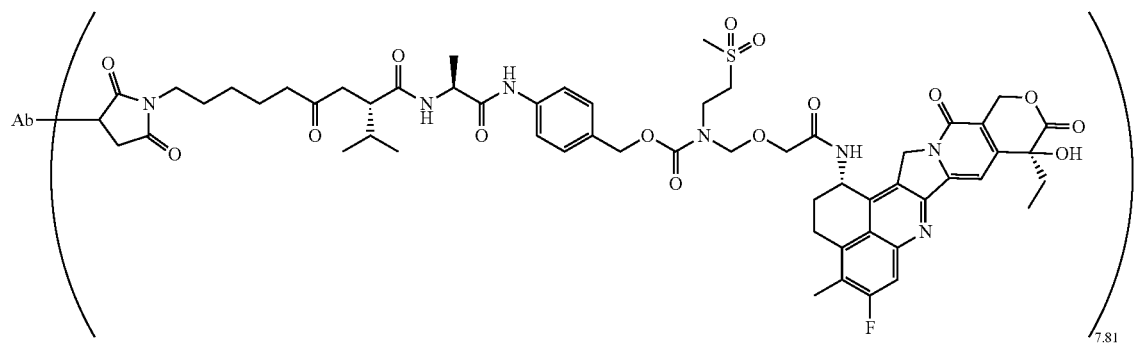
14
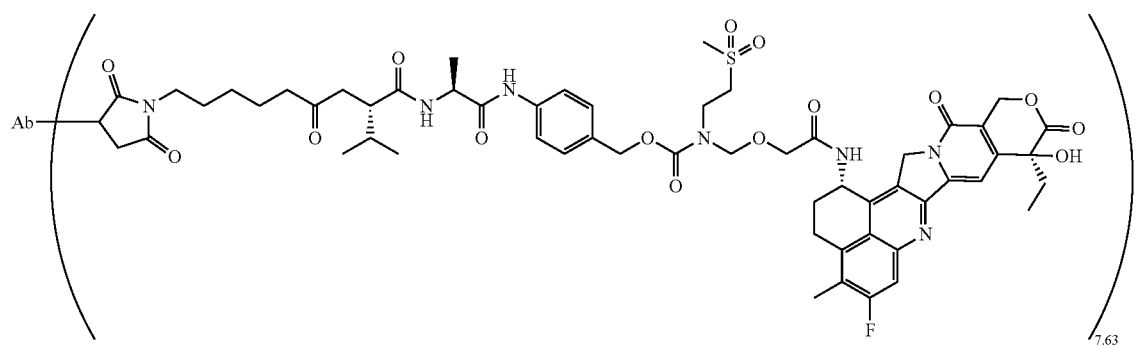
14

-continued

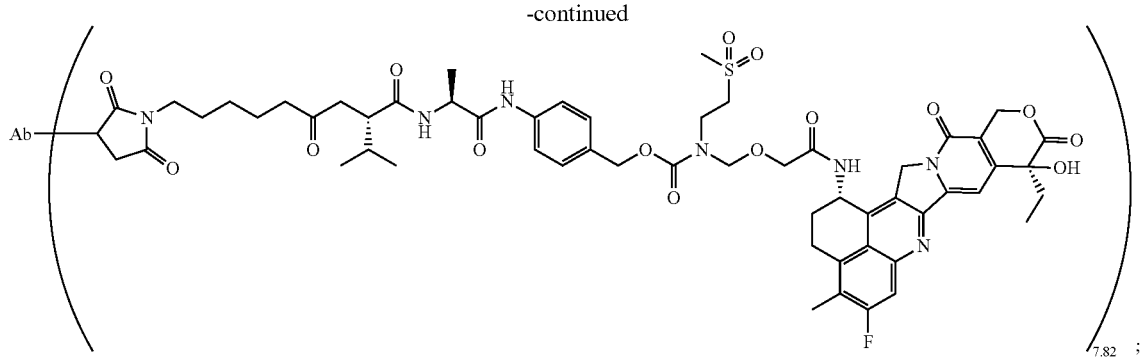
14 wherein Ab is HER3 antibody A or the variant of HER3 antibody A; the amino acid sequence of the light chain in HER3 antibody A is shown in SEQ ID NO: 1, and the amino acid sequence of the heavy chain is shown in SEQ ID NO: 2; the amino acid sequence of the light chain in the variant of HER3 antibody A is shown in SEQ ID NO: 1, the amino acid sequence of the heavy chain is selected from SEQ ID NO: 3 or SEQ ID NO: 4.

5. An antibody-drug conjugate, wherein the antibody-drug conjugate is

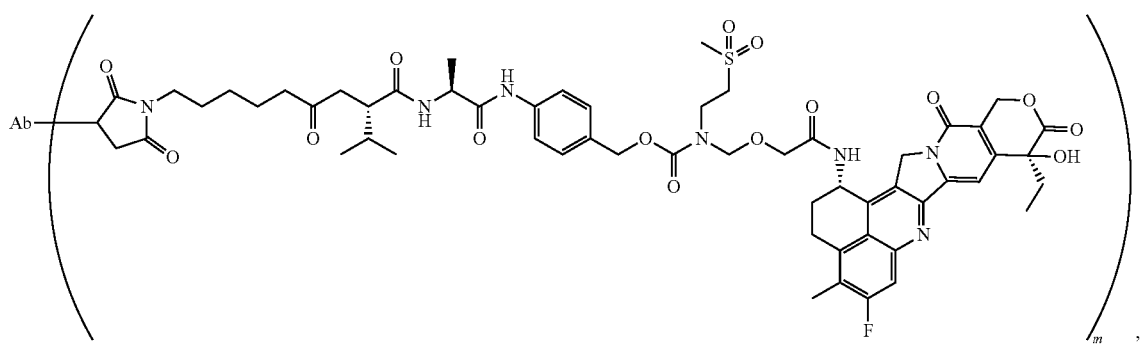
14 wherein Ab is HER3 antibody A or the variant of HER3 antibody A, and m is 7.56, 7.59, 7.63, 7.67, 7.72, 7.81, or 7.83; the amino acid sequence of the light chain in HER3 antibody A is shown in SEQ ID NO: 1, and the amino acid sequence of the heavy chain is shown in SEQ ID NO: 2; the amino acid sequence of the light chain in the variant of HER3 antibody A is shown in SEQ ID NO: 1, the amino acid sequence of the heavy chain is selected from SEQ ID NO: 3 or SEQ ID NO: 4.

6. The antibody-drug conjugate according to claim 4, wherein the antibody-drug conjugate is

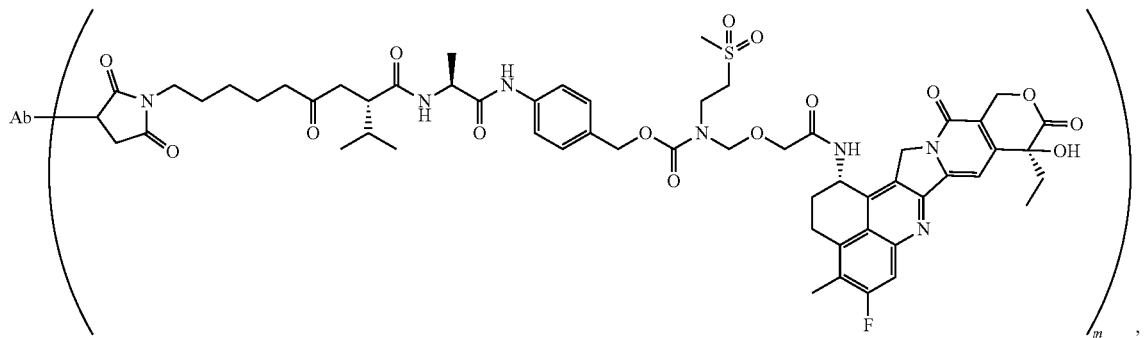

14

Ab is HER3 antibody A, and m is 7.81;

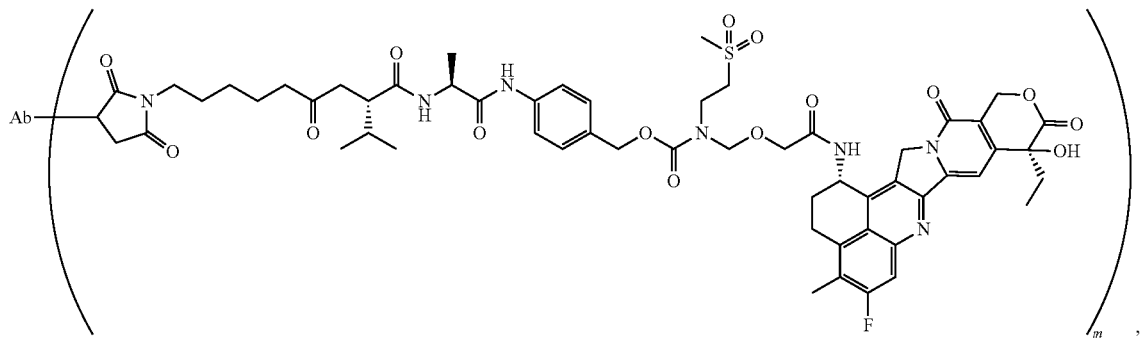

14

Ab is the variant of HER3 antibody A; the amino acid sequence of the light chain in the variant of HER3 antibody A is shown in SEQ ID NO: 1, and the heavy chain is the amino acid sequence shown in SEQ ID NO: 3, and m is 7.63;

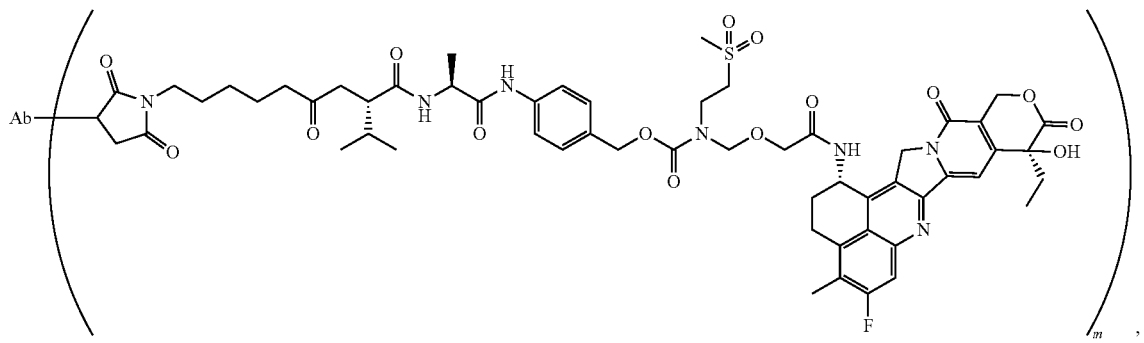

14

Ab is the variant of HER3 antibody A; the amino acid sequence of the light chain in the variant of HER3 antibody A is shown in SEQ ID NO: 1, and the heavy chain is the amino acid sequence shown in SEQ ID NO: 4, and m is 7.82.

* * * * *

SEQUENCE LISTING

<160> NUMBER OF SEQ ID NOS: 4

<210> SEQ ID NO 1
<211> LENGTH: 220
<212> TYPE: PRT
<213> ORGANISM: Homo sapiens

<400> SEQUENCE: 1

```
Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
```

```
                50                  55                  60
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 2
<211> LENGTH: 447
<212> TYPE: PRT
<213> ORGANISM: Homo sapiens

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 3
<211> LENGTH: 447
<212> TYPE: PRT
<213> ORGANISM: Artificial Sequence
<220> FEATURE:
<223> OTHER INFORMATION: FDA028 heavy chain

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Pro Val Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 4
<211> LENGTH: 447
<212> TYPE: PRT
<213> ORGANISM: Artificial Sequence
<220> FEATURE:
<223> OTHER INFORMATION: FDA029 heavy chain

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

-continued

```
Gly Glu Ile Asn His Ser Gly Ser Thr Asn Tyr Asn Pro Ser Leu Lys
 50              55                  60
Ser Arg Val Thr Ile Ser Val Glu Thr Ser Lys Asn Gln Phe Ser Leu
 65              70                  75                  80
Lys Leu Ser Ser Val Thr Ala Ala Asp Thr Ala Val Tyr Tyr Cys Ala
                 85                  90                  95
Arg Asp Lys Trp Thr Trp Tyr Phe Asp Leu Trp Gly Arg Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
210                 215                 220
Thr Cys Pro Pro Cys Pro Ala Pro Glu Phe Glu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```